United States Patent
Kim et al.

(10) Patent No.: US 9,969,887 B2
(45) Date of Patent: May 15, 2018

(54) MEROCYANINE-BASED COMPOUNDS, AND DYES, KITS AND CONTRAST MEDIUM COMPOSITIONS FOR LABELLING BIOMOLECULES COMPRISING THE SAME

(71) Applicant: SFC CO., LTD., Cheongju-si, Chungcheongbuk-do (KR)

(72) Inventors: Su-Jin Kim, Chuncheon-si (KR); Do-Min Lee, Asan-si (KR); Jong-Tae Je, Cheongju-si (KR)

(73) Assignee: SFC Co., Ltd., Cheongju-si, Chungcheongbuk-do (KR)

( * ) Notice: Subject to any disclaimer, the term of this patent is extended or adjusted under 35 U.S.C. 154(b) by 0 days. days.

(21) Appl. No.: 15/490,971

(22) Filed: Apr. 19, 2017

(65) Prior Publication Data

US 2017/0306155 A1    Oct. 26, 2017

(30) Foreign Application Priority Data

Apr. 20, 2016 (KR) .......................... 10-2016-0048233
Dec. 28, 2016 (KR) .......................... 10-2016-0181338

(51) Int. Cl.

| | | |
|---|---|---|
| *C07D 513/22* | (2006.01) | |
| *C07D 513/14* | (2006.01) | |
| *C07D 519/00* | (2006.01) | |
| *G01N 33/52* | (2006.01) | |
| *C12Q 1/6844* | (2018.01) | |
| *C12Q 1/6813* | (2018.01) | |
| *C09B 49/12* | (2006.01) | |
| *C07D 417/08* | (2006.01) | |
| *C12C 1/02* | (2006.01) | |
| *C07F 5/02* | (2006.01) | |
| *G01N 27/447* | (2006.01) | |
| *G01N 21/31* | (2006.01) | |
| *C12Q 1/68* | (2018.01) | |

(52) U.S. Cl.
CPC ............ *C09B 49/12* (2013.01); *C07D 417/08* (2013.01); *C07D 513/14* (2013.01); *C07D 513/22* (2013.01); *C07D 519/00* (2013.01); *C07F 5/022* (2013.01); *C12C 1/02* (2013.01); *G01N 33/52* (2013.01); *C12Q 1/6813* (2013.01); *C12Q 1/6844* (2013.01); *G01N 27/44778* (2013.01); *G01N 2021/3155* (2013.01)

(58) Field of Classification Search
CPC .. C07D 513/22; C07D 513/14; C07D 519/00; G01N 33/52; C12Q 1/6844; C12Q 1/6813
USPC ............ 548/148; 549/381; 546/41; 435/6.11, 435/6.12, 120, 125
See application file for complete search history.

(56) References Cited

FOREIGN PATENT DOCUMENTS

JP    2009-192543 A    8/2009
JP    2011-99862 A     5/2011

OTHER PUBLICATIONS

Zhang, S., J. Fan, Z. Li, N. Hao, J. Cao, T. Wu, J. Wang, and X. Peng, "A bright red fluorescent cyanine dye for live-cell nucleic acid imaging, with high photostability and a large Stokes shift" J. Mater. Chem. B. (2014), 2: pp. 2688-2693. (Year: 2014).*
"SYBR(TM) Safe DNA Gel Stain", Feb. 15, 2016, MP33100, XP055401016, Thermo Fisher Scientific, Retrieved from the Internet.
"SYBR Green I Nucleic Acid Gel Stain", Mar. 16, 2006, pp. 1-6, MP07567, XP055401025, Molecular Probes, Inc., Retrieved from the Internet.
"Live/Dead Sperm Viability Kit ( L-7011 )", Mar. 14, 2001, pp. 1-3, XP055401030, Molecular Probes, Inc., Retrieved from the Internet.
"Fast EvaGreen qPCR Master Mix", Aug. 6, 2012, pp. 1-4, XP055401035, Biotium, Inc., Retrieved from the Internet.
Extended European Search Report dated Aug. 31, 2017 from European Patent Office in connection with the counterpart European Patent Application No. 17167034.2.
Alexander Zarkov et al., Novel Fluorescent Dyes for Single DNA Molecule Techniques, Molecular Imaging, Mar.-Apr. 2013, pp. 90-99, vol. 12, No. 2, Decker Publishing.
Japanese Office Action dated Mar. 2, 2018 in connection with the counterpart Japanese Patent Application No. 2017-083726, citing the above reference(s).

* cited by examiner

*Primary Examiner* — Matthew P Coughlin
*Assistant Examiner* — Sagar Patel
(74) *Attorney, Agent, or Firm* — Hauptman Ham, LLP

(57) ABSTRACT

The present disclosure relates to a novel merocyanine-based compound capable of labeling biomolecules by intercalating biomolecules, and to a dye, kit and contrast medium composition for labelling biomolecules comprising the same.

12 Claims, 33 Drawing Sheets

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: a forward primer for Hela cDNA amplification

<400> SEQUENCE: 1
gtatgacaac agcctcaaga t                                                 21

<210> SEQ ID NO 2
<211> LENGTH: 20
<212> TYPE: DNA
<213> ORGANISM: Artificial
<220> FEATURE:
<223> OTHER INFORMATION: a reverse primer for Hela cDNA amplification

<400> SEQUENCE: 2
agtccttcca cgataccaaa                                                   20
```

MEROCYANINE-BASED COMPOUNDS, AND DYES, KITS AND CONTRAST MEDIUM COMPOSITIONS FOR LABELLING BIOMOLECULES COMPRISING THE SAME

This research was supported by a grant from the Advanced Technology Center (ATC) Program (10076988, Development of fluorescent materials and their application technologies for molecular diagnosis) funded by the Ministry of Trade, Industry & Energy of the Republic of Korea.

CROSS-REFERENCE TO RELATED APPLICATIONS

This application claims priority to Korean Patent Application No. 10-2016-0048233 filed on Apr. 20, 2016, and Korean Patent Application No. 10-2016-0181338 filed on Dec. 28, 2016, all the benefits accruing there from under 35 U.S.C. § 119, the contents of which is incorporated by reference in its entirety.

BACKGROUND

1. Technical Field

The present disclosure relates to a novel merocyanine-based compound capable of labeling biomolecules by intercalating biomolecules, and to a dye, kit and contrast medium composition for labelling biomolecules comprising the same.

2. Description of the Related Art

Fluorescent dyes have been used for the detection of a variety of biological samples involving nucleic acids, and nucleic acids including DNA and RNA. Accordingly, studies have been actively made on fluorescent nucleic acid dyes that are specifically bound or intercalated into nucleic acids to form a complex exhibiting excellent fluorescence.

Dyes specifically bound or intercalated into nucleic acids can be used in pure solutions, cell extracts, electrophoresis gels, microarray chips, living or immobilized cells, apoptotic cells and environmental samples, and can be used to detect the presence and amount of DNA and RNA in various samples. In particular, such fluorescent dyes can be used for the detection of nucleic acids through polymerase chain reaction (PCR), which is a typical method used in genome research and medical diagnosis.

In this case, since a quantitative PCR which is proportional to the amount of the sample nucleic acids is impossible in the case of general end-point PCR, real-time quantitative PCR (real-time PCR or qPCR) is mainly used for quantitative analysis of the amount of nucleic acids by measuring the fluorescence value changing in real time for each amplification cycle.

Such qPCR allows quantitative analysis by measuring the fluorescence signal from the PCR result. As a method for measuring the fluorescence signal, a detection method using a fluorescent probe and a detection method using an intercalating fluorescent dye are mainly known.

A detection method using a fluorescent probe uses a probe (for example, an oligonucleotide) labeled with a complex of a fluorescent dye and a quencher dye. When an oligonucleotide labeled with a complex of a fluorescent dye and a quencher dye is hybridized with a target sequence, the fluorescent dye is cleaved and separated from the complex to generate a fluorescence signal.

The detection method using the above-described fluorescent probe has an advantage of high selectivity and specificity with respect to a target sequence, but has a disadvantage that it is complex in design and expensive to use in a large amount.

The detection method using intercalating fluorescent dyes is based on DNA-binding fluorescent dyes referred to as fluorescent nucleic acid dyes or stains. Fluorescent nucleic acid dyes are advantageous because they are relatively simple molecules and therefore are easy to design and manufacture and relatively inexpensive.

However, since several criteria must be met to be used in qPCR, not all commonly known fluorescent nucleic acid dyes can be used for qPCR.

For example, fluorescent nucleic acid dyes used in qPCR should have sufficient stability during storage and PCR and should be resistant to pH range of a buffer used for PCR.

In addition, when nucleic acids are not present, the fluorescent nucleic acid dye should generate no fluorescence signal or generate only a very weak fluorescence signal, and generate a relatively strong fluorescence signal in the presence of nucleic acid.

The most commonly used dyes for the labeling of conventional nucleic acids are the following ethidium bromide:

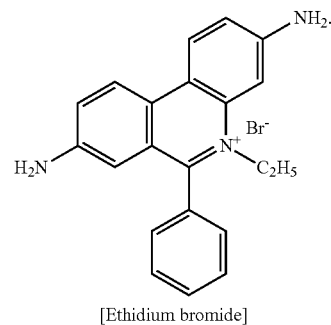 [SMILES: CC[n+]1c(-c2ccccc2)c2cc(N)ccc2c2ccc(N)cc21 ; [Br-]]

[Ethidium bromide]

The ethidium bromide is, for example, used (post-stained) to stain a gel that has undergone electrophoresis, and is preliminarily added in the preparation of the electrophoresis gel and used (pre-stained) for electrophoresis and staining. In addition, since ethidium bromide generates UV light of 400 nm or less and has an emission spectrum of about 620 nm when bound to DNA, it has an advantage that the presence and position of DNA can be visually confirmed easily.

In spite of the advantages of the above-mentioned ethidium bromide, ethidium bromide is a mutagen and carcinogen, which therefore requires a great deal of caution in use. In particular, research has shown that ethidium bromide interferes with the synthesis of DNA and RNA, thereby causing mutations as DNA replication is inhibited.

As a result, SYBR® green I was mainly used as a substitute fluorescent dye showing non-genotoxicity. However, since SYBR® green I inhibits the PCR process, simply increasing the concentration of SYBR® green I has the limitation that a higher maximum fluorescence signal cannot be obtained.

In other words, the intensity of the fluorescence signal increases in proportion to the concentration of SYBR® green I until a baseline concentration at which the concentration of SYBR® green I begins to significantly inhibit the PCR process. From then on, however, DNA amplification is reduced with an additional increase in concentration of the SYBR® green I. As a result, the intensity of the observed fluorescence signal is decreased, or a threshold cycle for observing the fluorescence signal of a predetermined intensity or more is increased.

It is also known that SYBR® green I is unstable under certain chemical conditions and therefore degrades considerably within a few days in a buffer solution.

SUMMARY

Under the above technical background, the present disclosure aims to provide a merocyanine-based compound as an intercalating fluorescent dye suitable for use in qPCR using an intercalating fluorescent dye.

It is also an object of the present disclosure to provide a non-genotoxic merocyanine-based compound unlike the ethidium bromide.

It is another object of the present disclosure to provide a merocyanine-based compound capable of increasing the intensity of a fluorescence signal in proportion to a nucleic acid concentration without increasing a threshold number of cycle.

It is still another object of the present disclosure to provide a dye, a kit and a contrast medium composition containing the above merocyanine-based compound.

It is still yet another object of the present disclosure to provide a method for determining and quantifying the presence or absence of nucleic acid or the cell viability using the merocyanine-based compound.

In accordance with one aspect of the present disclosure, there is provided a merocyanine-based compound having a structure represented by the following formula 1:

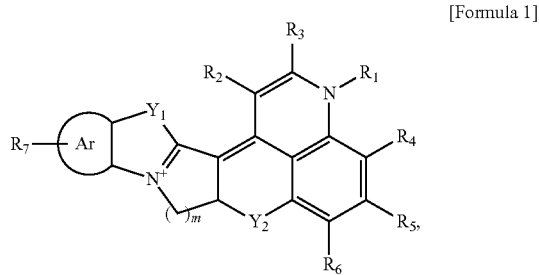

[Formula 1]

wherein

Ar is a substituted or unsubstituted aromatic ring;

$Y_1$ and $Y_2$ are each independently selected from sulfur, oxygen, selenium, $NR_8$ and $-CR_8=CR_9-$;

$R_1$ to $R_9$ are each independently selected from the group consisting of hydrogen, deuterium, substituted or unsubstituted $C_1$-$C_{10}$ alkyl, substituted or unsubstituted $C_2$-$C_{10}$ heteroalkyl containing at least one heteroatom, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted aryloxy, substituted or unsubstituted $C_1$-$C_{10}$ haloalkyl, halogen, cyano, hydroxyl, substituted or unsubstituted amino, substituted or unsubstituted amide, carbamate, sulfhydryl, nitro, carboxyl, carboxylate, substituted or unsubstituted aryl, substituted or unsubstituted heteroaryl, substituted or unsubstituted aralkyl, quaternary ammonium, phosphoric acid, phosphate, phosphonate, ketone ($-COR_{10}$), aldehyde, ester ($-COOR_{10}$), acyl chloride, sulfonic acid, sulfonate, polyalkylene oxide, and -L-Z functional groups;

when $R_a$, wherein a is an integer selected from 1 to 9, is a ketone group ($-COR_{10}$) or an ester group ($-COOR_{10}$), $R_{10}$ is selected from the group consisting of substituted or unsubstituted $C_1$-$C_{10}$ alkyl, substituted or unsubstituted $C_2$-$C_{10}$ heteroalkyl containing at least one heteroatom, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted $C_1$-$C_{10}$ haloalkyl, and substituted or unsubstituted $C_1$-$C_{10}$ aminoalkyl;

when $R_b$, wherein b is an integer selected from 1 to 10, is substituted, any carbon or terminal carbon in the functional groups may be substituted with at least one substituent selected from the group consisting of sulfonic acid, sulfonate, ketone, aldehyde, carboxylic acid, carboxylate, phosphoric acid, phosphate, phosphonate, acyl chloride, polyalkylene oxide, quaternary ammonium salt, ester, and amide;

m is an integer of 1 to 3;

L is a linker comprising 3 to 150 non-hydrogen atoms;

Z is a fluorescent moiety capable of generating a fluorescent signal, or has a structure represented by formula 1; and wherein the structure represented by the formula 1 has one or two -L-Z functional groups.

Here, as fluorescent moieties capable of generating a fluorescent signal, Z may be selected from the group consisting of phenanthridium, coumarins, cyanine, bodipy, fluoresceins, rhodamines, pyrenes, carbopyronin, oxazine, xanthenes, thioxanthene, and acridine.

According to one embodiment of the present disclosure, the -L-Z functional group may be represented by the following formula 2:

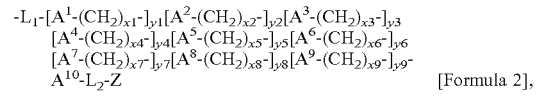

[Formula 2], wherein $L_1$ and $L_2$ are each independently a $C_1$-$C_{12}$ polymethylene unit optionally containing at least one heteroatom selected from nitrogen, oxygen and sulfur, or an aryl optionally containing at least one heteroatom selected from nitrogen, oxygen and sulfur; $A^1$ to $A^{10}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur; x1 to x9 are each independently 0 or an integer of 1 to 20; and y1 to y9 are each independently 0 or an integer of 1 to 20.

Further, Z may be selected from the group consisting of phenanthridium, coumarins, cyanine, bodipy, fluoresceins, rhodamines, pyrenes, carbopyronin, oxazine, xanthenes, thioxanthene, and acridine, or may have a different fluorescent moiety structure.

According to another embodiment, one of $A^1$ to $A^{10}$ may be represented by the following formula 3:

[Formula 3]

wherein $R_{11}$ is an aryl optionally containing at least one heteroatom selected from carbon, nitrogen, oxygen and sulfur, and $R_{12}$ is represented by the following formula 4.

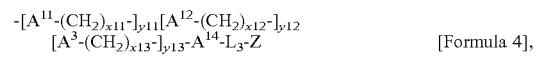

[Formula 4], wherein $L_3$ is a $C_1$-$C_{12}$ polymethylene unit optionally containing at least one heteroatom selected from nitrogen, oxygen and sulfur, or an aryl optionally containing at least one heteroatom selected from nitrogen, oxygen and sulfur; $A^{11}$ to $A^{14}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur; x11 to x13 are each independently 0 or an integer of 1 to 20; and y11 to y13 are each independently 0 or an integer of 1 to 20.

Further, according to another aspect of the present disclosure, a dye for labeling biomolecules comprising the merocyanine-based compound is provided.

Further, according to another aspect of the present disclosure, a kit for labeling biomolecules comprising the merocyanine-based compound is provided.

Further, according to another aspect of the present disclosure, a contrast medium composition for labeling biomolecules comprising the merocyanine-based compound is provided.

Further, according to another aspect of the present disclosure, an electrophoresis kit for determining the presence or absence of nucleic acid in a sample is provided.

Further, according to another aspect of the present disclosure, a method of determining or quantifying the presence or absence of nucleic acid in a sample is provided.

Further, according to another aspect of the present disclosure, a method of analyzing or quantifying the viability of cells in a sample is provided.

The novel merocyanine-based compound according to the present disclosure can exhibit fluorescence signals in the visible light region by intercalating biomolecules and exhibit non-genotoxicity, and, therefore, based on this, the merocyanine-based compound can be usefully used as dyes for labeling biomolecules, kits for labeling biomolecules, and contrast medium compositions for labeling biomolecules.

DETAILED DESCRIPTION

Figure 1:
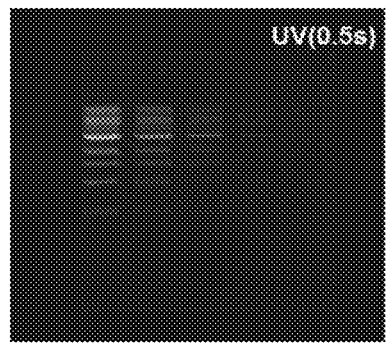
FIG. 1 shows an electrophoresis result of SYBR® safe, a commercially available dye.
Figure 2:
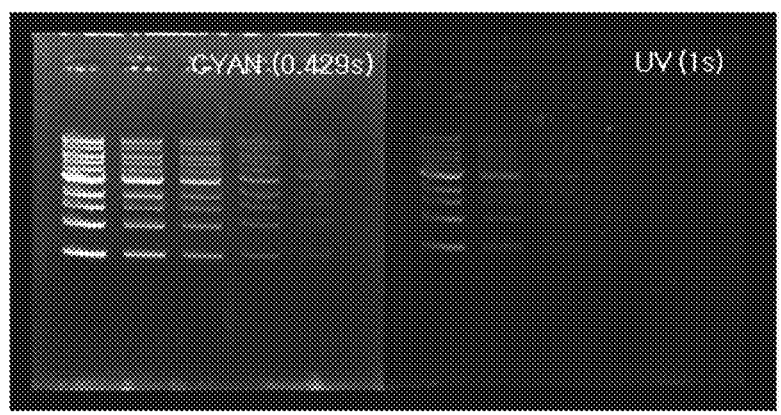
FIGS. 2 to 10 show electrophoresis results of merocyanine-based compounds according to various embodiments of the present disclosure.
Figure 3:
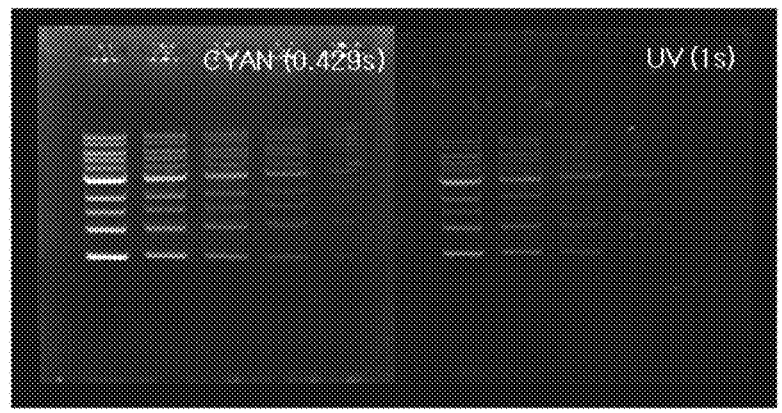
Figure 4:
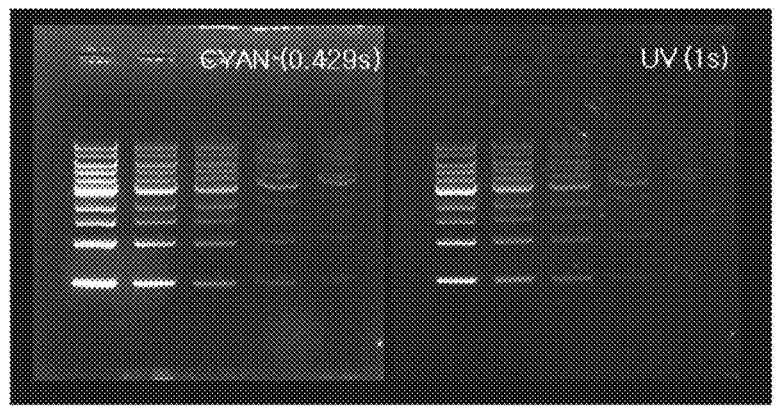
Figure 5:
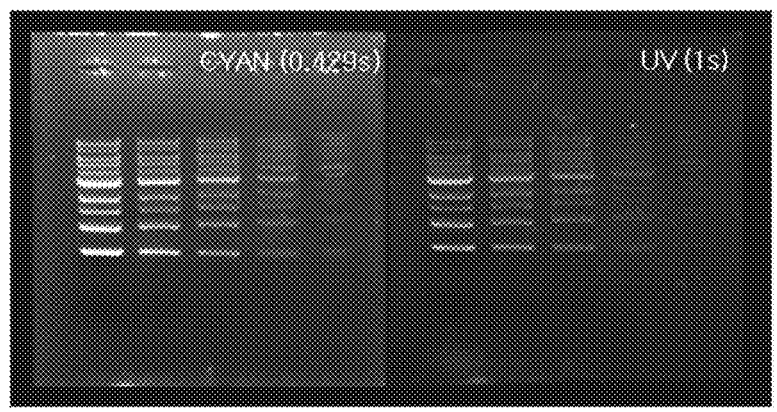
Figure 6:
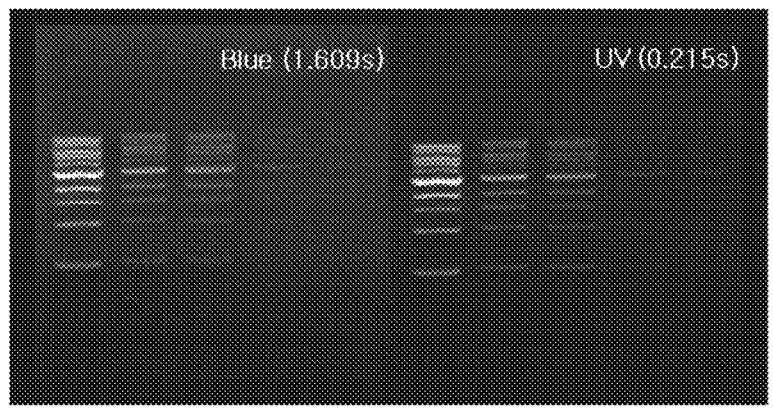
Figure 7:
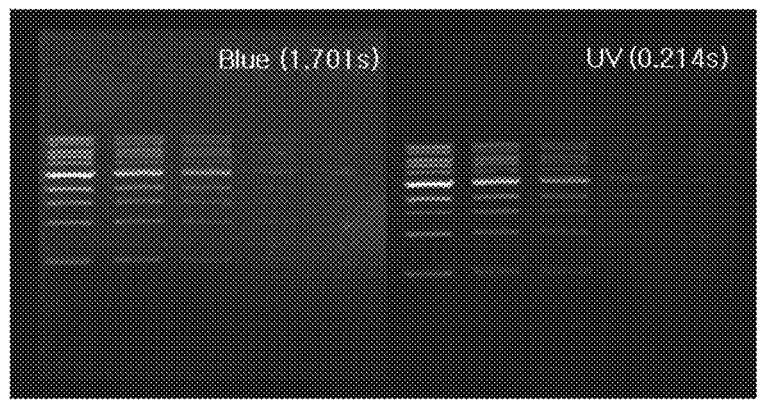
Figure 8:
Figure 9:
Figure 10:
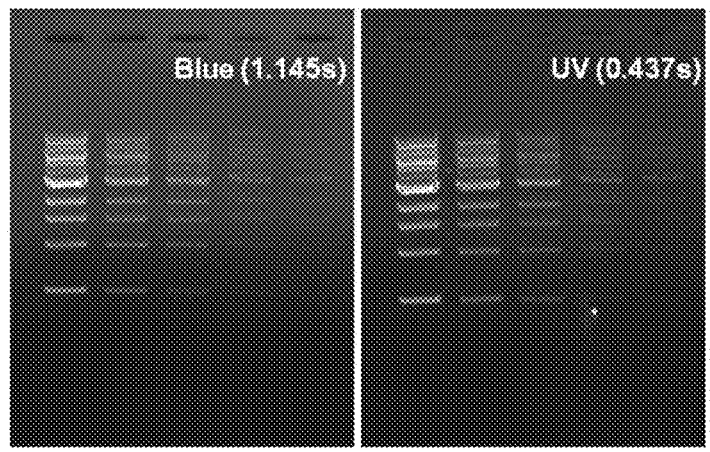

Certain terms are herein defined for convenience in order to facilitate a better understanding of the present disclosure. Unless otherwise defined herein, scientific and technical terms used in the present disclosure shall have the meanings commonly understood by one of ordinary skill in the art.

In addition, unless the context clearly indicates otherwise, it should be understood that singular form of the term includes plural forms thereof, and plural forms of the terms may include singular forms thereof.

Merocyanine-based Compound

According to one aspect of the present disclosure, a merocyanine-based compound having a structure represented by the following formula 1 can be provided:

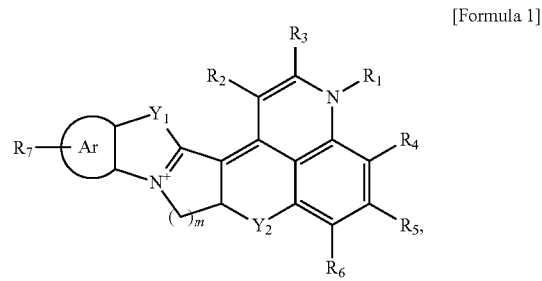

[Formula 1]

wherein Ar is a substituted or unsubstituted aromatic ring such as benzo or naphtho group, and $Y_1$ and $Y_2$ are each independently selected from the group consisting of sulfur, oxygen, selenium, $NR_8$ and $—CR_8=CR_9—$, and m is an integer of 1 to 3.

$R_1$ to $R_9$ are each independently selected from the group consisting of hydrogen, deuterium, substituted or unsubstituted $C_1$-$C_{10}$ alkyl, substituted or unsubstituted $C_2$-$C_{10}$ heteroalkyl containing at least one heteroatom, substituted or unsubstituted $C_2$-$C_{10}$ alkenyl, substituted or unsubstituted $C_2$-$C_{10}$ alkynyl, substituted or unsubstituted $C_1$-$C_{10}$ alkoxy, substituted or unsubstituted aryloxy, substituted or unsubstituted $C_1$-$C_{10}$ haloalkyl, halogen, cyano, hydroxyl, substituted or unsubstituted amino, substituted or unsubstituted amide, carbamate, sulfhydryl, nitro, carboxyl, carboxylate, substituted or unsubstituted aryl, substituted or unsubstituted heteroaryl, substituted or unsubstituted aralkyl, quaternary ammonium, phosphoric acid, phosphate, phosphonate, ketone (—$COR_{10}$), aldehyde, ester (—$COOR_{10}$), acyl chloride, sulfonic acid, sulfonate, polyalkylene oxide, and -L-Z functional groups.

When $R_a$ (where a is an integer selected from 1 to 9) is alkenyl or alkynyl, sp$^2$-hybridized carbon of alkenyl or sp-hybridized carbon of alkynyl is bonded directly or sp$^2$-hybridized carbon of alkenyl or sp-hybridized carbon of alkynyl is bonded indirectly via sp$^3$-hybridized carbon of alkyl.

As used herein, the term "$C_a$-$C_b$ functional group" refers to a functional group having a to b carbon atoms. For example, $C_a$-$C_b$ alkyl means a saturated aliphatic group, including a straight chain or branched alkyl having from a to b carbon atoms. The straight chain or branched alkyl has not more than 10 carbon atoms in its primary skeleton (for example, $C_1$-$C_{10}$ straight chain, or $C_3$-$C_{10}$ branched chain), preferably not more than 4, more preferably not more than 3 carbon atoms.

Specifically, as used herein, the term "alkyl" may include, but is not limited to, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl.

As used herein, the term "alkoxy" refers to both an —O-(alkyl) group and an —O- (unsubstituted cycloalkyl) group, and may be a straight chain or branched hydrocarbon having at least one ether group and from 1 to 10 carbon atoms.

Specifically, alkoxy may include, but is not limited to, methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, and cyclohexyloxy.

As used herein, the term "halogen" refers to fluoro (—F), chloro (—Cl), bromo (—Br) or iodo (—I), and the term "haloalkyl" refers to an alkyl substituted with halogen as described above. For example, halomethyl is a methyl in which at least one of the hydrogens of methyl is replaced by halogen, i.e., —$CH_2X$, —$CHX_2$ or —$CX_3$.

As used herein, the term "aralkyl" refers to a generic term for —$(CH_2)_n$Ar, an aryl group that is substituted with one or more alkyl groups. Examples of aralkyl include benzyl (—$CH_2C_6H_5$) or phenethyl (—$CH_2CH_2C_6H_5$).

As used herein, the term "aryl", unless otherwise defined, refers to an unsaturated aromatic ring comprising a single ring or multiple rings (preferably one to four rings) fused or covalently bonded to each other. Non-limiting examples of aryl include phenyl, biphenyl, o-terphenyl, m-terphenyl, p-terphenyl, 1-naphthyl, 2-naphthyl, 1-anthryl, 2-anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl, and 4-pyrenyl.

As used herein, the term "heteroaryl" refers to a functional group in which at least one carbon atom in the aryl as defined above is replaced by a non-carbon atom such as nitrogen, oxygen or sulfur. Non-limiting examples of heteroaryl include furyl, tetrahydrofuryl, phrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazoyl, acridinyl, phenazinyl, phenothizinyl, phenoxazinyl, purinyl, benzimidazolyl, and benzothiazolyl, and fused analogues thereof.

A hydrocarbon ring (e.g., cycloalkyl) or a hydrocarbon ring (e.g., heterocycloalkyl) containing a heteroatom herein may be understood as a ring structure of alkyl or heteroalkyl, respectively, unless otherwise defined.

Non-limiting examples of hydrocarbon rings include, but are not limited to, cyclopentyl, cyclohexyl, 1-cyclohexenyl, 3-cyclohexenyl, and cycloheptyl. Non-limiting examples of hydrocarbon rings containing a heteroatom include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, and 2-piperazinyl.

A hydrocarbon ring or a hydrocarbon ring containing a heteroatom may also have a hydrocarbon ring, a hydrocarbon ring containing a heteroatom, aryl or heteroaryl fused or covalently bonded thereto.

When $R_a$, wherein a is an integer selected from 1 to 9, is a ketone group (—$COR_{10}$) or an ester group (—$COOR_{10}$), $R_{10}$ may be selected from the group consisting of substituted or unsubstituted $C_1$-$C_{10}$ alkyl, substituted or unsubstituted $C_2$-$C_{10}$ heteroalkyl containing at least one heteroatom, substituted or unsubstituted $C_2$-$C_{10}$ alkenyl, substituted or unsubstituted $C_2$-$C_{10}$ alkynyl, substituted or unsubstituted $C_2$-$C_{10}$ alkoxy, substituted or unsubstituted $C_1$-$C_{10}$ haloalkyl, and substituted or unsubstituted $C_1$-$C_{10}$ aminoalkyl.

When $R_b$, wherein b is an integer selected from 1 to 10, is substituted, any carbon or terminal carbon in the functional groups may be substituted with at least one substituent selected from the group consisting of sulfonic acid, sulfonate, ketone, aldehyde, carboxylic acid, carboxylate, phosphoric acid, phosphate, acyl chloride, polyalkylene oxide, quaternary ammonium salt, ester, and amide.

Here, the polyalkylene oxide may be additionally substituted as necessary within the range in which the properties of the polymer are maintained. For example, the substitution may be a chemical bond to increase or decrease the chemical or biological stability of the polymer. By way of specific examples, any carbon or terminal carbon in the polyalkylene oxide may be substituted with one or more substituents selected from the group consisting of hydroxy, alkyl ether (methyl ether, ethyl ether, propyl ether, etc.), carboxymethyl ether, carboxyethyl ether, benzyl ether, dibenzylmethylene ether, or dimethylamine. In one embodiment, the polyalkylene oxide may be a polyalkylene oxide (mPEG) terminated with methyl ether, wherein mPEG is represented by the formula —$(CH_2CH_2O)_nCH_3$, the size of mPEG may vary depending on the number (n) of repeating units of ethylene glycol.

According to various embodiments of the present disclosure, $R_a$ (where a is an integer selected from 1 to 9) may have at least one -L-Z functional group.

Here, L is a linker comprising 3 to 150 non-hydrogen atoms connecting a structure represented by formula 1 and Z, which is a fluorescent moiety capable of generating a fluorescence signal, and specifically, comprising 8 to 150 non-hydrogen atoms.

Also, Z may a fluorescent moiety selected from the group consisting of phenanthridium, coumarins, cyanine, bodipy, fluoresceins, rhodamines, pyrenes, carbopyronin, oxazine, xanthenes, thioxanthene and acridine, or may have a structure represented by the formula 1.

According to one embodiment of the present disclosure, the -L-Z functional group may be represented by the following formula 2:

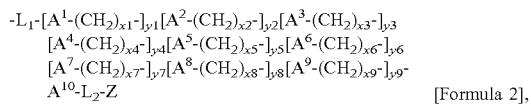   [Formula 2], wherein $L_1$ and $L_2$ are each independently a $C_1$-$C_{12}$ polymethylene unit optionally containing at least one heteroatom selected from nitrogen, oxygen and sulfur, or an aryl optionally containing at least one heteroatom selected from nitrogen, oxygen and sulfur; $A^1$ to $A^{10}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur; x1 to x9 are each independently 0 or an integer of 1 to 20; and y1 to y9 are each independently 0 or an integer of 1 to 20.

Also, Z may be selected from the group consisting of phenanthridium, coumarins, cyanine, bodipy, fluoresceins, rhodamines, pyrenes, carbopyronin, oxazine, xanthenes, thioxanthene, and acridine, or may have any different fluorescent moiety.

According to another embodiment, one of $A^1$ to $A^{10}$ may be represented by the following formula 3:

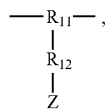   [Formula 3]

wherein $R_{11}$ is an aryl optionally containing at least one heteroatom selected from carbon, nitrogen, oxygen and sulfur, and $R_{12}$ is represented by the following formula 4:

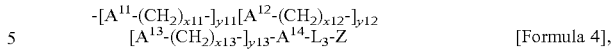   [Formula 4], wherein $L_3$ is a $C_1$-$C_{12}$ polymethylene unit optionally containing at least one heteroatom selected from nitrogen, oxygen and sulfur, or an aryl optionally containing at least one heteroatom selected from nitrogen, oxygen and sulfur; $A^{11}$ to $A^{14}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur; x11 to x13 are each independently 0 or an integer of 1 to 20; and y11 to y13 are each independently 0 or an integer of 1 to 20.

In addition, the merocyanine-based compound according to one embodiment of the present disclosure may have a structure further comprising a counter ion. The counter ion may be an organic or inorganic anion, and can be appropriately selected in consideration of solubility and stability of the merocyanine-based compound.

Examples of the counter ion of the merocyanine-based compound according to an embodiment of the present disclosure include an inorganic acid anion such as a phosphonic acid hexafluoride ion, a halogen ion, a phosphoric acid ion, a perchloric acid ion, a periodic acid ion, an antimony hexafluoride ion, tartaric acid hexafluoride ion, a fluoroboric acid ion, and a tetrafluoride ion, and an organic acid ion such as a thiocyanate ion, a benzenesulfonic acid ion, an alkylcarboxylic acid ion, a trihaloalkylcarboxylic acid ion, an alkylsulfonic acid ion, a trihaloalkylsulfonic acid ion, and a nicotinic acid ion. In addition, metal compound ions such as bisphenyldithol, thiobisphenol chelate and bisdiol-α-diketone, metal ions such as sodium and potassium, and quaternary ammonium salts can also be selected as counter ions.

The merocyanine-based compounds according to various embodiments of the present disclosure are as follows:

[Compound 1]

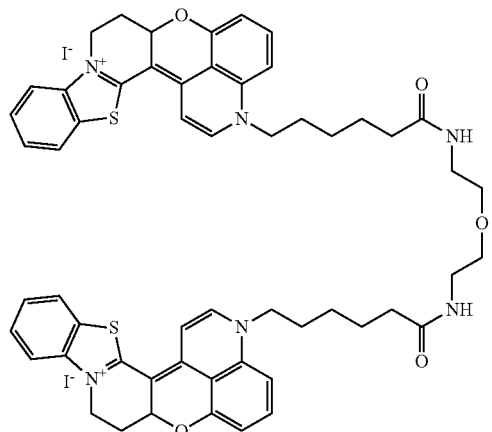

[Compound 2]

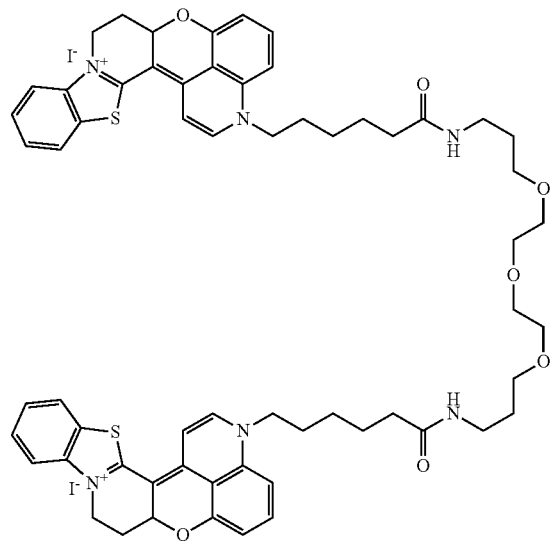

-continued
[Compound 3]
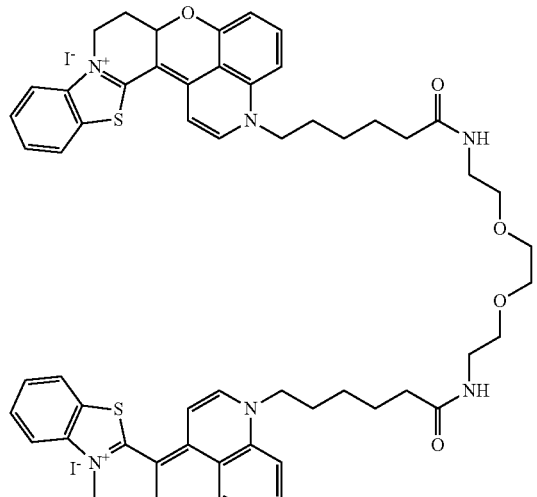
[Compound 4]
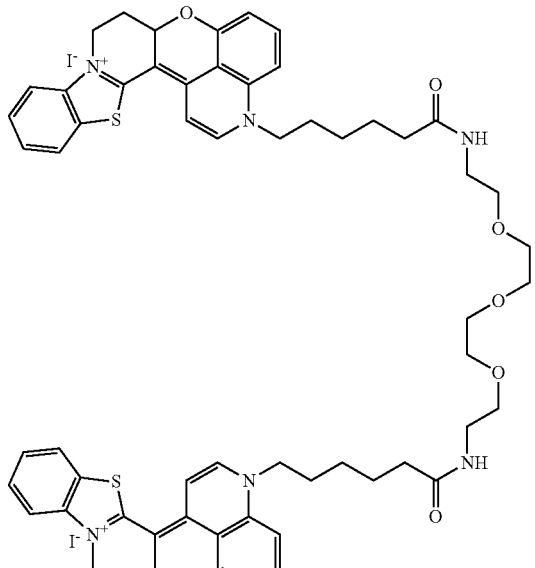
[Compound 5]
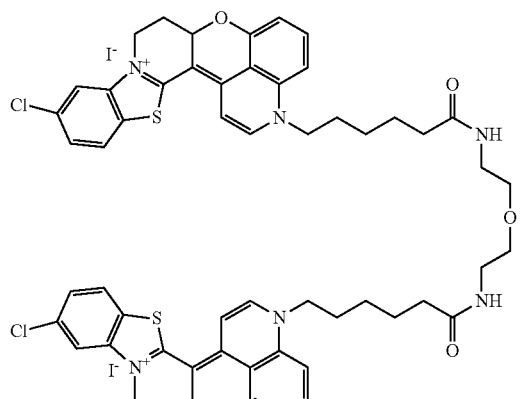
[Compound 6]
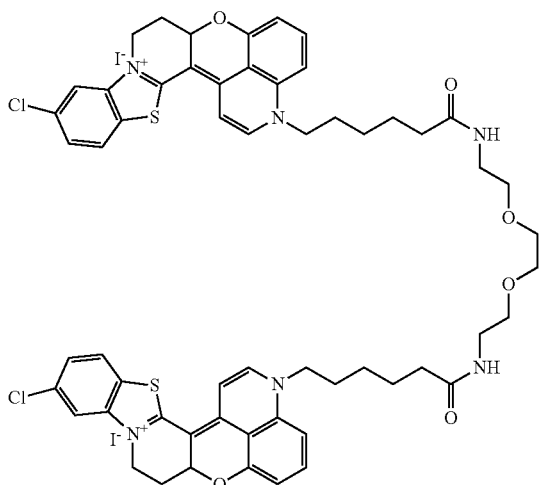
[Compound 7]
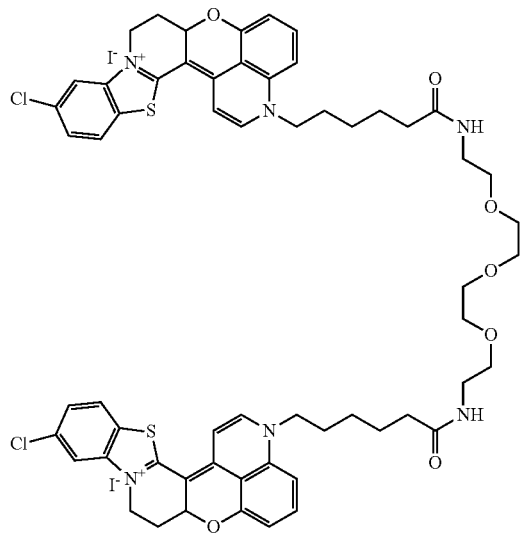
[Compound 8]
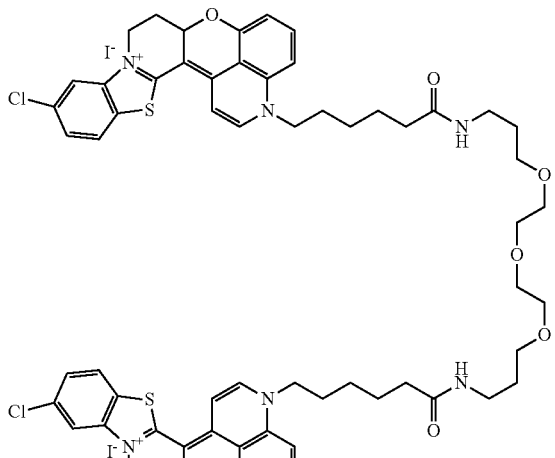

-continued
[Compound 9]
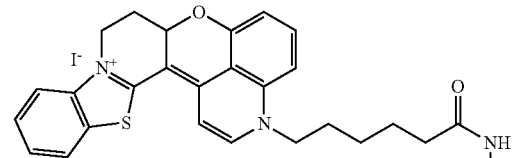
[Compound 10]
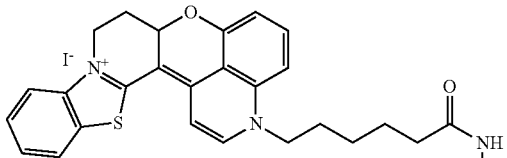
[Compound 11]
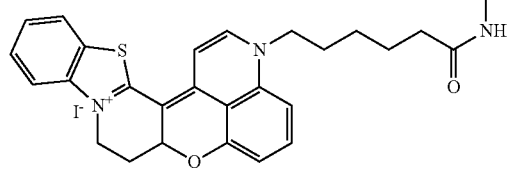
[Compound 12]
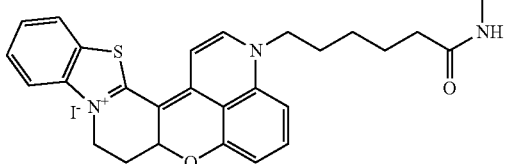
[Compound 13]
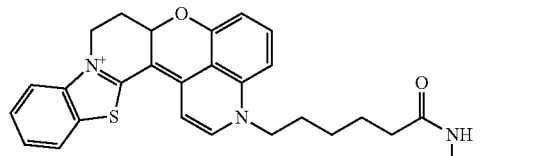
[Compound 14]
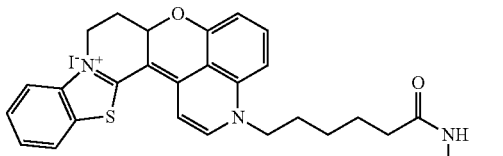

[Compound 15]
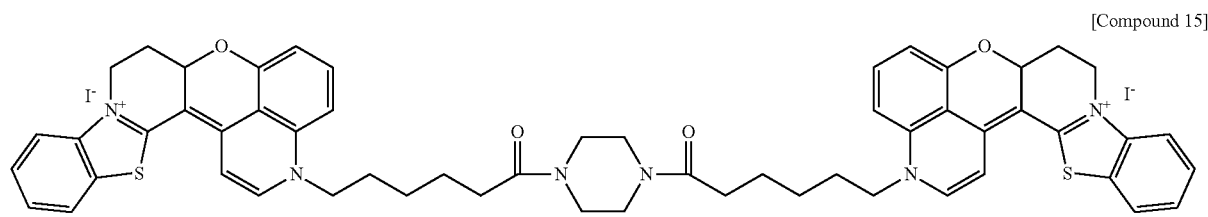
[Compound 16]
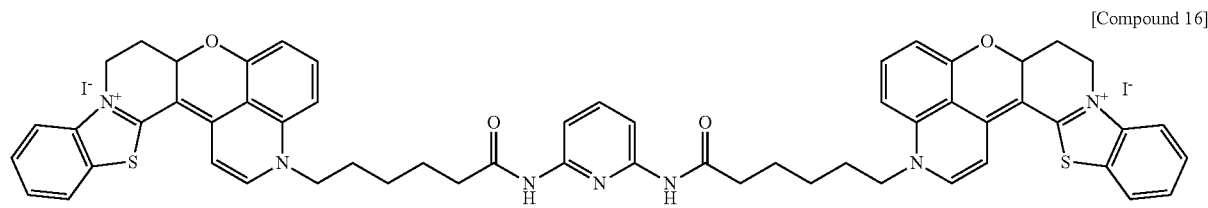
[Compound 17]
[Compound 18]
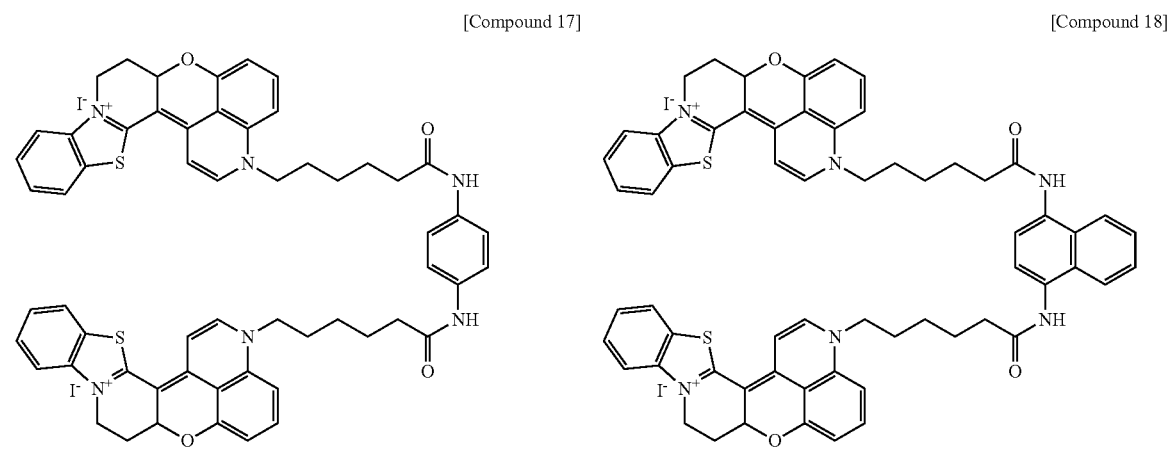
[Compound 19]
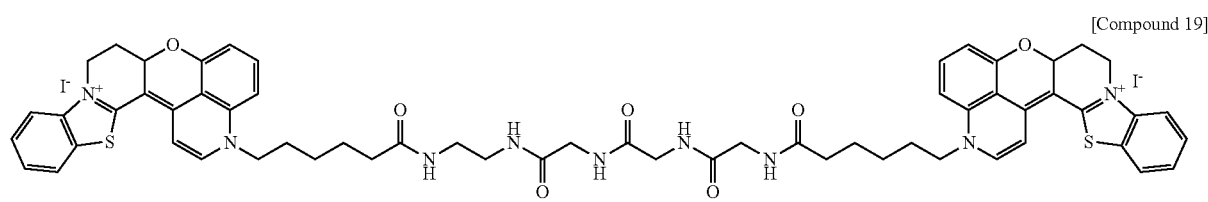
[Compound 20]
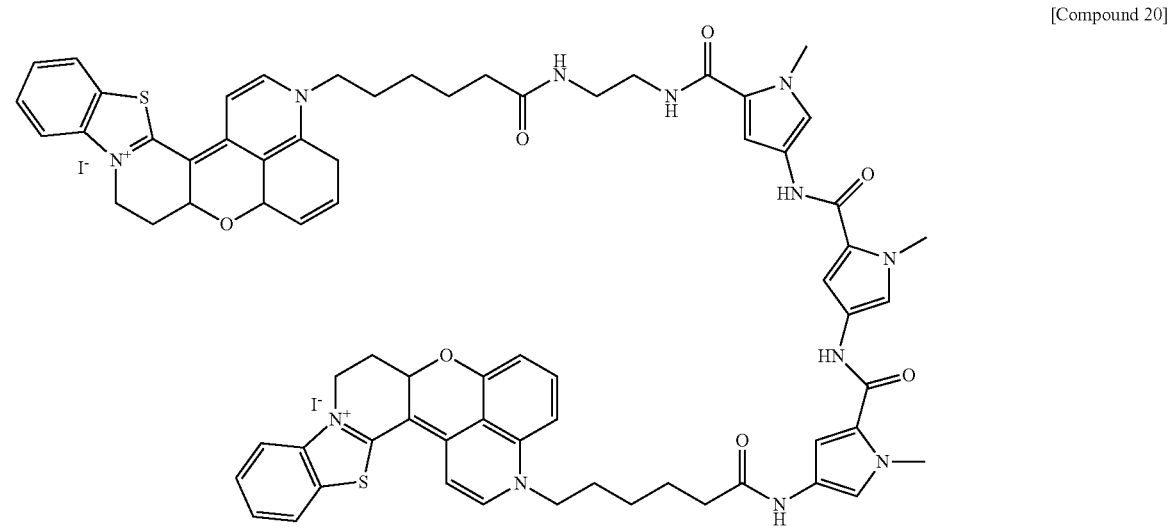

-continued
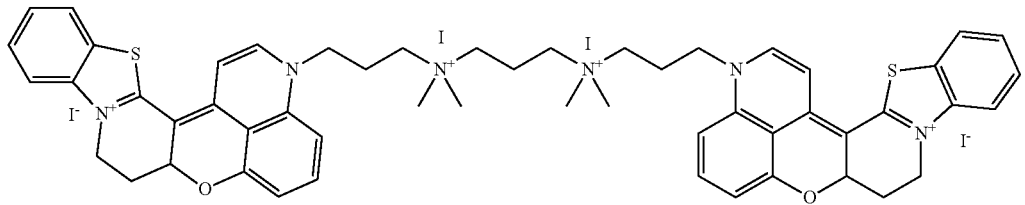
[Compound 21]
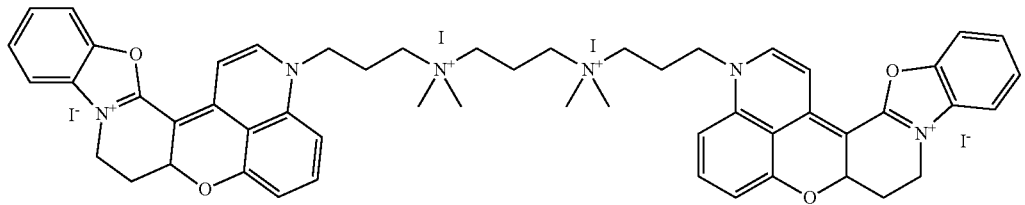
[Compound 22]
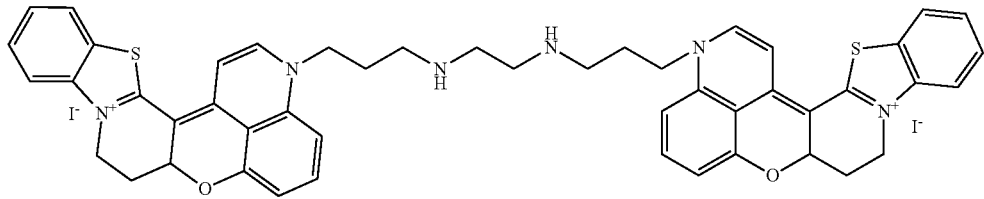
[Compound 23]
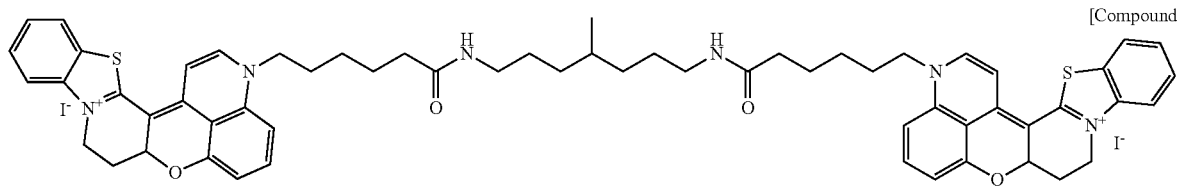
[Compound 24]
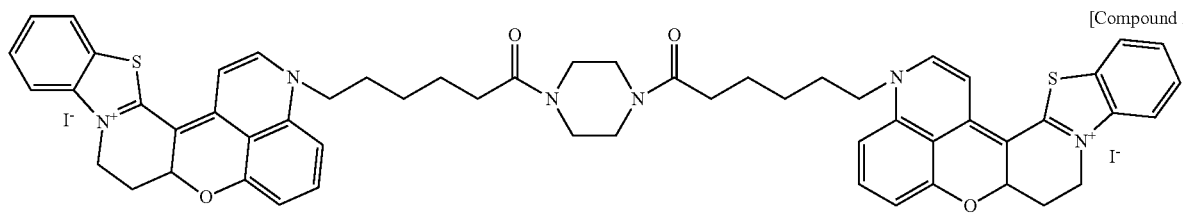
[Compound 25]
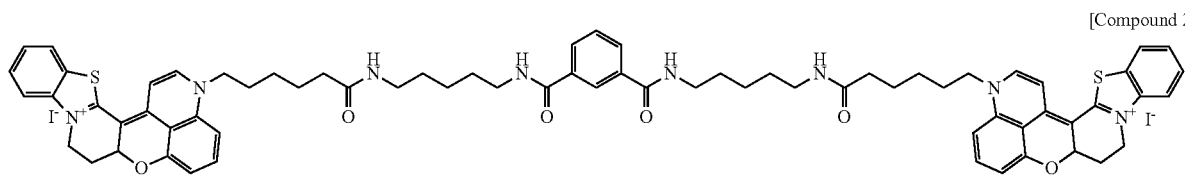
[Compound 26]

[Compound 27]
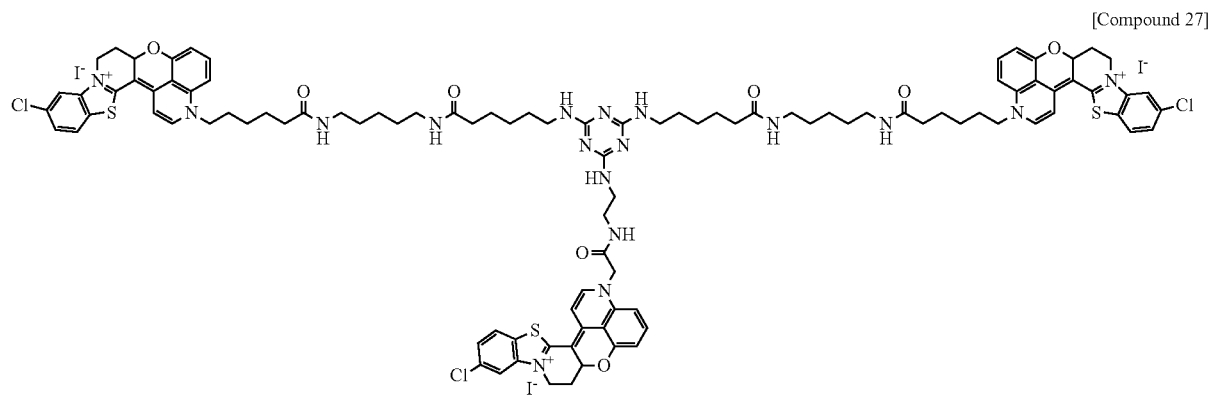
[Compound 28]
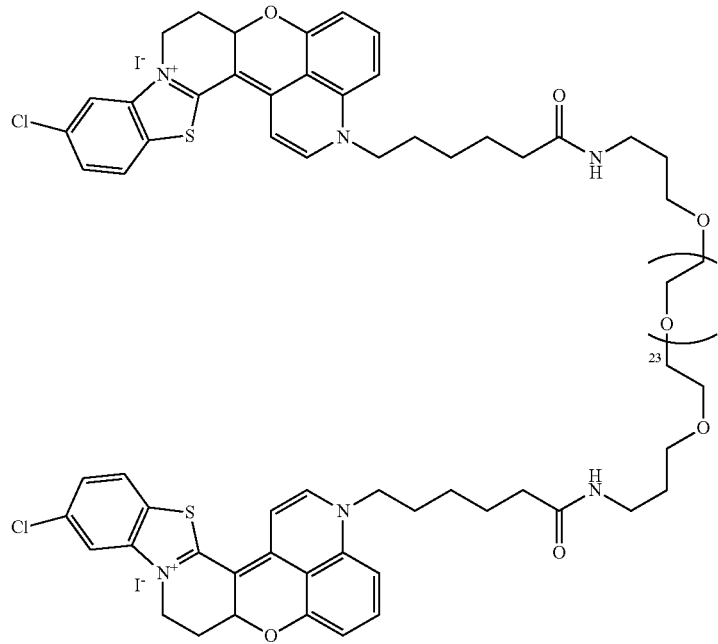
[Compound 29]
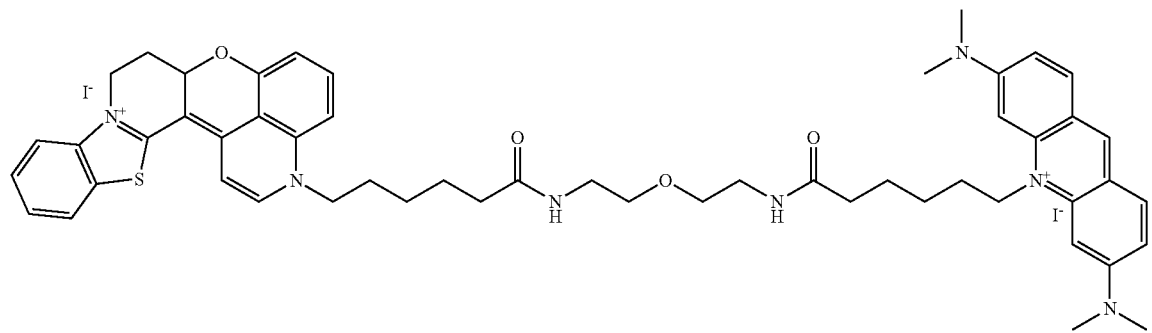

-continued
[Compound 30]
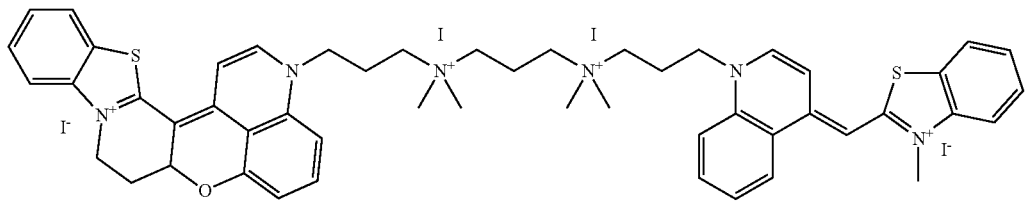
[Compound 31]
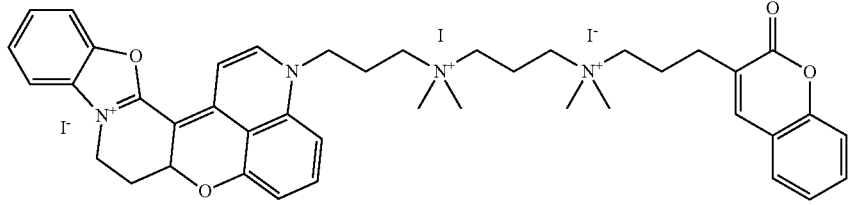
[Compound 32]
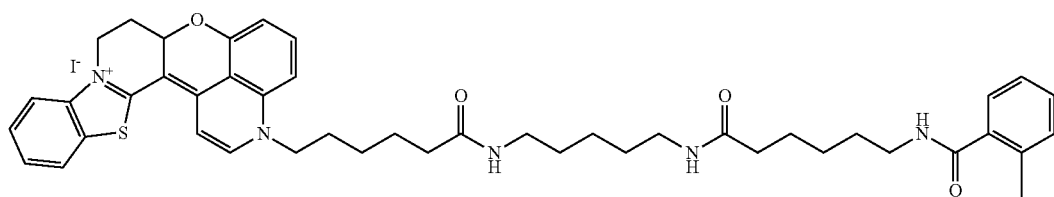
[Compound 33]
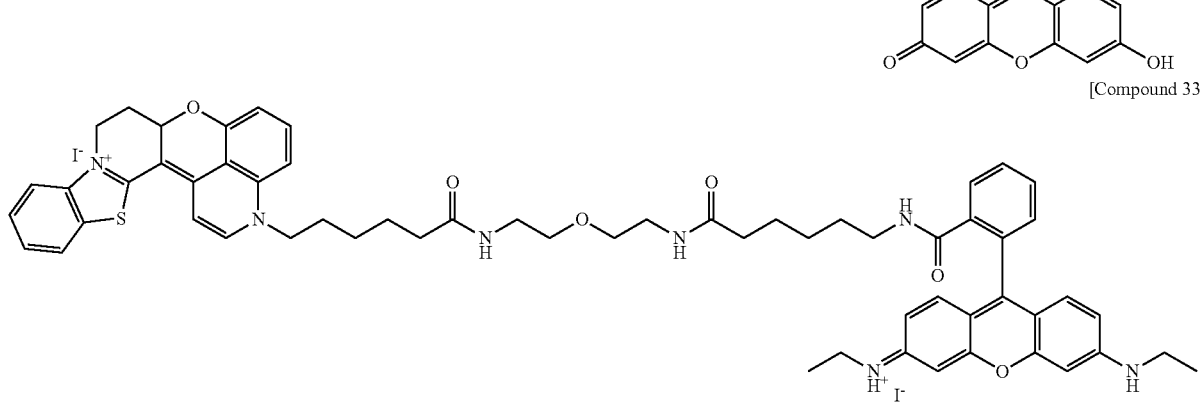
[Compound 34]
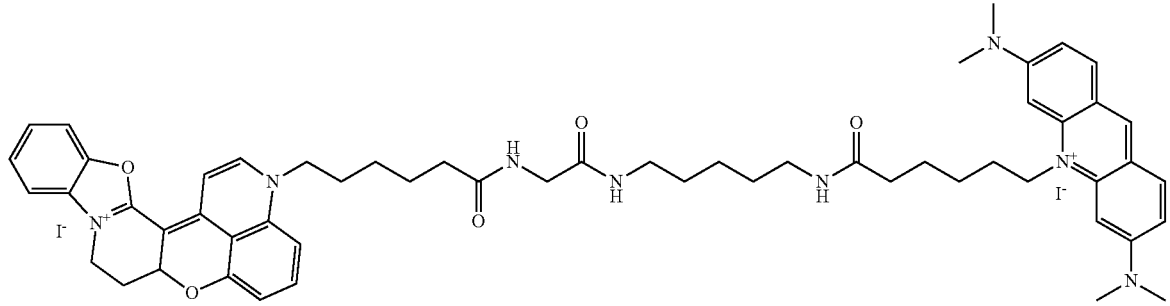
[Compound 35]
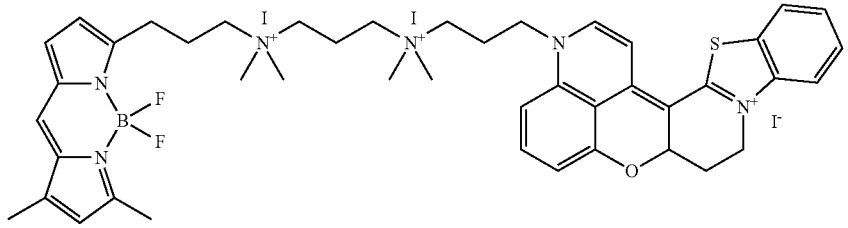

[Compound 36]

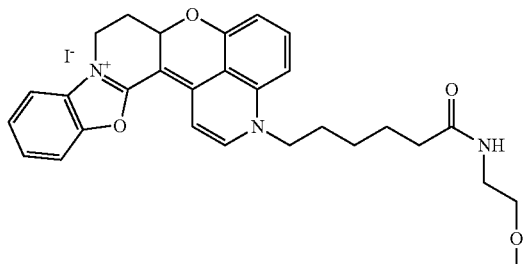

[Compound 37]

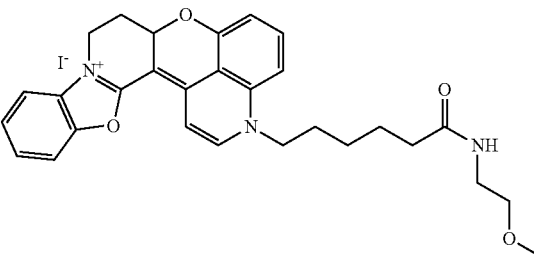

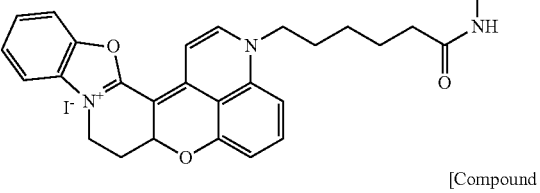

[Compound 38]

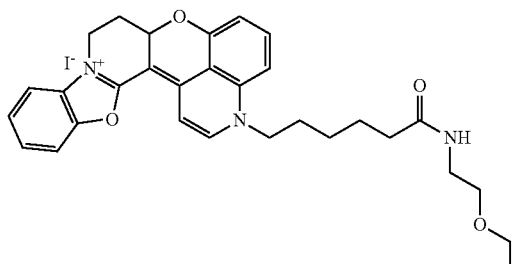

[Compound 39]

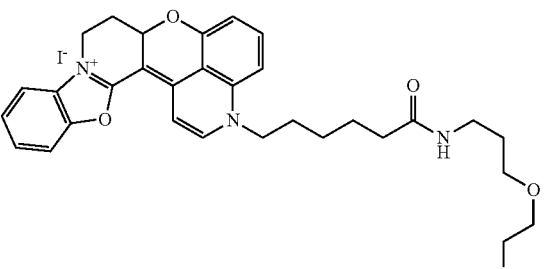

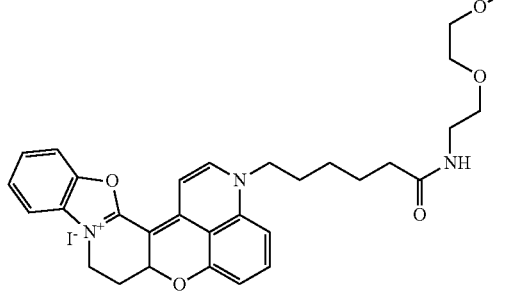

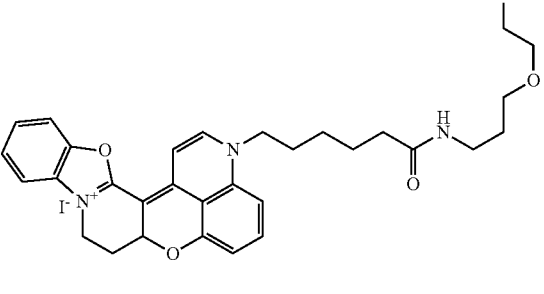

The target biomolecules of the merocyanine-based compound according to various embodiments of the present disclosure may be at least one selected from single-stranded RNA, double-stranded RNA, single-stranded DNA and double-stranded DNA, and the merocyanine-based compound can be intercalated into the nucleic acids.

Dyes, Kits and Contrast Medium Compositions for Labeling Biomolecules

According to another aspect of the present disclosure, there are provided a dye, kit and contrast medium composition for labeling biomolecules, comprising at least one selected from merocyanine-based compounds according to various embodiments of the present disclosure.

In addition, if necessary, the kit may further include an enzyme, a solvent (buffer solution, etc.), and other reagents for intercalating nucleic acid, which is a target biomolecule. The solvent is selected from the group consisting of a buffer selected from the group consisting of phosphate buffer, carbonate buffer and Tris buffer, an organic solvent selected from dimethylsulfoxide, dimethylformamide, dichloromethane, methanol, ethanol and acetonitrile, or water, and it is possible to control the solubility by introducing various functional groups into a cyanine-based compound depending on the type of solvent.

In a dye for labeling biomolecules according to an embodiment of the present disclosure, merocyanine-based compounds in the form of dimer and/or trimer may exist in a state of being coagulated with each other by an intermolecular interaction.

At this time, the merocyanine compounds in the form of dimer and/or trimer does not generate a fluorescence signal in an aggregated state. On the other hand, when biomolecules (for example, nucleic acids) are present, the merocyanine-based compounds can generate fluorescence signals as they are separated from each other and intercalated into nucleic acids.

That is, the presence or absence of an intercalatable biomolecule serves as a quencher of a dye for labeling a biomolecule according to an embodiment of the present disclosure.

For example, a kit according to an embodiment of the present disclosure can be provided as an electrophoresis kit configured to separate nucleic acids as a biomolecule by size, and then to label the nucleic acids as the merocyanine-based compound in a dye for labeling a biomolecule is intercalated into the nucleic acids.

Specifically, the electrophoresis kit may include at least one compound selected from merocyanine-based compounds according to various embodiments of the present disclosure, a buffer, a gel matrix, at least one material for forming a gel matrix, a surface, or at least one material for forming a surface, and the electrophoresis kit may be an electrophoresis kit for determining the presence or absence of a nucleic acid in a sample immobilized on the matrix or the surface when the nucleic acid is present in the sample.

The surface may be a solid surface, a film surface, a glass surface, a plastic surface, or a polysilicon surface. The matrix may be prepared from at least one selected from the group consisting of alginate, collagen, peptides, fibrin, hyaluronic acid, agarose, polyhydroxyethyl methacrylate, polyvinyl alcohol, polyethylene glycol, polyethylene oxide, polyethylene glycol diacrylate, gelatin, matrigel, polylactic acid, carboxymethylcellulose, dextran, chitosan, latex and sepharose, and may be in the form of beads or membranes.

In addition, the contrast medium composition according to the above embodiments may further include a pharmaceutically acceptable carrier besides the merocyanine-based compound according to various embodiments of the present disclosure to be administered orally or parenterally.

Specific examples of the pharmaceutically acceptable carrier include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate and mineral oil.

Hereinafter, a method for labeling a biomolecule using a dye for labeling a biomolecule or a kit for labeling a biomolecule described above will be described.

Method for Labeling a Biomolecule Using a Dye for Labeling a Biomolecule

The method of labeling a biomolecule with a merocyanine-based compound according to various embodiments of the present disclosure includes a labeling method of measuring the fluorescence of a labeled solid or semi-solid biomolecule, which is applicable to the labeling of all possible biomolecules.

By using the merocyanine-based compound instead of a conventional fluorescent dye, it is possible to provide a labeling method which is chemically stable with high sensitivity and excellent in operability.

According to various embodiments of the present disclosure, a method of labeling a biomolecule by intercalating a merocyanine-based compound into a target biomolecule can be implemented. It can also be used to quantify biomolecules in liquids or gels, and to stain biomolecules in living cells or apoptotic cells, and to detect and quantify biomolecules in microarrays.

Specifically, according to various embodiments of the present disclosure, the merocyanine-based compound can be used to determine the presence or absence of nucleic acid in a sample. More specifically, there may be a method of determining the presence or absence of nucleic acid in a sample, including, when a nucleic acid is present in a sample, exposing the nucleic acid to a merocyanine-based compound according to various embodiments of the present disclosure, and intercalating the merocyanine-based compound into the nucleic acid to form a complex; and determining the presence or absence of fluorescence of the merocyanine-based compound.

The merocyanine-based compound is chemically stable with high sensitivity and easily intercalated with a nucleic acid present in a sample to form a complex. Then, the formed complex is irradiated with light of a sufficient wavelength, and the presence or absence of the nucleic acid in the sample can easily be determined by an emitted fluorescence signal.

The fluorescence signal can be detected through various instruments such as a plate reader, a microscope, a fluorometer, a quantum counter and a flow cell sorter, or through naked eyes.

In addition, the presence or absence of an amplified target nucleic acid can be determined using the merocyanine-based compound.

Specifically, a method for performing a nucleic acid amplification reaction may include a method for determining the presence or absence of an amplified target nucleic acid, comprising: providing a reaction mixture comprising a target nucleic acid, a reagent necessary to amplify the target nucleic acid, and a merocyanine-based compound according to various embodiments of the present disclosure; subjecting the reaction mixture to polymerization under conditions suitable for the formation of the amplified target nucleic acid; illuminating the reaction mixture with light; and detecting a fluorescence emission from the reaction mixture.

The reaction mixture may include, in addition to the target nucleic acid, amplification enzymes, primers sufficient to amplify the target nucleic acid sequence, reagents such as deoxynucleoside triphosphate, and the like.

Since the merocyanine-based compound can be used without inhibiting a PCR reaction, it can be useful for determining the presence or absence of the amplified target nucleic acid.

In addition, the nucleic acid in the sample can be quantified using the merocyanine-based compound. Specifically, a method of quantifying a nucleic acid in a sample may include mixing a mixture comprising a merocyanine-based compound according to various embodiments of the present disclosure with a sample comprising a nucleic acid; incubating the sample and the mixture for a sufficient time to cause the merocyanine-based compound to intercalate with the nucleic acid in the sample to form a complex and generate a fluorescence signal; and comparing the fluorescence signal detected with fluorescence standard characteristics of a predetermined amount of nucleic acid to quantify the nucleic acid in the sample.

The amount of nucleic acid in the sample can be quantified relative to the fluorescence signal that is detected based on the fluorescent standard characteristics of a particular amount of nucleic acid.

A substantially primary relationship between the amount of nucleic acid and the fluorescence intensity may be used for the quantification of the nucleic acid or, if a cell extract is used, for cell number evaluation. In one example, the nucleic acid may be impregnated with an inert matrix such as a blot or gel, or attached to a solid surface such as a microarray chip or any other solid surface. This is done by applying a solution comprising a merocyanine-based compound onto the surface of a nucleic acid-containing matrix, or the surface of a microarray chip or other solid surface, and incubating for a sufficient time to form a dye-nucleic acid complex.

In addition, according to various embodiments of the present disclosure, a method of quantifying target cell viability and a target cell by way of intercalating a merocyanine-based compound into a biomolecule contained in a target cell may be implemented.

Specifically, a method of quantifying the viability of cells in a sample may include mixing a mixture comprising a merocyanine-based compound according to various embodiments of the present disclosure with a sample comprising apoptotic cells; incubating the sample and the mixture for a sufficient time to cause the merocyanine-based compound to intercalate into the apoptotic cells in the sample to form a complex and generate a fluorescence signal; and comparing the fluorescence signal detected with fluorescence standard characteristics of a predetermined amount of apoptotic cells to quantify the apoptotic cells in the sample.

According to one embodiment of the present disclosure, the merocyanine-based compound may not penetrate living cells, but penetrate apoptotic cells. Using such a characteristic, the merocyanine-based compound can be incubated for a sufficient time to pass through a membrane of the apoptotic cells and form a complex with the nucleic acid in the membrane.

In another embodiment, a method for analyzing the viability of a cell in a sample may be provided, the method including: mixing a merocyanine-based compound according to various embodiments of the present disclosure capable of intercalating with apoptotic cells, an aqueous solution containing a compound other than the merocyanine-based compound capable of intercalating with cells, and a sample comprising cells; light-illuminating a sample comprising the cells that are intercalated with the merocyanine-based compound and the other compound; and detecting fluorescence emission from the sample, wherein the fluorescence emitted from the sample is generated by intercalating with the cells in the sample together with the merocyanine-based compound and the other compound, resulting in a fluorescence reaction between the cells, and the emitted fluorescence may be different from the fluorescence generated by a fluorescent reaction of the merocyanine-based compound alone.

According to one embodiment of the present disclosure, the merocyanine-based compound can intercalate with apoptotic cells. Specifically, the merocyanine-based compound can penetrate apoptotic cells and intercalate with nucleic acids in the apoptotic cells.

On the other hand, a compound other than the above merocyanine-based compound, for example, acridine orange (AO) can intercalate with living cells as well as apoptotic cells. In other words, acridine orange (AO) can intercalate with intracellular nucleic acid through the membrane of living cells as well as apoptotic cells.

The fluorescence signal generated from a complex formed by intercalation of a nucleic acid and a compound other than the merocyanine-based compound and the merocyanine-based compound can be measured to analyze the viability of cells in the sample. Specifically, the viability of cells can be analyzed by measuring and distinguishing the wavelength of the fluorescence signal generated by a complex of the merocyanine-based compound and the nucleic acid and the fluorescence signal generated by a complex of the other compound and the nucleic acid.

In addition, the present disclosure can be a kit for analyzing the viability of cells in a sample using the above-described characteristics.

Specifically, the present disclosure may be a kit for analyzing the viability of cells in a sample, such that it comprises a merocyanine-based compound according to various embodiments of the present disclosure, and when the apoptotic cells are present in the sample, the fluorescence is detected by intercalating with the merocyanine-based compound.

Further, a method of identifying a biomolecule labeled with a merocyanine-based compound through electrophoresis can be implemented.

DNA Microarray Method

In the DNA microarray method, a dye is reacted with a target nucleic acid to be labeled (that is, a merocyanine-based compound is intercalated into a target nucleic acid), wherein a fluorescence signal can be generated by preparing a single-stranded probe nucleic acid having a base sequence complementary to the target nucleic acid, hybridizing the single-stranded target nucleic acid and the probe nucleic acid on a substrate, and then intercalating a fluorescent dye into the target nucleic acid.

In the present labeling method, the probe nucleic acid immobilized on a substrate can be prepared by PCR amplification using a library of cDNA such as cDNA, a library of genomes, or all genomes as a template in the case of examining gene expression.

Further, in the case of examining a mutation or the like of a gene, it is possible to use a synthesized oligonucleotide corresponding to a mutation based on a known standardized sequence.

The method of immobilizing the probe nucleic acid on a substrate can be appropriately selected depending on the kind of the nucleic acid and the type of the substrate. For example, a method of electrostatic bonding to a substrate surface-treated with a cation such as polylysine using the charge of DNA may be used.

PCR Method

In the PCR method, the probe complementary to a base sequence of a target nucleic acid to be labeled is labeled with a dye, and the target nucleic acid is reacted with the probe before or after the amplification of the target nucleic acid, and the fluorescence of the target nucleic acid is measured.

More specifically, the elongation reaction of the target nucleic acid is carried out by an enzyme (DNA polymerase, RNA polymerase). In this case, a double-stranded nucleic acid sequence formed by a primer consisting of the target nucleic acid and an oligonucleotide is recognized by the enzyme, and an elongation reaction is carried out from the recognized position, and only the desired gene region is amplified.

When the enzyme is synthesized, a synthesis reaction is carried out using a nucleotide (dNTP, NTP) as a raw material.

At this time, when a nucleotide having a dye in a normal nucleotide (dNTP, NTP) is mixed at any ratio, a nucleic acid into which the dye has been introduced in said ratio can be synthesized.

It is also possible to introduce a nucleotide having an amino group at any ratio by PCR, and then bind a labeling dye to synthesize a nucleic acid into which the labeling dye has been introduced.

When the enzyme is synthesized, the synthesis reaction is carried out using the nucleotide as a raw material. At this time, when the OH of 3' of the nucleotide is replaced with H, the elongation reaction of the nucleic acid is no longer achieved, and the reaction is terminated at that point.

This nucleotide, ddNTP (dideoxy nucleotide triphospate), is called a terminator.

When a nucleic acid is synthesized by adding a terminator to a normal nucleotide, a terminator is introduced at a certain probability to terminate the reaction. Thus, nucleic acids having various lengths are synthesized.

When it is size-separated by gel electrophoresis, DNA is lined up in order of length. Here, if each kind of the terminator is labeled with another labeling dye, a tendency to depend on each base is observed at the end point (3' terminal) of the synthesis reaction, such that the nucleotide sequence information of the target nucleic acid can be obtained by reading fluorescence information from the labeling dye labeled on the terminator.

Alternatively, instead of the terminator, a primer labeled with a labeling dye may be used to hybridize with the target nucleic acid.

PNA (peptide nucleic acid) may also be used as a probe. PNA is a substitution of the pentane/phosphate skeleton, which is a basic skeletal structure of nucleic acid, with the polyamide skeleton of glycine. PNA has a three-dimensional structure that resembles the nucleic acids, and binds very specifically and strongly to the nucleic acids with complementary nucleotide sequences. Thus, it can be used as a reagent for telomere studies by applying it to a telomere PNA probe as well as a conventional DNA analysis method such as in-situ hybridization (ISH) method.

The labeling may proceed, for example, by hybridizing double-stranded DNA with PNA labeled with a labeling dye having a base sequence complementary to all or a part of the base sequence of DNA, heating the mixture to produce single-stranded DNA, slowly cooling the mixture to room temperature to prepare a PNA-DNA complex, and measuring fluorescence.

In the above embodiment, the method of measuring the fluorescence of the product by amplifying the target nucleic acid by the PCR method has been described, but, in this method, it is necessary to check the size of the product by electrophoresis, and then measure the amount of the amplification product by measuring the fluorescence intensity.

For this purpose, it is also possible to measure the amount of the product in real time using a probe designed to generate fluorescence by using an energy transfer of the fluorescent dye and hybridizing it with the product of the PCR method.

For example, donor and acceptor-labeled DNA can be used. Specific labeling methods include a molecular beacon method, a TaqMan-PCR method, a cycling probe method, etc., which confirm the presence of a nucleic acid having a specific sequence.

Other Labeling Methods

Further, intracellular signaling phenomenon can be observed by using the labeling dye of the present disclosure. Various enzymes are involved in internal signaling or cell reaction. In a typical signaling phenomenon, it is known that a specific protein kinase is activated, thereby inducing protein phosphorylation and initiating signaling.

Binding and hydrolysis of nucleotides (for example, ATP or ADP) play a critical role in their activity, and intracellular signaling can be observed with high sensitivity by introducing a labeling dye into nucleotide derivatives.

In addition, the labeling dye of the present disclosure can be used for observation of gene expression phenomenon using RNA interference (RNAi).

RNAi is a method of degrading mRNA of a target gene by introducing double-stranded RNA (dsRNA) into a cell, thereby suppressing the expression. It is possible to observe the RNAi phenomenon by labeling the designed dsRNA with a labeling dye.

RNAi can break down the mRNA of the target gene and inhibit its expression by introducing double-stranded RNA (dsRNA) into cells, and RNAi phenomenon can be observed by labeling the designed dsRNA with labeling dye.

Hereinafter, specific examples of the present disclosure will be described. However, these examples described below are only intended to illustrate or explain the present disclosure, and thus the present disclosure should not be limited thereto.

PREPARATION EXAMPLES

Preparation Example 1

Synthesis of Compound 1

(1) Synthesis of Intermediate 1 and Intermediate 2

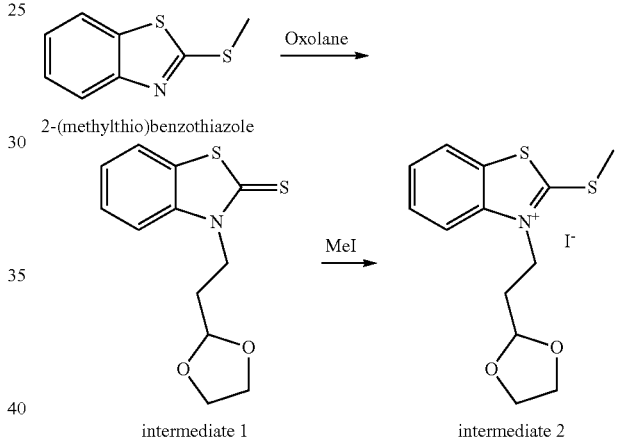

2-(methylthio)benzothiazole (11.115 g, 0.0614 mol) and acetonitrile (110 mL) were added to a 250 mL single-neck reactor, and the mixture was stirred at room temperature for 5 minutes. Then, oxolane, i.e., 2-iodoethyl-1,3-dioxolane (21 g, 0.0921 mol) was added to the reactor, and the mixture was stirred under reflux for 40 hours, cooled, concentrated, and then purified by column to obtain Intermediate 1 (14 g, 0.0523 mol, 85%). $^1$H-NMR (400 MHz, CDCl$_3$) δ 7.45-7.48 (m, 1H), 7.38-7.43 (m, 1H), 7.26-7.32 (m, 2H), 5.00 (t, J=4.0 Hz, 1H), 4.54-4.58 (m, 2H), 3.89-4.02 (m, 4H), 2.18-2.23 (m, 2H).

Subsequently, Intermediate 1 (2.37 g, 0.01 mol) and acetonitrile (30 mL) were added to a 100 mL single-neck reactor, and the mixture was stirred at room temperature for 5 minutes. To the reactor was added methyl iodide (MeI) (1.26 g, 0.03 mol), and the mixture was stirred under reflux for 12 hours, cooled, concentrated, and ethyl acetate (50 mL) was added to precipitate a solid. The precipitated solid was filtered and vacuum dried to give Intermediate 2 (3 g, 0.00733 mol, 73%). $^1$H-NMR (400 MHz, CDCl$_3$) δ 8.51 (d, J=8.0 Hz, 1H), 7.92 (d, J=8.4 Hz, 1H), 7.76 (t, J=8.4 Hz, 1H), 7.64 (t, J=8.0H, 1H), 5.03 (t, J=3.6 Hz, 1H), 4.78 (t, J=7.2 Hz, 2H), 3.84-4.00 (m, 2H), 3.21 (s, 3H), 2.38-2.42 (m, 2H).

(2) Synthesis of Intermediate 3

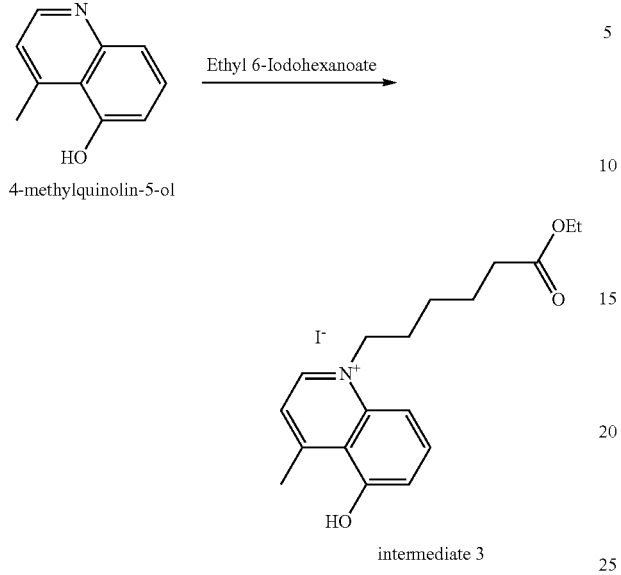

4-methyl-5-quinolinol (2 g, 0.0125 mol), ethyl 6-iodohexanoate (10 g, 0.0375 mol) and dimethylformamide (4 mL) were placed in a 50 mL single-neck reactor, and the mixture was stirred for 12 hours, cooled, concentrated, and purified by column to give Intermediate 3 (3.5 g, 0.00828 mol, 67%). $^1$H-NMR (400 MHz, DMSO-d$_6$) δ 9.19 (d, J=6.4 Hz, 1H), 7.952 (t, J=8.0 Hz, 1H), 7.73-7.77 (m, 2H), 7.22 (d, J=7.6 Hz, 1H), 4.85 (t, J=6.8 Hz, 2H), 4.01 (q, J=7.6 Hz, 2H), 3.09 (s, 3H), 2.35 (t, J=7.6 Hz, 2H), 1.89-1.93 (m, 2H), 1.55-1.61 (m, 4H), 1.12 (t, J=6.8 Hz, 3H).

(3) Synthesis of Intermediate 4

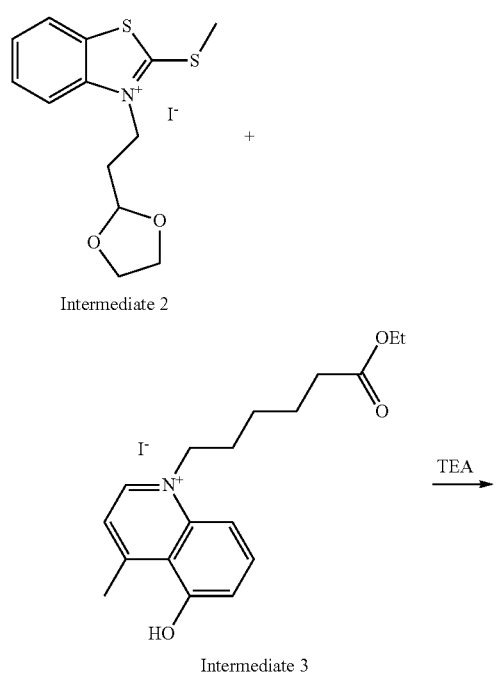

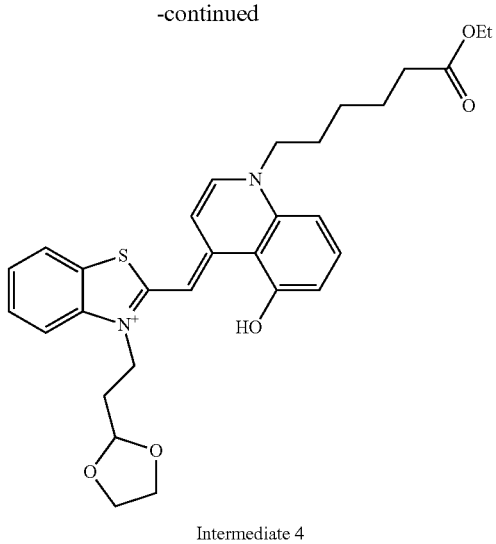

Intermediate 2 (1.55 g, 3.814 mmol), Intermediate 3 (1.64 g, 3.814 mmol) and dichloromethane (30 mL) were added to a 100 mL single-necked reactor, and the mixture was stirred at room temperature for 5 minutes. Then, triethylamine (1.15 g, 11.442 mmol) was added to the reactor, followed by stirring at room temperature for 12 hours, and then concentrated and purified by column to obtain Intermediate 4 (1.5 g, 2.263 mmol, 59%).

(4) Synthesis of Intermediate 5

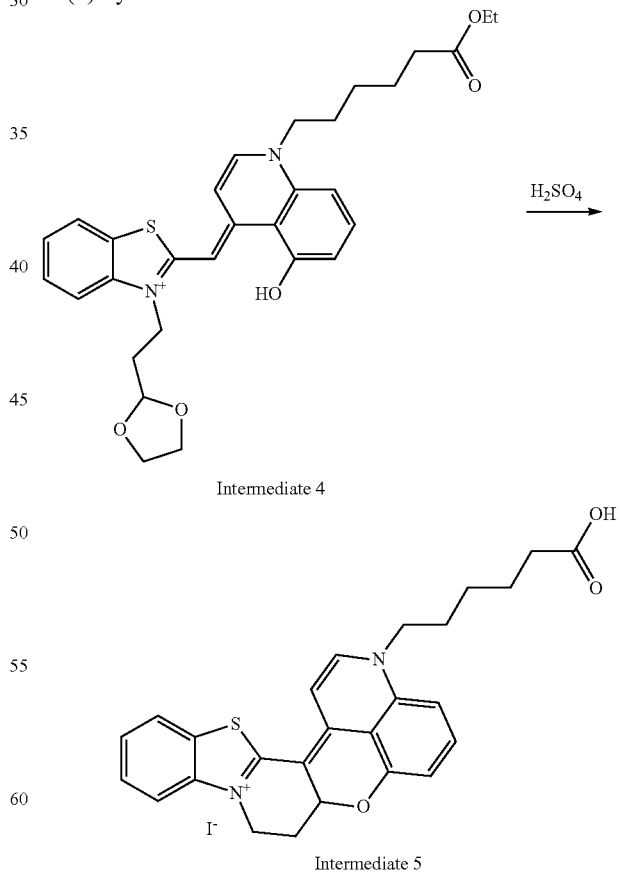

Intermediate 4 (1.5 g, 2.263 mmol) and chloroform (45 mL) were added to a 250 mL single-necked reactor and stirred at room temperature for 5 minutes. 50% aqueous sulfuric acid solution (9 mL) was then added to the reactor and stirred for 12 hours. Subsequently, water (10 mL) was added to the reactor, and the mixture was extracted with dichloromethane (2×50 mL). The organic layer was concentrated and purified by column to obtain Intermediate 5 (0.4 g, 0.666 mmol, 29%). $^1$H-NMR (400 MHz, MeOD) δ 8.35 (d, J=7.2 Hz, 1H), 7.91 (d, J=8.0 Hz, 1H), 7.82 (t, J=8.0 Hz, 1H), 7.62-7.65 (m, 2H), 7.54 (d, J=8.8 Hz, 1H), 7.42-7.44 (m, 1H), 7.36 (d, J=7.2 Hz, 1H), 7.11 (d, J=8.0 Hz, 1H), 5.21-5.25 (m, 1H), 4.70-4.75 (m, 1H), 4.45-4.60 (m, 2H), 4.13-4.20 (m, 1H), 2.87-2.92 (m, 1H), 2.52-2.56 (m, 1H), 2.33 (t, J=7.6 Hz, 2H), 1.94-2.02 (m, 2H), 1.66-1.73 (m, 2H), 1.46-1.52 (m, 2H).

(5) Synthesis of Compound 1

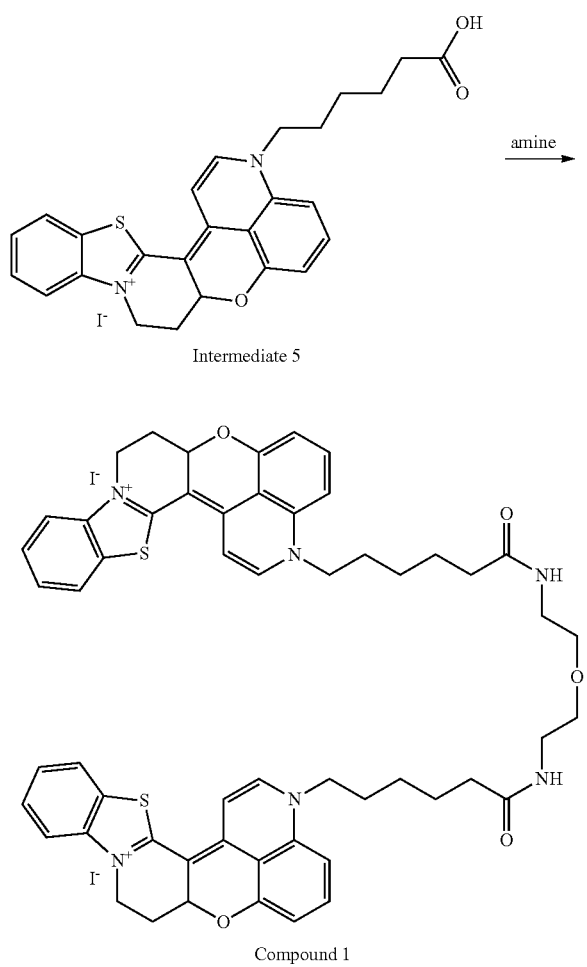 [SMILES: O=C(O)CCCCCN1C=CC2=C3c4sc5ccccc5[n+]4CCC3Oc3cccc1c32 ; [I-] ; "amine" ; O=C(CCCCCN1C=CC2=C3c4sc5ccccc5[n+]4CCC3Oc3cccc1c32)NCCOCCNC(=O)CCCCCN1C=CC2=C3c4sc5ccccc5[n+]4CCC3Oc3cccc1c32 ; [I-] ; [I-]]

Intermediate 5

Compound 1

Intermediate 5 (200 mg, 0.35 mmol) and dimethylformamide (4 mL) were added to a 250 mL single-neck reactor and stirred for 5 minutes at room temperature. TSTU (106 mg, 0.35 mmol) and triethylamine (50 μL, 0.35 mmol) were then added to the reactor, followed by stirring at room temperature for 15 minutes. Then, triethylamine (50 μL, 0.35 mmol) and 2,2'-oxybisethylamine (13 μL, 0.119 mmol) were added to the reactor. The mixture was stirred at room temperature for 3 days and poured into ethyl acetate (40 mL) to precipitate a solid. The precipitated solid was filtered and purified by column to obtain Compound 1 (110 mg, 0.0906 mmol, 26%). $^1$H-NMR (400 MHz, MeOD) δ 8.25 (d, J=6.8 Hz, 2H), 7.77-7.80 (m, 2H), 7.68-7.73 (m, 2H), 7.51-7.54 (m, 4H), 7.41 (t, 2H, J=8.8 Hz, 2H), 7.29-7.35 (m, 2H), 7.16-7.20 (m, 2H), 7.01 (d, J=7.6 Hz, 2H), 5.04-5.11 (m, 2H), 4.60-4.63 (m, 2H), 4.32-4.43 (m, 4H), 4.00-4.09 (m, 2H), 3.44-3.47 (m, 4H), 3.30-3.32 (m, 4H), 2.79-2.82 (m, 2H), 2.35-2.45 (m, 2H), 2.21 (t, J=7.2 Hz, 4H), 1.85-1.92 (m, 4H), 1.61-1.69 (m, 4H), 1.39-1.45 (m, 4H).

Preparation Example 2

Synthesis of Compound 2 to Compound 4

Compound 2, Compound 3 and Compound 4 were synthesized in the same manner as in the synthesis of Compound 1 from Intermediate 5 of Preparation Example 1, except that 4,7,10-trioxa-1,13-tridecane diamine, 1,2-bis(2-aminoethoxy)ethane, and 1,11-diamino-3,6,9-trioxaundecane were used instead of 2,2'-oxybisethylamine, respectively.

Compound 2—$^1$H-NMR (400 MHz, MeOD) δ 8.25 (d, J=7.2 Hz, 2H), 7.77 (t, J=8.0 Hz, 2H), 7.69-7.73 (m, 2H), 7.50-7.55 (m, 4H), 7.41 (t, J=8.4 Hz, 2H), 7.30-7.32 (m, 2H), 7.17-7.20 (m, 2H), 7.01 (d, J=8.0 Hz, 2H), 5.05-5.10 (m, 2H), 4.60-4.63 (m, 2H), 4.34-4.45 (m, 4H), 4.04-4.10 (m, 2H), 3.54-3.56 (m, 4H), 3.48-3.50 (m, 4H), 3.42 (t, J=6.0 Hz, 4H), 3.18 (t, J=6.8 Hz, 4H), 2.79-2.83 (m, 2H), 2.37-2.44 (m, 2H), 2.16 (t, J=6.8 Hz, 4H), 1.85-1.92 (m, 4H), 1.60-1.70 (m, 8H), 1.37-1.42 (m, 4H).

Compound 3—$^1$H-NMR (400 MHz, MeOD) δ 8.26 (d, J=8.0 Hz, 2H), 7.77-7.79 (m, 2H), 7.69-7.72 (m, 2H), 7.52-7.54 (m, 4H), 7.42 (t, J=8.4 Hz, 2H), 7.31-7.33 (m, 2H), 7.17-7.20 (m, 2H), 7.02 (d, J=7.6 Hz, 2H), 5.05-5.12 (m, 2H), 4.60-4.64 (m, 2H), 4.33-4.43 (m, 4H), 4.01-4.10 (m, 2H), 3.54-3.57 (m, 4H), 3.50 (t, J=6.4 Hz, 4H), 3.32 (t, J=6.4 Hz, 4H), 2.80-2.83 (m, 2H), 2.40-2.43 (m, 2H), 2.21 (t, J=7.2 Hz, 4H), 1.86-1.92 (m, 4H), 1.63-1.68 (m, 4H), 1.42-1.46 (m, 4H).

Compound 4—$^1$H-NMR (400 MHz, MeOD) δ 8.27 (d, J=7.2 Hz, 2H), 7.77-7.80 (m, 2H), 7.69-7.73 (m, 2H), 7.52-7.54 (m, 4H), 7.42 (t, J=8.4 Hz, 2H), 7.31-7.33 (m, 2H), 7.18-7.20 (m, 2H), 7.02 (m, J=7.6 Hz, 2H), 5.06-5.11 (m, 2H), 4.60-4.64 (m, 2H), 4.35-4.44 (m, 4H), 4.05-4.08 (m, 2H), 3.54-3.58 (m, 8H), 3.48 (t, J=6.0 Hz, 4H), 3.32 (t, J=4.8 Hz, 4H), 2.80-2.84 (m, 2H), 2.39-2.43 (m, 2H), 2.21 (t, J=7.2 Hz, 4H), 1.87-1.94 (m, 4H), 1.63-1.40 (m, 4H), 1.40-1.46 (m, 4H).

Preparation Example 3

Synthesis of Compound 5

Preparation Example 3 was synthesized in the same manner as in Preparation Example 1, except that 5-chloro-2-methylthiobenzothiazole was used instead of 2-methylthiobenzothiazole in the production of Intermediate 1 of Preparation Example 1. $^1$H-NMR (400 MHz, MeOD) δ 8.34 (d, J=6.4 Hz, 2H), 7.71-7.77 (m, 4H), 7.58 (m, 2H) 7.46 (t, J=8.4 Hz, 2H), 7.27 (t, J=7.2 Hz, 2H), 7.20 (t, J=6.8 Hz, 2H), 7.05 (d, J=7.6 Hz, 2H), 5.07 (m, 2H), 4.55-4.58 (m, 2H), 4.41 (m, 4H), 400-4.03 (m, 2H), 3.46 (m, 4H), 3.29 (m, 4H), 2.82 (m, 2H), 2.40-2.42 (m, 2H), 2.21 (m, 4H), 1.90 (m, 4H), 1.65 (m, 4H), 1.41 (m, 4H).

Preparation Example 4

Synthesis of Compound 6 to Compound 8

Compound 6, Compound 7 and Compound 8 were synthesized in the same manner as in the synthesis of Compound 1 from Intermediate 5 of Preparation Example 3, except that 1,2-bis (2-aminoethoxy) ethane, 1,11-dimino-3,6,9-trioxaundecane, and 4,7,10-trioxa-1,13-tridecanediamine were used instead of 2,2'-oxybisethylamine, respectively.

Compound 6—$^1$H-NMR (400 MHz, MeOD) δ 8.33-8.36 (m, 2H), 7.74-7.78 (m, 4H), 7.62-7.64 (m, 2H), 7.46-7.51 (m, 2H), 7.30-7.34 (m, 2H), 7.25 (t, J=7.6 Hz, 2H), 7.05-7.07 (m, 2H), 5.09-5.12 (m, 2H), 4.50-4.61 (m, 2H), 4.42-4.47 (m, 4H), 4.01-4.05 (m, 2H), 3.54 (m, 4H), 3.46-3.48 (m, 4H), 3.29 (m, 4H), 2.80-2.82 (m, 2H), 2.41-2.45 (m, 2H), 2.17-2.20 (m, 4H), 1.89-1.92 (m, 4H), 1.62-1.66 (m, 4H), 1.40-1.42 (m, 4H).

Compound 8—$^1$H-NMR (400 MHz, MeOD) δ 8.36-8.38 (m, 2H), 7.75-7.82 (m, 4H), 7.62-7.65 (m, 2H), 7.49-7.54 (m, 2H), 7.30-7.34 (m, 2H), 7.27 (t, J=7.2 Hz, 2H), 7.08-7.10 (m, 2H), 5.11-5.17 (m, 2H), 4.60-4.63 (m, 2H), 4.44-4.53 (m, 4H), 4.05-4.08 (m, 2H'), 3.56-3.59 (m, 4H), 3.50-3.53 (m, 4H), 3.45 (t, J=6.0 Hz, 4H), 3.20 (t, J=6.8 Hz, 4H), 2.82-2.84 (m, 2H), 2.44-2.49 (m, 2H), 2.19 (t, J=6.4 Hz, 4H), 1.90-1.97 (m, 4H), 1.63-1.72 (m, 8H), 1.40-1.65 (m, 4H).

Absorption spectra ($\lambda_{abs}$), emission spectra ($\lambda_{em}$), molar extinction coefficient (ε) and quantum efficiency of compounds 1 to 8 obtained in Preparation Examples 1 to 4, and commercially available SYBR® safe were measured and shown in Table 1 below.

TABLE 1

| Classification | sovent | $\lambda_{abs}$(nm) | $\lambda_{em}$(nm) | ε(M$^{-1}$cm$^{-1}$) | Quantum efficiency |
|---|---|---|---|---|---|
| SYBR ® safe | buffer | 502 | ND | 57,000 | 0.006 |
| | DMSO | 509 | ND | 77,000 | 0.006 |
| Compound 1 | buffer | 484 | 568 | 92,000 | 0.03 |
| | DMSO | 517 | 567 | 109,000 | 0.52 |
| Compound 2 | buffer | 484 | 565 | 83,000 | 0.08 |
| | DMSO | 517 | 566 | 101,000 | 0.88 |
| Compound 3 | buffer | 484 | 564 | 66,000 | 0.03 |
| | DMSO | 517 | 565 | 84,000 | 0.55 |
| Compound 4 | buffer | 484 | 566 | 85,000 | 0.03 |
| | DMSO | 517 | 565 | 95,000 | 0.73 |
| Compound 5 | buffer | 484 | 562 | 60,000 | 0.05 |
| | DMSO | 517 | 564 | 73,000 | 0.64 |
| Compound 6 | buffer | 484 | 564 | 60,000 | 0.04 |
| | DMSO | 517 | 563 | 70,000 | 0.62 |
| Compound 7 | buffer | 484 | 560 | 75,000 | 0.06 |
| | DMSO | 517 | 563 | 83,000 | 0.64 |
| Compound 8 | buffer | 484 | 565 | 78,000 | 0.04 |
| | DMSO | 517 | 563 | 89,000 | 0.71 |

It can be seen that Compounds 1 to 8 obtained in Preparation Examples 1 to 4 exhibited similar or superior molar extinction coefficients to SYBR® safe and were remarkably excellent in terms of quantum efficiency.

Preparation Example 5

Synthesis of Compound 9 to Compound 20

Compounds 9 to 13 were synthesized in the same manner as in the synthesis of Compound 1 from Intermediate 5 of Preparation Example 1, except that 1,6-diaminoheptane, 1,8-diaminooctane, 1,10-diaminodecane, 1,12-diaminododecane, 3,3-diamino-N-methyl dipropylamine were used instead of 2,2'-oxybisethylamine, respectively.

Compound 14 was synthesized as in the synthesis of Compound 1 from Intermediate 5 of Preparation Example 1, except that an amine bridge represented by the following formula was used instead of 2,2'-oxybisethylamine.

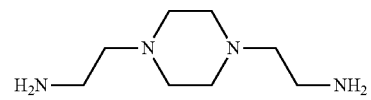

Compound 15 to Compound 18 were synthesized as in the synthesis of Compound 1 from Intermediate 5 of Preparation Example 1, except that piperazine, 2,6-diaminopyridine, p-phenyldiamine and 1,4-diaminonaphthalene were used instead of 2,2'-oxybisethylamine, respectively.

Compound 19 was synthesized as in the synthesis of Compound 1 from Intermediate 5 of Preparation Example 1, except that an amine bridge represented by the following formula was used instead of 2,2'-oxybisethylamine.

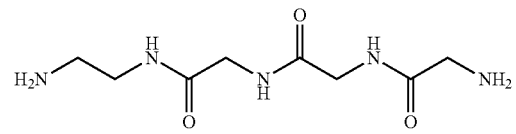 [SMILES: NCCNC(=O)CNC(=O)CNC(=O)CN]

Compound 20 was synthesized as in the synthesis of Compound 1 from Intermediate 5 of Preparation Example 1, except that an amine bridge represented by the following formula was used instead of 2,2'-oxybisethylamine.

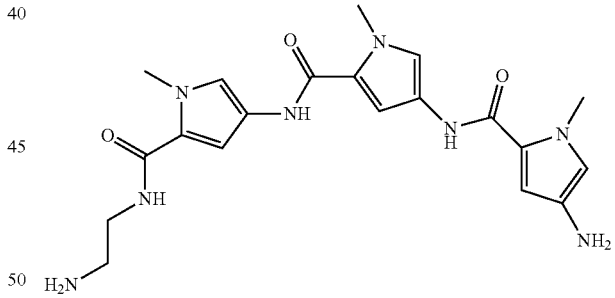

Preparation Example 6

Synthesis of Compound 36

(1) Synthesis of Intermediate 1 and Intermediate 2

2-(methylthio)benzoxazole

-continued

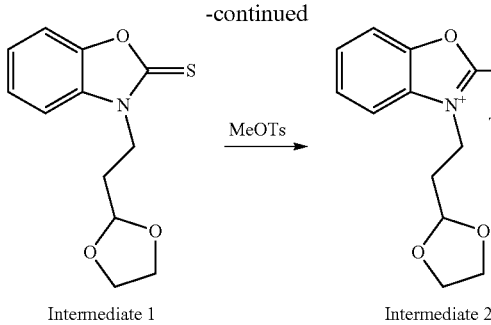

Intermediate 1 → Intermediate 2 (MeOTs)

To a 1 L single-neck reactor were added Oxolane, i.e., 2-bromoethyl-1,3-dioxolane (52.6 g, 0.290 mol), potassium iodide (64.3 g, 0.387 mol) and acetonitrile (320 mL) were placed, and the mixture was stirred at 50° C. for 1 hour. Then, 2-(methylthio)benzoxazole (32.0 g, 0.193 mol) was added to the reactor, and the mixture was stirred under reflux for 20 hours, cooled, concentrated and purified by column to obtain Intermediate 1 (30.2 g, 0.120 mol, 62%). $^1$H-NMR (400 MHz, CDCl$_3$) δ 7.40-7.28 (m, 4H), 4.93 (t, J=4.4 Hz, 1H), 4.33 (t, J=6.8 Hz, 2H), 4.10-3.90 (m, 2H), 3.84-3.78 (m, 2H), 2.22-2.00 (m, 2H).

Intermediate 1 (1.0 g, 3.979 mmol), methyl tosylate (MeOTs) (0.9 mL, 5.968 mmol) and dimethylformamide (2 mL) were then added to a 50 mL single-neck reactor, and the mixture was stirred at 120° C. for 1 hour, and ethyl acetate was then added to the reactor, followed by stirring at room temperature. The supernatant was then discarded and vacuum dried to give Intermediate 2 (0.9 g, 2.057 mmol, 52%). $^1$H-NMR (300 MHz, MeOD) δ 7.95-7.89 (m, 2H), 7.73-7.66 (m, 4H), 7.22 (d, J=7.8 Hz, 2H), 4.96 (t, J=3.6 Hz, 1H), 4.54 (t, J=6.6 Hz, 2H), 3.93-3.77 (m, 4H), 3.19 (s, 3H), 2.44-2.35 (m, 5H).

(2) Synthesis of Intermediate 3

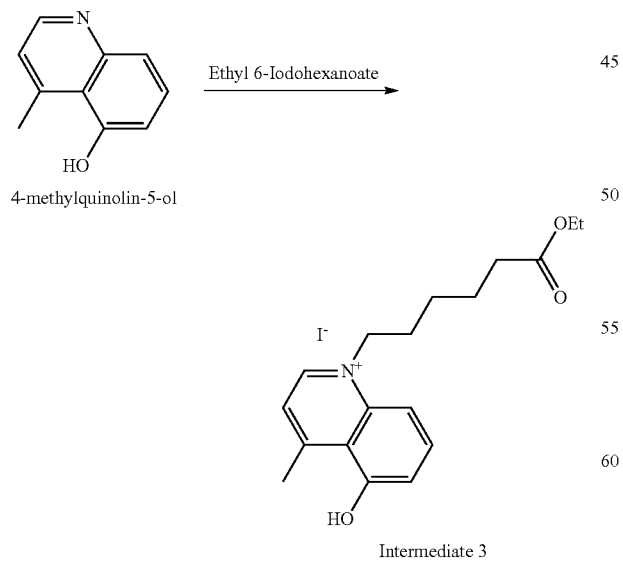

4-methylquinolin-5-ol → Intermediate 3 (Ethyl 6-Iodohexanoate)

4-methyl-5-quinolinol (2 g, 0.0125 mol), ethyl 6-iodohexanoate (10 g, 0.0375 mol) and dimethylformamide (4 mL) were placed in a 50 mL single-neck reactor, and stirred at 120° C. for 12 hours, then cooled, concentrated and purified by column to give Intermediate 3 (3.6 g, 0.00828 mol, 67%). $^1$H-NMR (400 MHz, DMSO-d$_6$) δ 9.19 (d, J=6.4 Hz, 1H), 7.952 (t, J=8.0 Hz, 1H), 7.73-7.77 (m, 2H), 7.22 (d, J=7.6 Hz, 1H), 4.85 (t, J=6.8 Hz, 2H), 4.01 (q, J=7.6 Hz, 2H), 3.09 (s, 3H), 2.35 (t, J=7.6 Hz, 2H), 1.89-1.93 (m, 2H), 1.55-1.61 (m, 4H), 1.12 (t, J=6.8 Hz, 3H).

(3) Synthesis of Intermediate 4

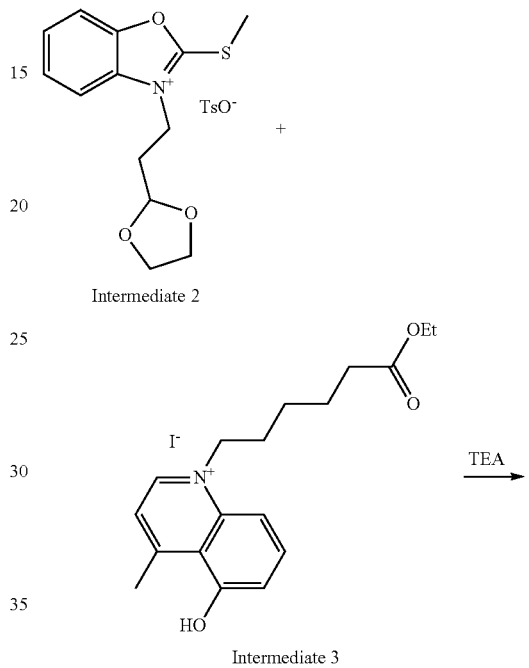

Intermediate 2 + Intermediate 3 →(TEA) Intermediate 4

Intermediate 2 (1.87 g, 4.292 mmol), Intermediate 3 (1.45 g, 4.292 mmol) and dichloromethane (20 mL) were added to a 100 mL single-neck reactor, and the mixture was stirred at room temperature for 5 minutes. Then, triethylamine (TEA) (0.868 g, 8.584 mmol) was added to the reactor, followed by stirring at room temperature for 12 hours, then concentrated and purified by column to obtain Intermediate 4.

(4) Synthesis of Intermediate 5

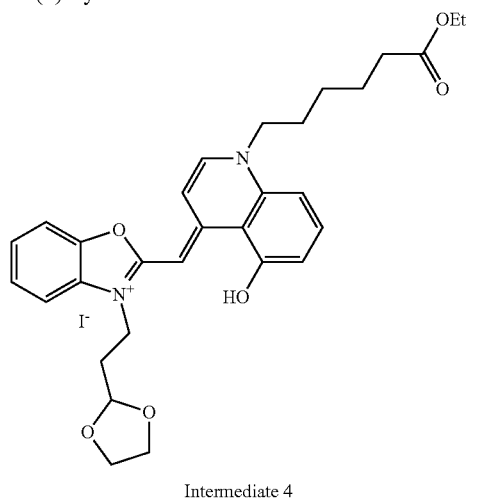

Intermediate 4

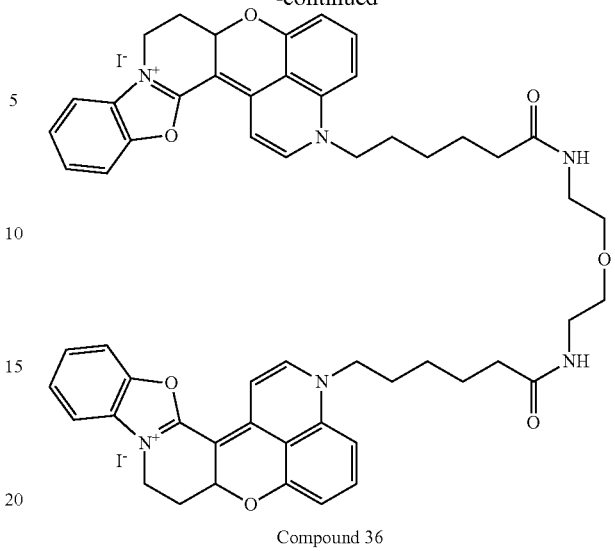

Compound 36

Intermediate 4 (8.6 g, 0.0133 mmol), 50% aqueous sulfuric acid solution (50 mL) and chloroform (250 mL) were added to a 500 mL single-neck reactor and stirred at room temperature. Then, water (10 mL) was added to the reactor and the mixture was extracted with dichloromethane (2×50 mL), and the organic layer was concentrated and purified by column to obtain Intermediate 5 (0.37 g, 0.665 mmol, 5%). $^1$H-NMR (400 MHz, MeOD) δ 8.25 (d, J=6.8 Hz, 1H), 7.80 (t, J=8.4 Hz, 1H), 7.69 (d, J=7.6 Hz, 2H), 7.53-7.47 (m, 3H), 7.44-7.40 (m 1H), 7.08 (d, J=8.0 Hz, 1H), 5.31-5.27 (m, 1H), 4.57-4.50 (m, 2H), 4.47-4.40 (m, 1H0, 4.18-4.10 (m, 1H), 2.87-2.83 (m, 1H), 2.57-2.47 (m, 1H)m, 2.31 (s, J=7.2 Hz, 2H), 1.99-1.92 (m, 2H), 1.71-1.64 (m, 2H), 1.51-1.43 (m, 2H).

(5) Synthesis of Compound 36

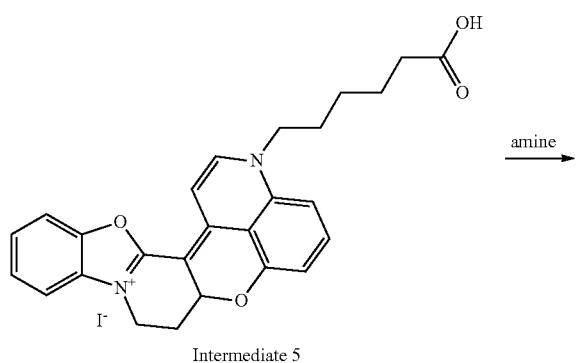

Intermediate 5

To a 250 mL single-neck reactor was added Intermediate 5 (123 mg, 0.220 mmol), TBTU (106 mg, 0.330 mmol) and dimethylformamide (2 mL), followed by stirring at room temperature for 5 minutes, and triethylamine (92 μL, 0.660 mmol) and 2,2'-oxybisethylamine (23 μL, 0.220 mmol) were added, and the mixture was stirred at room temperature for 12 hours. Then, the reaction solution was poured into ethyl acetate (40 mL) to precipitate a solid. The precipitated solid was filtered and purified by column to obtain Compound 36 (30 mg, 0.0906 mmol, 11%). $^1$H-NMR (400 MHz, MeOD) δ 8.21 (d, J=7.2 Hz, 2H), 7.77-7.72 (m, 2H), 7.66 (d, J=8.0 Hz, 2H), 7.60 (t, J=6.8 Hz, 2H), 7.49-7.44 (m, 6H), 7.41-7.37 (m, 2H), 7.06-7.03 (m, 2H), 5.24-2.18 (m, 2H), 4.54-4.49 (m, 2H), 4.44-4.37 (m, 4H), 4.14-4.07 (m, 2H), 3.49-3.47 (m, 4H), 3.32 (m, 4H), 2.84-2.81 (m, 2H), 2.52-2.39 (m, 2H), 2.23 (t, J=7.2 Hz, 4H), 1.94-1.91 (m, 4H), 1.70-1.65 (m, 4H), 1.49-1.40 (m, 4H).

Preparation Example 7

Synthesis of Compound 37 to Compound 39

Compound 37, Compound 38 and Compound 39 were synthesized using 1,2-bis(2-aminoethoxy)ethane, 1,11-diamino-3,6,9-trioxaundecane, 4,7,10-trioxa-1,13-tridecanediamine instead of 2,2'-oxybisethylamine in the synthesis of Compound 1 from Intermediate 5 of Preparation Example 6.

Compound 37—$^1$H-NMR (400 MHz, MeOD) δ 8.20 (d, J=7.2, 2H), 7.76-7.70 (m, 2H), 7.65 (d, J=8.0 Hz, 2H), 7.61-7.57 (m, 2H), 7.48-7.42 (m, 6H), 7.39-7.35 (m, 2H), 7.04-7.01 (m, 2H), 5.23-5.17 (m, 2H), 4.52-4.47 (m, 2H), 4.44-4.34 (m, 4H), 4.12-4.06 (m, 2H), 3.57 (s, 4H), 3.51-3.48 (m, 4H), 3.36-3.30 (m, 4H), 2.83-2.80 (m, 2H), 2.48-2.40 (m, 2H), 2.25-2.21 (m, 4H), 1.93-1.89 (m, 4H), 1.68-1.64 (m, 4H), 1.46-1.39 (m, 4H)

Compound 38—$^1$H-NMR (400 MHz, MeOD) δ 8.20 (d, J=7.2 Hz, 2H), 7.77-7.72 (m, 2H), 7.66 (d, J=8.0 Hz, 2H), 7.62-7.59 (m, 2H), 7.47-7.44 (m, 6H), 7.41-7.36 (m, 2H), 7.03 (d, J=8.0 Hz, 2H), 5.25-5.19 (m, 2H), 4.52-4.48 (m, 2H), 4.44-4.39 (m, 4H), 4.13-4.07 (m, 2H), 3.59-3.58 (m, 8H), 3.50-3.48 (m, 4H), 3.33-3.30 (m, 4H), 2.84-2.81 (m, 2H), 2.49-2.40 (m, 2H), 2.21 (t, J=7.2 Hz, 4H), 1.94-1.89 (m, 4H), 1.69-1.65 (m, 4H), 1.44-1.43 (m, 4H)

Compound 39—$^1$H-NMR (400 MHz, MeOD) δ 8.22-8.21 (m, 2H), 7.78-7.72 (m, 2H), 7.67 (d, J=8.0 Hz, 2H), 7.63-7.60 (m, 2H), 7.51-7.44 (m, 6H), 7.41-7.37 (m, 2H), 7.05-7.03 (m, 2H), 5.26-4.20 (m, 2H), 4.53-4.49 (m, 2H), 4.47-4.37 (m, 4H), 4.15-4.07 (m, 2H), 3.60-3.58 (m, 4H), 3.54-3.53 (m, 4H), 3.48-3.45 (m, 4H), 3.23-3.20 (m, 4H), 2.85-2.82 (m, 2H), 2.50-2.42 (m, 2H), 2.20 (t, J=7.2 Hz, 4H), 1.97-1.89 (m, 4H), 1.73-1.68 (m, 8H), 1.46-1.40 (m, 4H)

Absorption spectra ($\lambda_{abs}$), emission spectra ($\lambda_{em}$), molar extinction coefficient (ε) and quantum efficiency of Compounds 36 to 39 obtained in Preparation Examples 6 and 7 and commercially available SYBR® safe were measured and shown in Table 2 below.

TABLE 2

| Classification | Solvent | $\lambda_{abs}$(nm) | $\lambda_{em}$(nm) | ε(M$^{-1}$cm$^{-1}$) | Quantum efficiency |
|---|---|---|---|---|---|
| SYBR ® safe | buffer | 502 | ND | 57,000 | 0.006 |
|  | DMSO | 509 | ND | 77,000 | 0.006 |
| Compound 36 | buffer | 458 | 526 | 83,000 | 0.12 |
|  | DMSO | 492 | 520 | 95,000 | 0.65 |
| Compound 37 | buffer | 458 | 524 | 85,000 | 0.14 |
|  | DMSO | 492 | 520 | 100,000 | 0.63 |
| Compound 38 | buffer | 459 | 522 | 95,000 | 0.17 |
|  | DMSO | 492 | 520 | 110,000 | 0.67 |
| Compound 39 | buffer | 459 | 523 | 98,000 | 0.15 |
|  | DMSO | 492 | 520 | 116,000 | 0.70 |

It can be seen that Compounds 36 to 39 obtained in Preparation Examples 6 and 7 exhibited similar or superior molar extinction coefficients to SYBR® safe and were remarkably excellent in terms of quantum efficiency.

EXPERIMENTAL EXAMPLES

Experimental Example 1

Experiment of Labeling Nucleic Acid

In order to compare the nucleic acid labeling properties of Compound 1 to Compound 8 and Compound 38 prepared according to Preparation Examples and SYBR® safe, a commercially available dye, nine agarose gels were prepared by mixing 4 μL each in 1% agarose gel (40 mL 1×TAE buffer+0.4 g agarose).

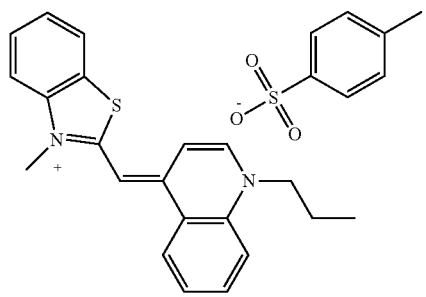

[SYBR® safe]

The prepared nine agarose gels were completely immersed in 1×TAE buffer, and 10 μL, 5 μL, 2.5 μL, 1 μL, and 0.5 μL of DNA samples were loaded into 5 wells, respectively. Electrophoresis was performed for 30 minutes at a power of 100V. The electrophoresis results are shown in FIGS. 1 and 2 to 10.

FIGS. 2 to 10 show electrophoresis results of Compounds 1 to 8 and 38, respectively.

Referring to FIGS. 1 to 10, when the merocyanine-based compound according to various embodiments of the present disclosure is used as a dye in comparison with SYBR® safe, it can be confirmed that the background signal is uniform, and the overall brightness of the band was brighter than that of SYBR® safe, indicating improved readability of the labeling results.

In addition, in the case of SYBR® safe, it can be observed that in spite of UV irradiation for 0.5 sec, the overall brightness of the band is dark, while, referring to FIGS. 6 to 10, a brighter band was observed despite UV irradiation for a shorter time than SYBR® safe.

Figure 11:
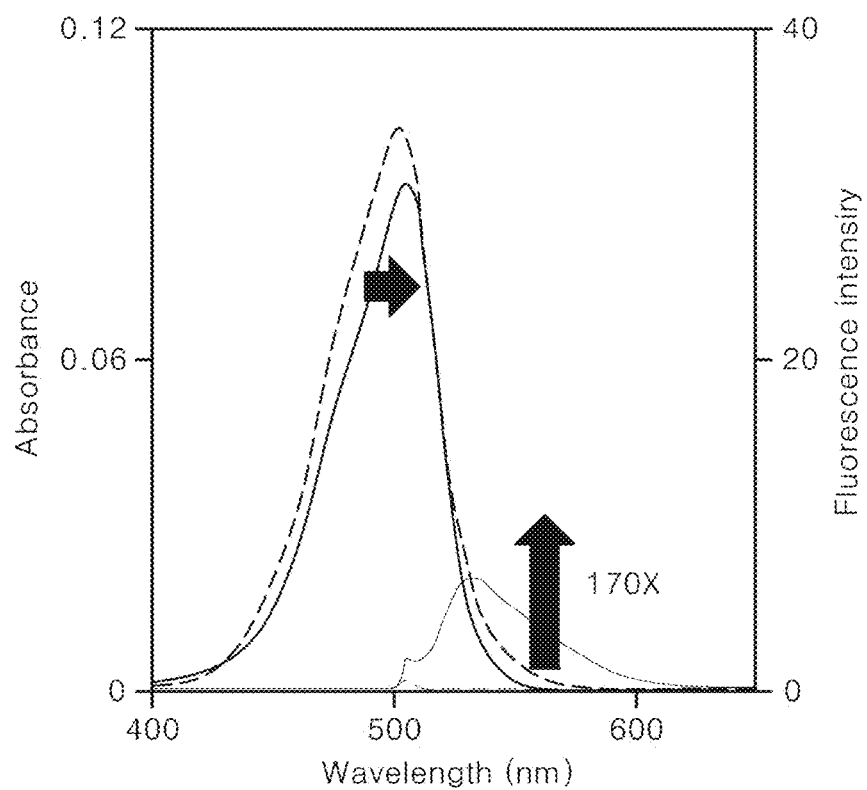
FIG. 11 shows absorption and emission spectrum results of SYBR® safe, a commercially available dye.
Figure 12:
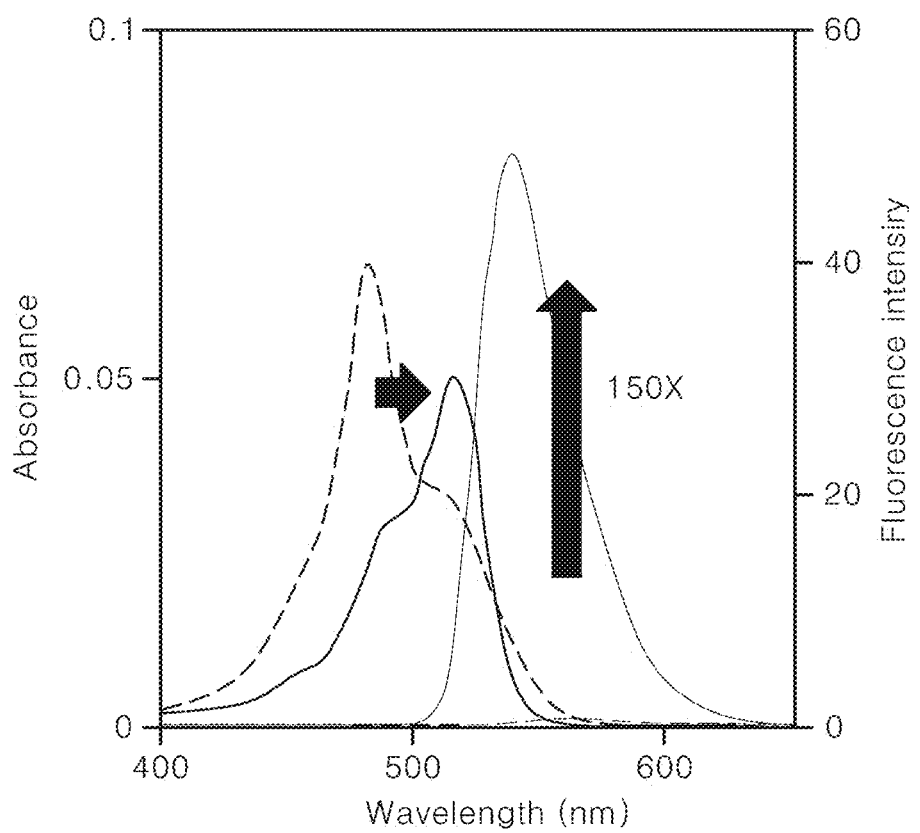
FIGS. 12 and 13 show absorption and emission spectral results of merocyanine-based compounds according to various embodiments of the present disclosure.
Figure 13:
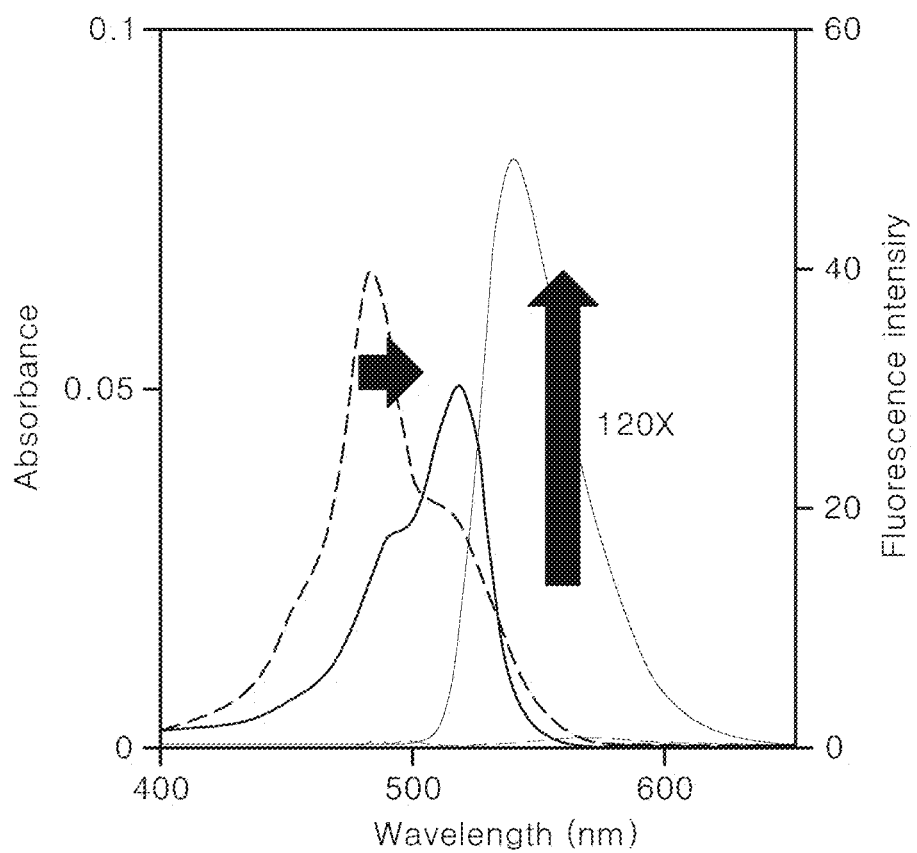

FIG. 11 shows the absorption and emission spectral results of SYBR® safe, a commercially available dye, and FIGS. 12 and 13 show absorption and emission spectral results of Compound 3 and Compound 6, respectively.

It can be observed that SYBR® safe, Compound 3 and Compound 6 all intercalate into DNA and the absorption wavelength shifts to a longer wavelength (red shift), and the fluorescence intensity increases, but the fluorescence intensity according to red shifted Compounds 3 and 6 was significantly improved compared to the SYBR® safe fluorescence intensity.

Absorption spectra ($\lambda_{abs}$), emission spectra ($\lambda_{em}$) and quantum efficiency measured in the presence of DNA with compounds 1 to 8 and 36 to 39, and commercially available SYBR® safe were measured and are shown in Table 3 below.

TABLE 3

| Classification | $\lambda_{abs}$(nm) | $\lambda_{em}$(nm) | Quantum efficiency |
|---|---|---|---|
| SYBR ® safe | 503 | 535 | 0.021 |
| Compound 1 | 517 | 541 | 1.00 |
| Compound 2 | 517 | 541 | 0.93 |
| Compound 3 | 517 | 540 | 0.86 |
| Compound 4 | 517 | 539 | 0.88 |
| Compound 5 | 517 | 537 | 0.86 |
| Compound 6 | 517 | 538 | 0.73 |
| Compound 7 | 517 | 538 | 0.71 |
| Compound 8 | 517 | 538 | 0.80 |
| Compound 36 | 492 | 511 | 0.67 |
| Compound 37 | 492 | 512 | 0.64 |
| Compound 38 | 492 | 512 | 0.76 |
| Compound 39 | 492 | 513 | 0.70 |

It can be seen that Compounds 1 to 8 and 36 to 39 show fluorescence signals in the wavelength range similar to that of commercially available SYBR® safe in the presence of DNA, but exhibit significantly better quantum efficiency than SYBR® safe.

Experimental Example 2

Cell Permeability

In order to confirm the cell permeability of SYBR® safe and Compounds 1, 4 and 6 according to one embodiment of the present disclosure, heliocytosis was used.

Hela cells were cultured in MEM medium containing 10% fetal bovine serum (FBS) and 1% penicillin/streptomycin (10,000 units penicillin and 10,000 μg/mL streptomycin, Invitrogen) under a humidified atmosphere of $CO_2$ at 37° C. Hela cells were washed with medium No. 3, and 1 μM of SYBR® safe and Compound 6 were treated with Hela Cells and cultured at 37° C. for 30 minutes. After washing with media No. 3 as above, images were observed with a microscope. The results are shown in FIGS. 14 to 17.

Figure 14:
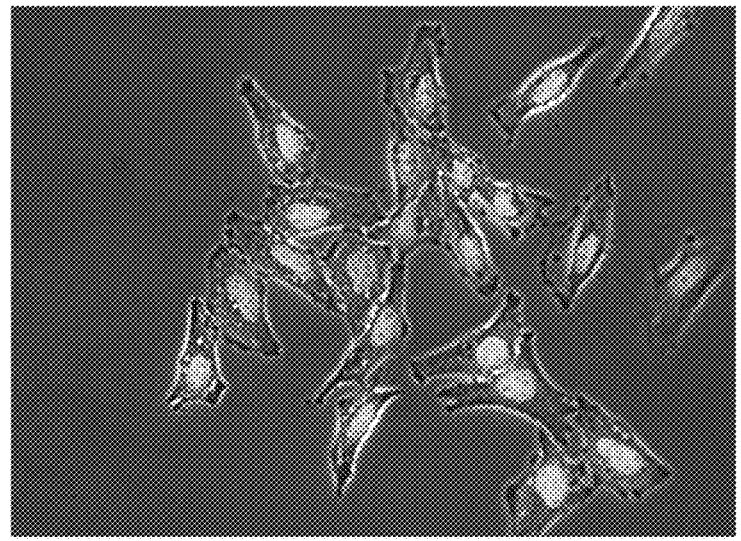
FIG. 14 is an image showing result of cell permeability test of SYBR® safe, a commercially available dye.
Figure 15:
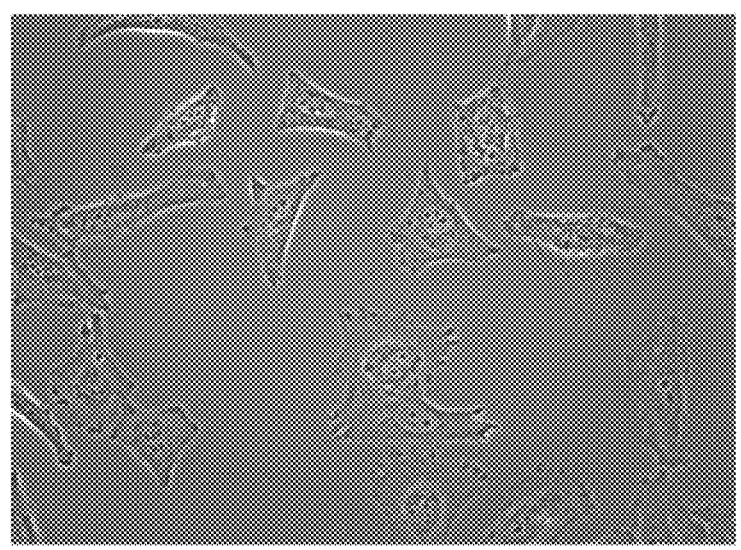
FIGS. 15 to 17 are images showing results of cell permeability test of merocyanine-based compounds according to various embodiments of the present disclosure.
Figure 16:
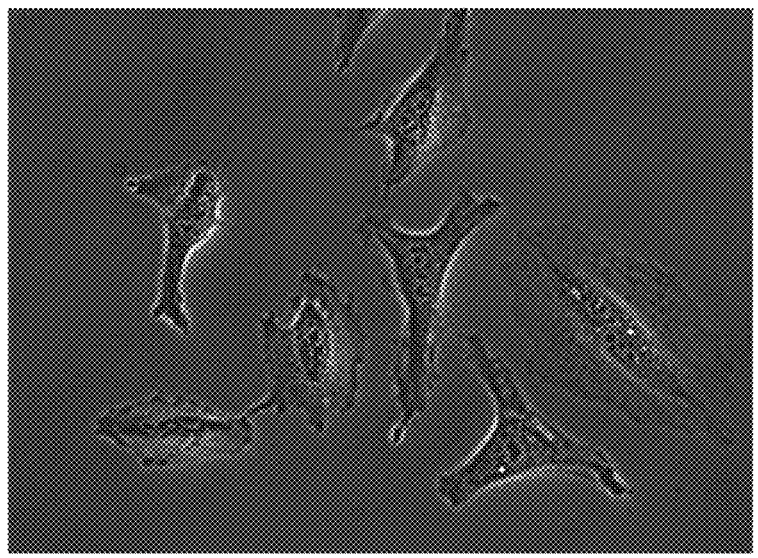
Figure 17:
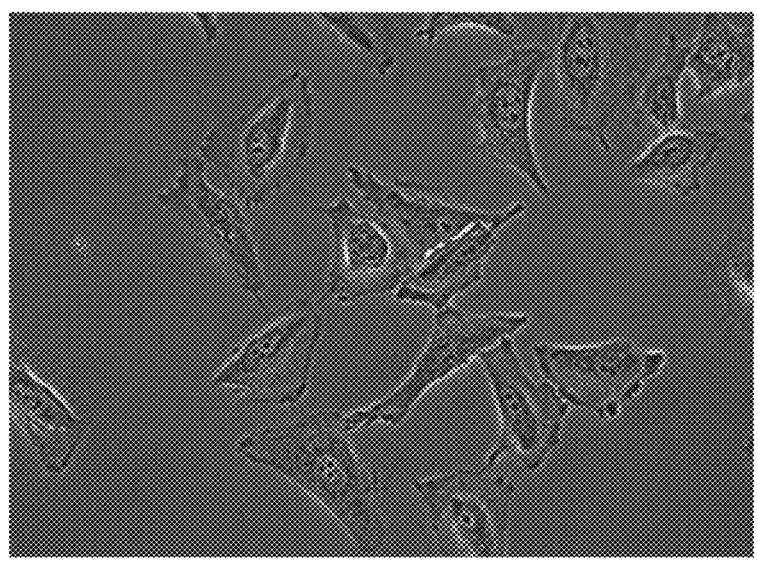

FIG. 14 is an image showing the results of a cell permeability test of SYBR® safe, a commercially available dye, and FIGS. 15, 16 and 17 are an image showing the results of cell permeability test of Compound 1, Compound 4, and Compound 6, respectively.

It can be seen that, referring to FIG. 14, SYBR® safe shows cell permeability, while, referring to FIGS. 15-17, compounds according to various embodiments of the disclosure do not penetrate cells.

Experimental Example 3

Cell Cycle Analysis

Cells were seeded at $5 \times 10^5$ to $1 \times 10^6$ in each well of a 6-well plate, treated with vehicle and TNFα (tumor necrosis factor alpha), recovered with trypsin-EDTA, transferred to a FACS tube, and washed with 1 mL of PBS (4° C.). Then, 300 μL of PBS (4° C.) was added to the tube, and the cells were suspended.

700 μL of 100% Et-OH was added dropwise, while vortexing the tube containing the suspended cells, to react at 4° C. for 1 hour or more, allowing a cell fixation, and Et-OH was washed with PBS (phosphate-buffered saline), 10 μL of Compound 6 (2 μM) or PI (propidium iodide) (50 mg/mL) and 1 μL of RNase at a concentration of 1 mg/mL were added to the cells suspended in 1 mL of PBS, and the mixture was then reacted in a dark room for 30 minutes, and analyzed using a flow cytometry.

In other words, the nucleus is gated using FSC-A and SSC-A, and the singlet is separated by adjusting FITC-A and FITC-W plots with voltage. The peak of DNA 2N and 4N was designated by adjusting the separated singlet with voltage while observing the FITC-A histogram, and the G0/G1, S and G2/M phases were discriminated. The results are shown in FIGS. 5a and 5b.

Figure 18:
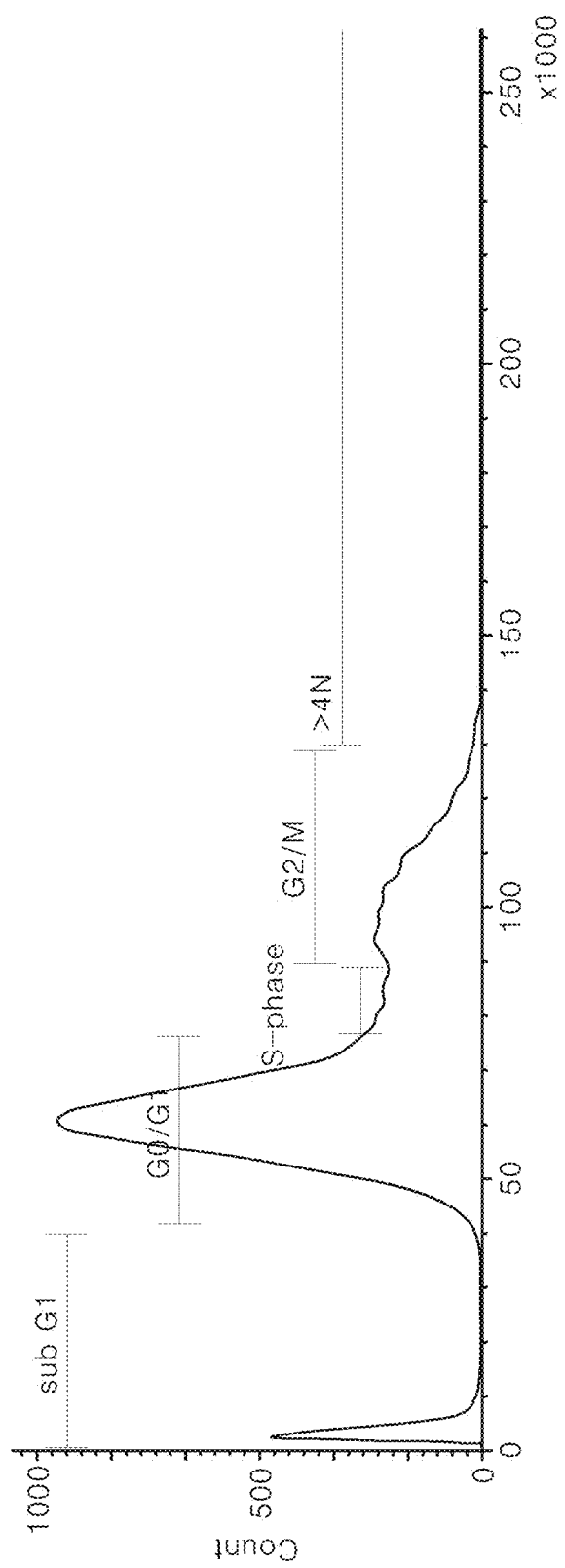
FIG. 18 is a graph showing results of cell cycle analysis using propidium iodide, which is a commercialized cell cycle assay dye.
Figure 19:
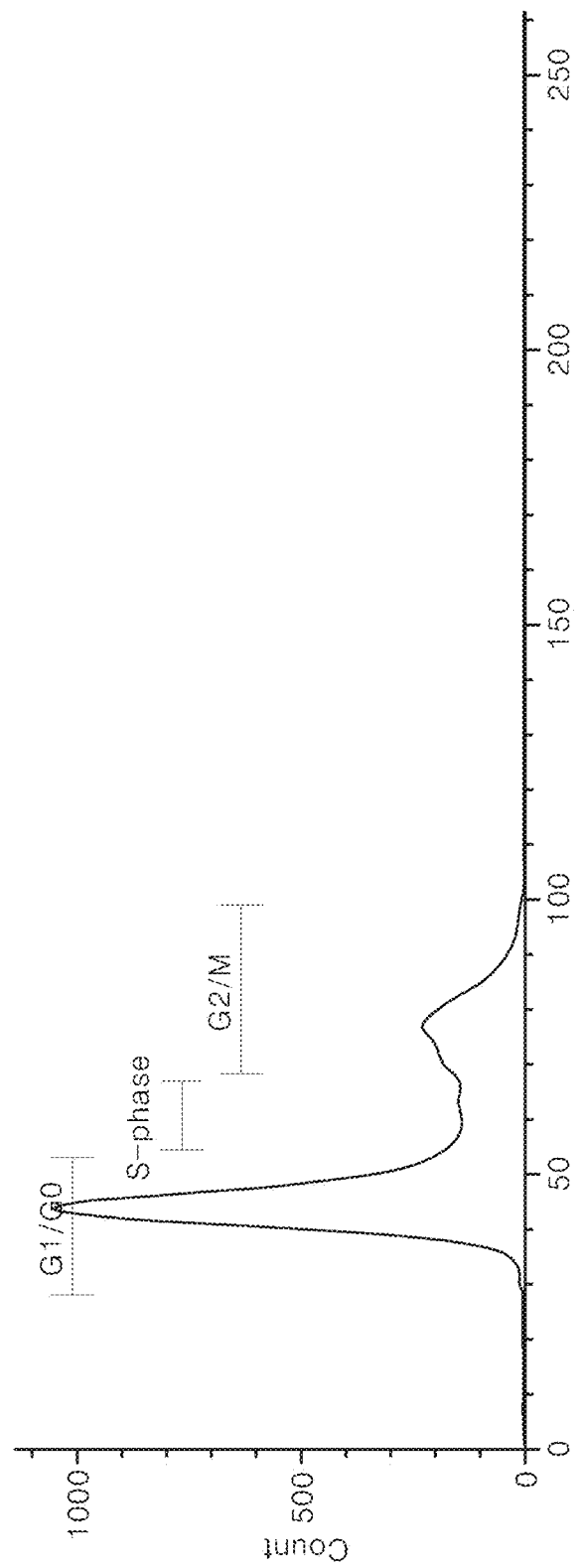
FIG. 19 is a graph showing results of cell cycle analysis using Compound 6.

FIG. 18 is a graph showing the results of cell cycle analysis using propidium iodide, which is a commercially available cell cycle assay dye, and FIG. 19 is a graph showing the results of cell cycle analysis using Compound 6.

Comparing FIGS. 18 and 19, it can be seen that the results of the cell cycle analysis of FIG. 19 are clearly distinguished from each other as compared with FIG. 18, and the visibility of signals is also improved.

Experimental Example 4

Ames Test

For the purpose of evaluating the genetic toxicity of Compound 6 according to one embodiment of the present disclosure, Ames test using a bacterial strain was performed.

The growth of the test strains according to the treatment with Compound 6, EtBr and SYBR® safe was monitored in the test system treated with S9 mixture, which is a metabolic activation enzyme, in a mouse strain Typhus (*Salmonella typhimurium* TA98 strain), which is a Hystidine-dependent mutant strain cryopreserved as a test strain.

The test strain being stored in a deep freezer was inoculated into a sterile liquid medium (2.5% Oxoid Nutrient Broth No. 2) and cultured in a shaking incubator (37° C., 200 rpm) for 10 hours. Minimal Glucose Agarplates were prepared by dispensing 20 mL each of 1.5% Bacto agar (Difco), Vogel-Bonner medium E and 2% glucose in a petri dish (90×15 mm). Top agar was prepared with 0.6% agar and 0.5% NaCl, and histidine-biotin was added to the top agar for *Salmonella typhimurium* strain to a concentration of 0.05 mM.

To sterile tubes (12×75 mm) set in a heating block preheated to 45° C. were dispensed each volume of 2 mL of high-pressure sterilized top agar. Immediately after each 0.1 mL of compound 6, EtBr and SYBR® safe, and each 0.1 mL of S9 mixture and the test strain culture were added, the mixture was shaken with a vortex-mixer for 2 to 3 seconds, poured into a minimal glucose agar plate, and tilted in various directions, and then solidified. When the top agar was solidified, the plate was turned over and cultured at 37° C. for 48 hours, and then the number of colonies was counted.

The treatment concentrations (μg/plate) of Compound 6, EtBr and SYBR® safe and the number of colonies counted per plate are as follows.

TABLE 4

| Compound | Concentration (μg/plate) | Number of colonies per plate |
| --- | --- | --- |
| EtBr | 0 | 19 ± 4 |
|  | 40 | 3051 ± 181 |
| Compound 6 | 0 | 20 ± 4 |
|  | 40 | 57 ± 3 |

Table 4 above indicates that compared with the number of EtBr colonies known to exhibit an existing genotoxicity, Compound 6 showed no significant increase in colony counts in S9 metabolic activity TA98 strain. That is, Compound 6 can fully replace EtBr as a non-genotoxic dye.

TABLE 5

| Compound | Concentration (μg/plate) | Number of colonies per plate |
| --- | --- | --- |
| SYBR ® safe | 0 | 24 ± 2 |
|  | 1.6 | 81 ± 7 |
| Compound 6 | 0 | 20 ± 4 |
|  | 8 | 24 ± 6 |

As can be seen from the results in Table 5 above, the SYBR® safe dye currently available has a greater number of colonies than Compound 6 even at a lower concentration (1.6 μg/plate) than Compound 6 treatment concentration (8 μg/plate).

Considering that staining concentration of a gel is usually 1 to 3 μg/mL (3 to 8 μg/plate) during electrophoresis, within the above concentration range, Compound 6 can exhibit lower genotoxicity than SYBR® safe.

Experimental Example 5 qPCR Test (1) qPCR was performed in a 20 μL reaction solution containing 10 μL of 2× Real-Time PCR Master Mix (Cellsafe), Hela cDNA of various concentrations, 1 μL of 10 μmol forward primer, 1 μL of 10 μmol reverse primer and 1 μL of Compound 38. The fragments in the cDNA were amplified using a primer (GAPDH). Cycles performed for 5 minutes at 95° C., 10 seconds at 95° C., 20 seconds at 60° C., and 15 seconds at 72° C. were repeated 40 times, and fluorescence was measured at 72° C. The results of qPCR are shown in Table 6 below.

Figure 34:
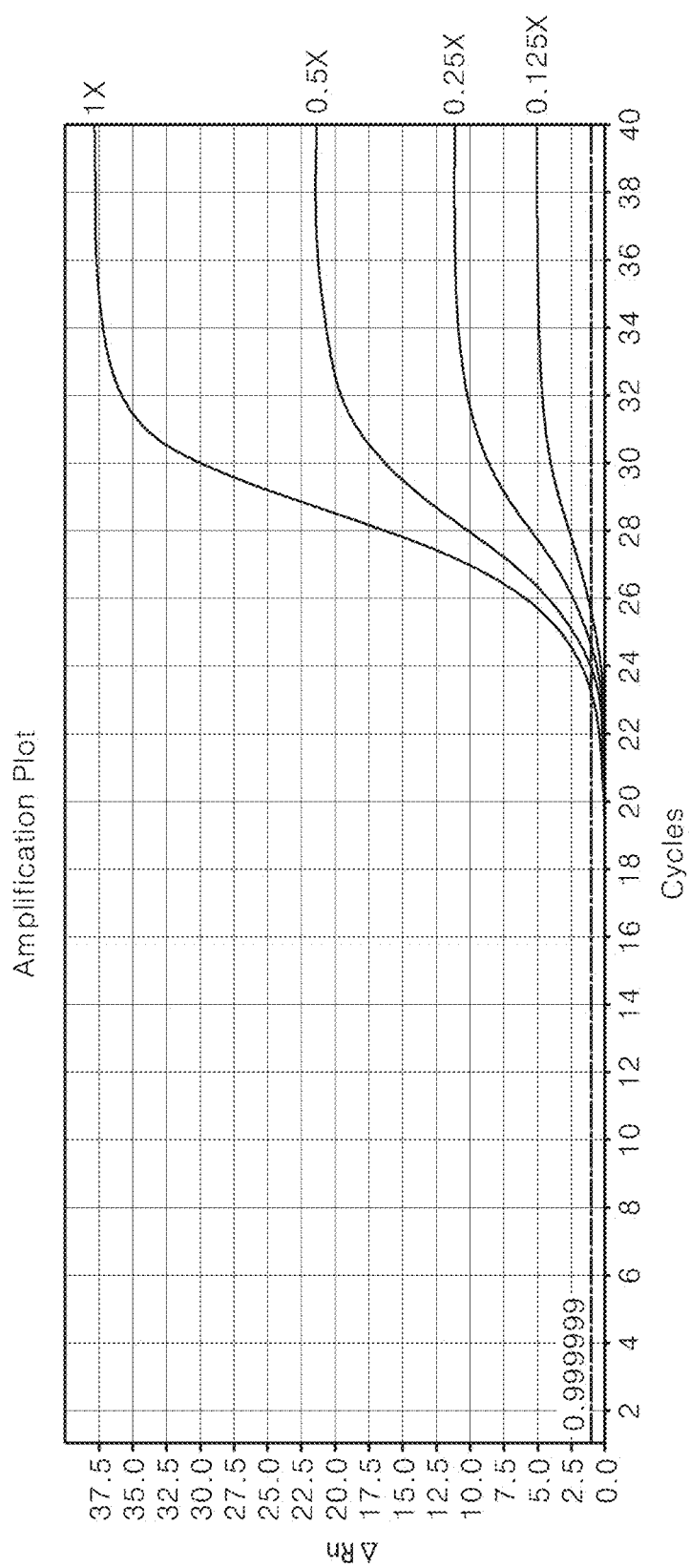
FIG. 34 is a graph showing amplification curve of qPCR according to a fluorescent dye concentration using Compound 38 as a fluorescent dye.
Figure 35:
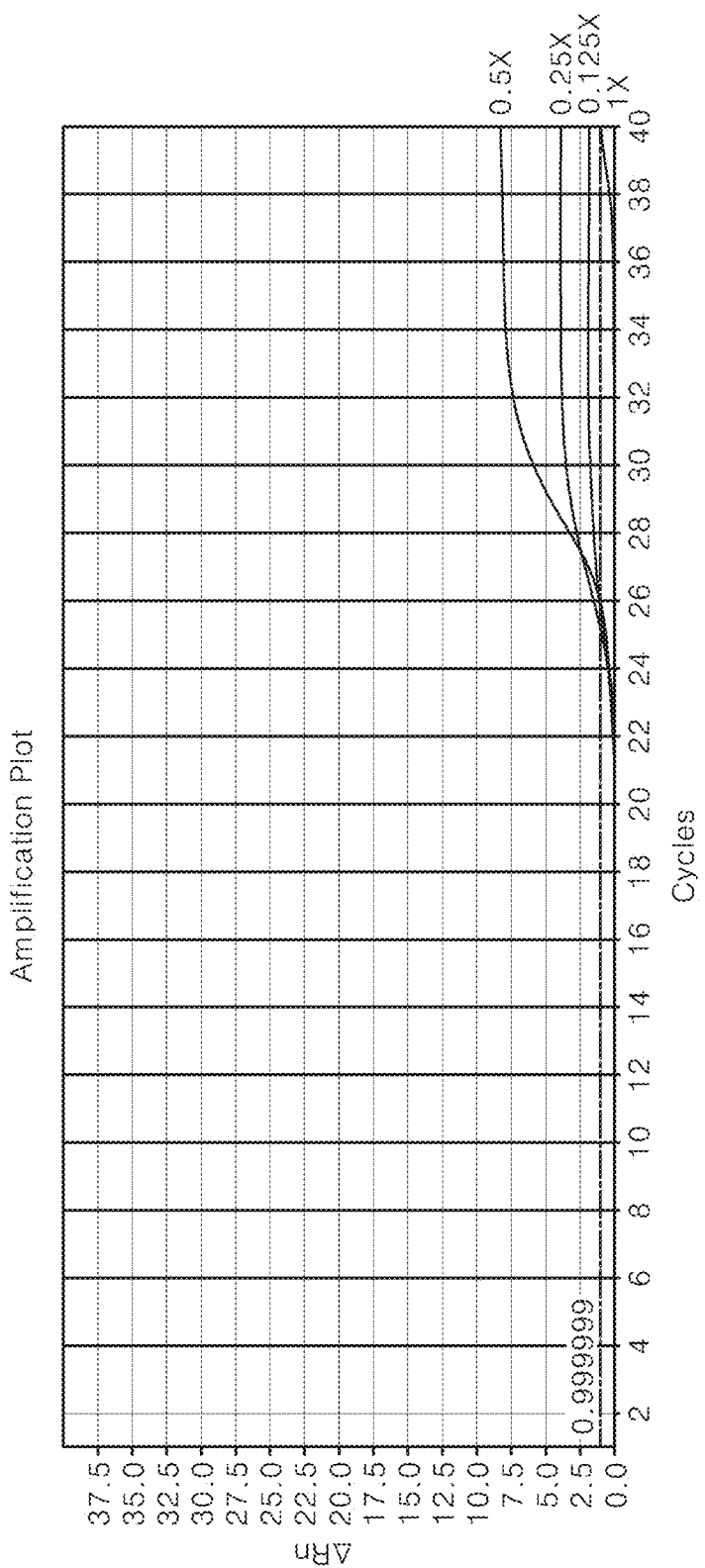
FIG. 35 is a graph showing amplification curve of qPCR according to a fluorescent dye concentration using SYBR® green I as a fluorescent dye.
Figure 36:
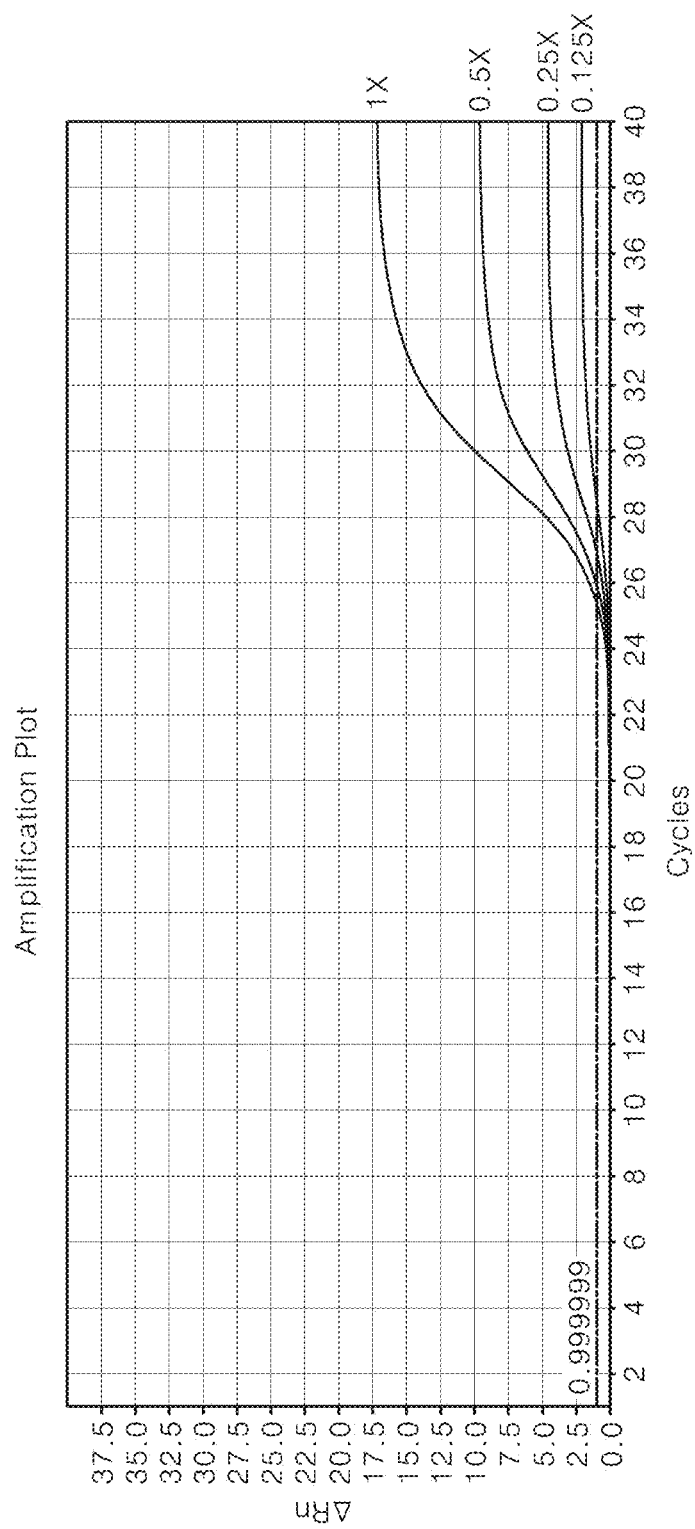
FIG. 36 is a graph showing amplification curve of qPCR according to a fluorescent dye concentration using EvaGreen™ as a fluorescent dye.
Figure 37:
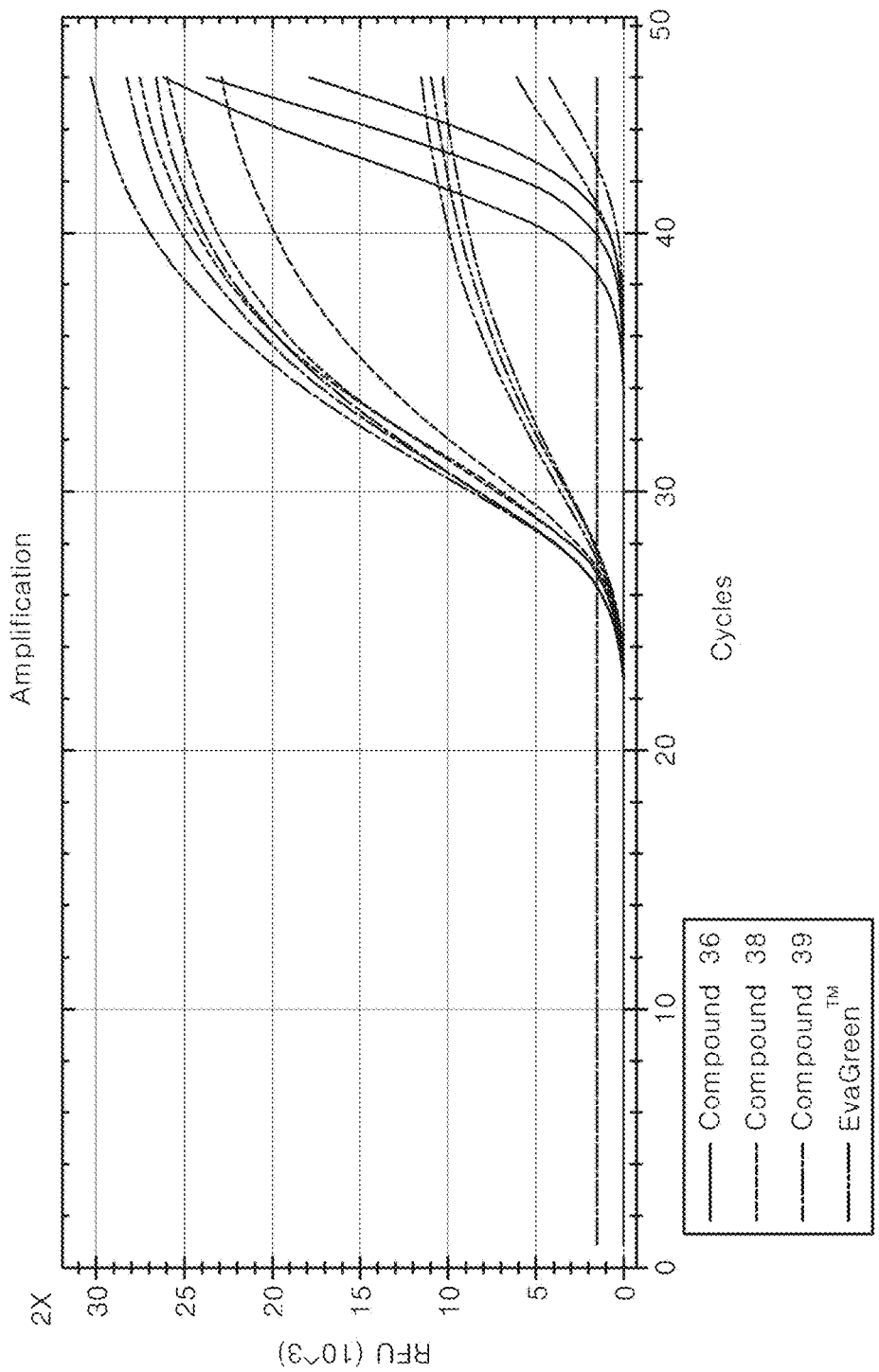
FIGS. 37 to 42 are graphs showing amplification curves and melting curves of qPCR using Compound 36, Compound 38, Compound 39 and EvaGreen™ as fluorescent dyes.
Figure 38:
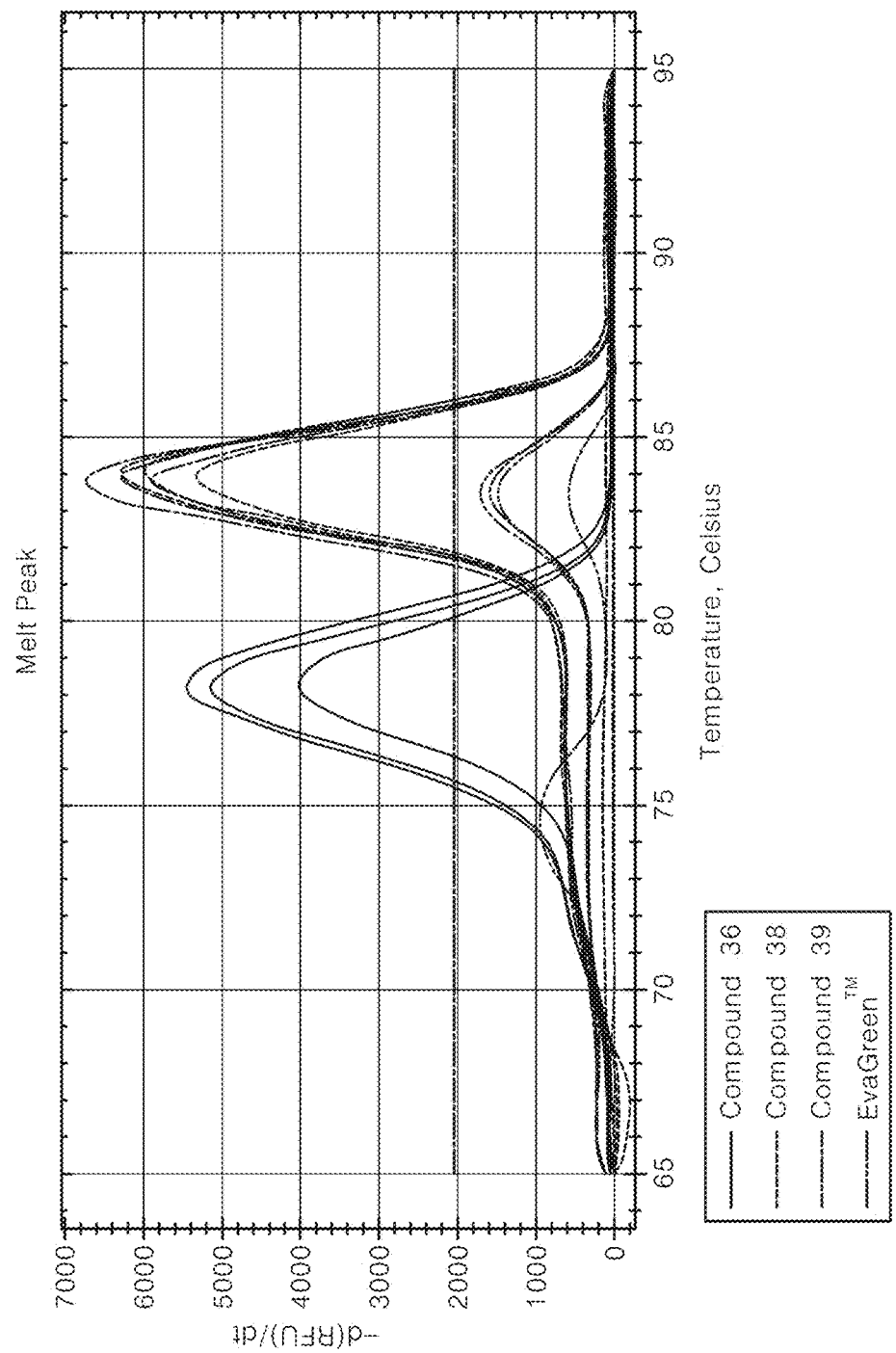
Figure 39:
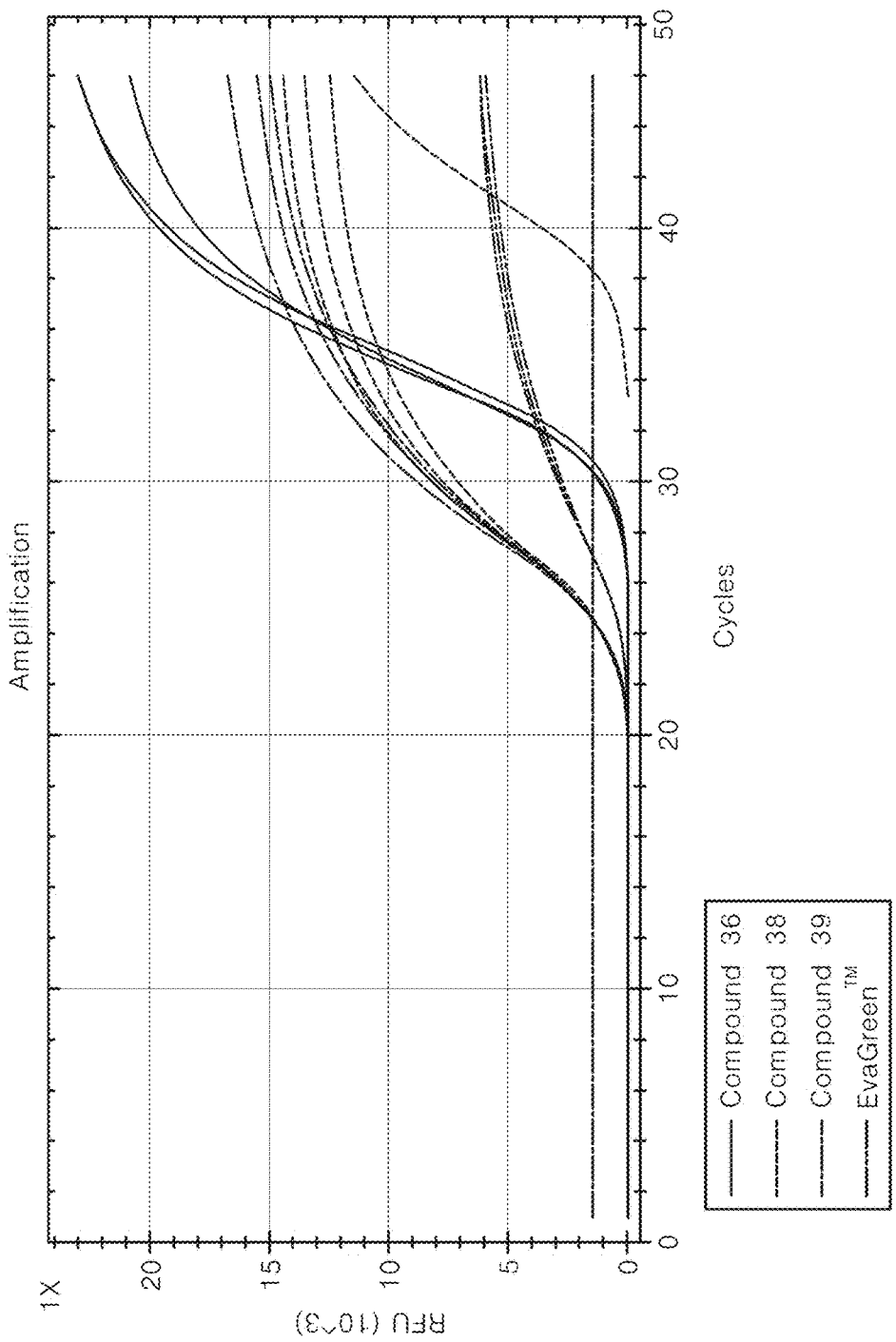
Figure 40:
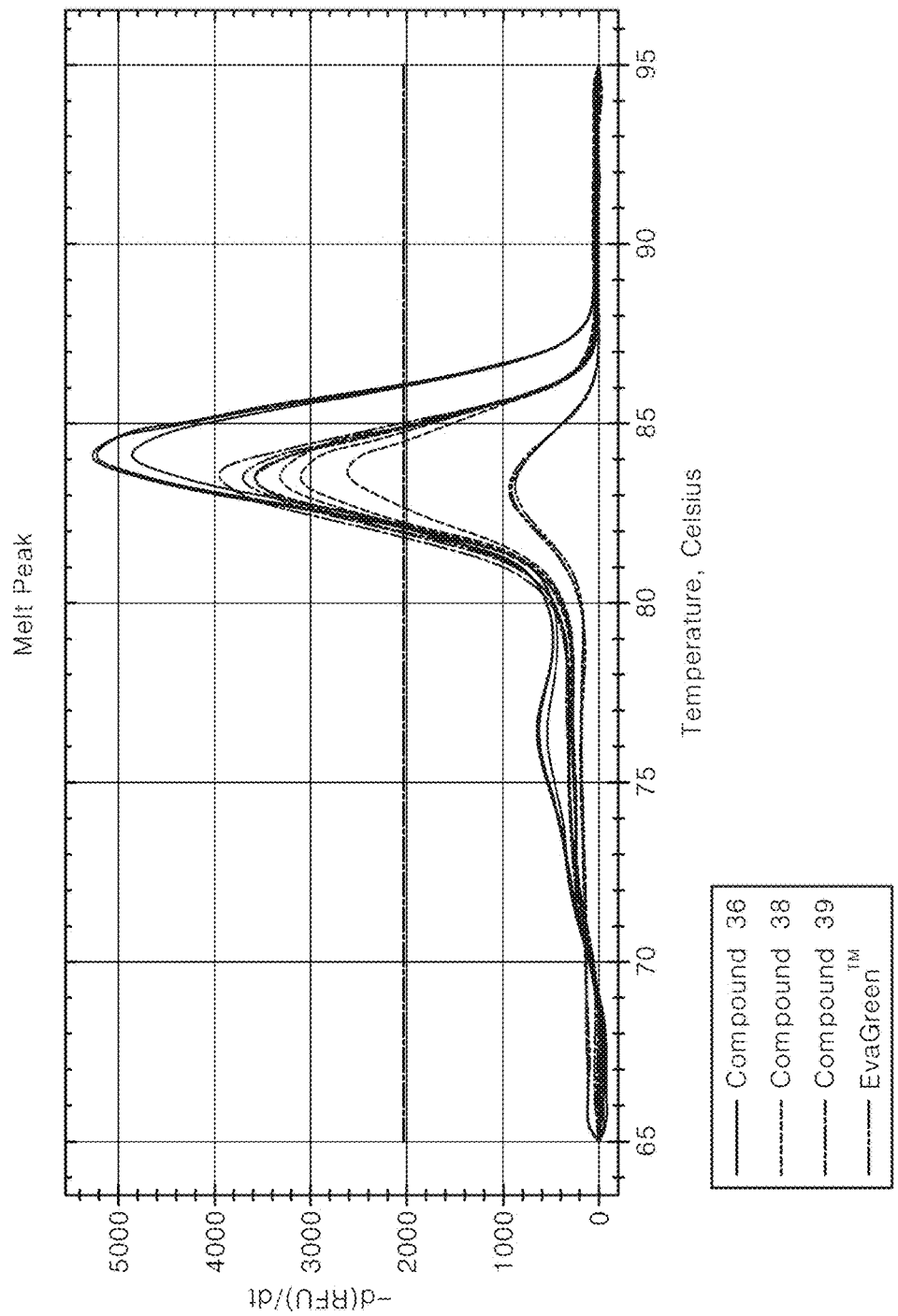
Figure 41:
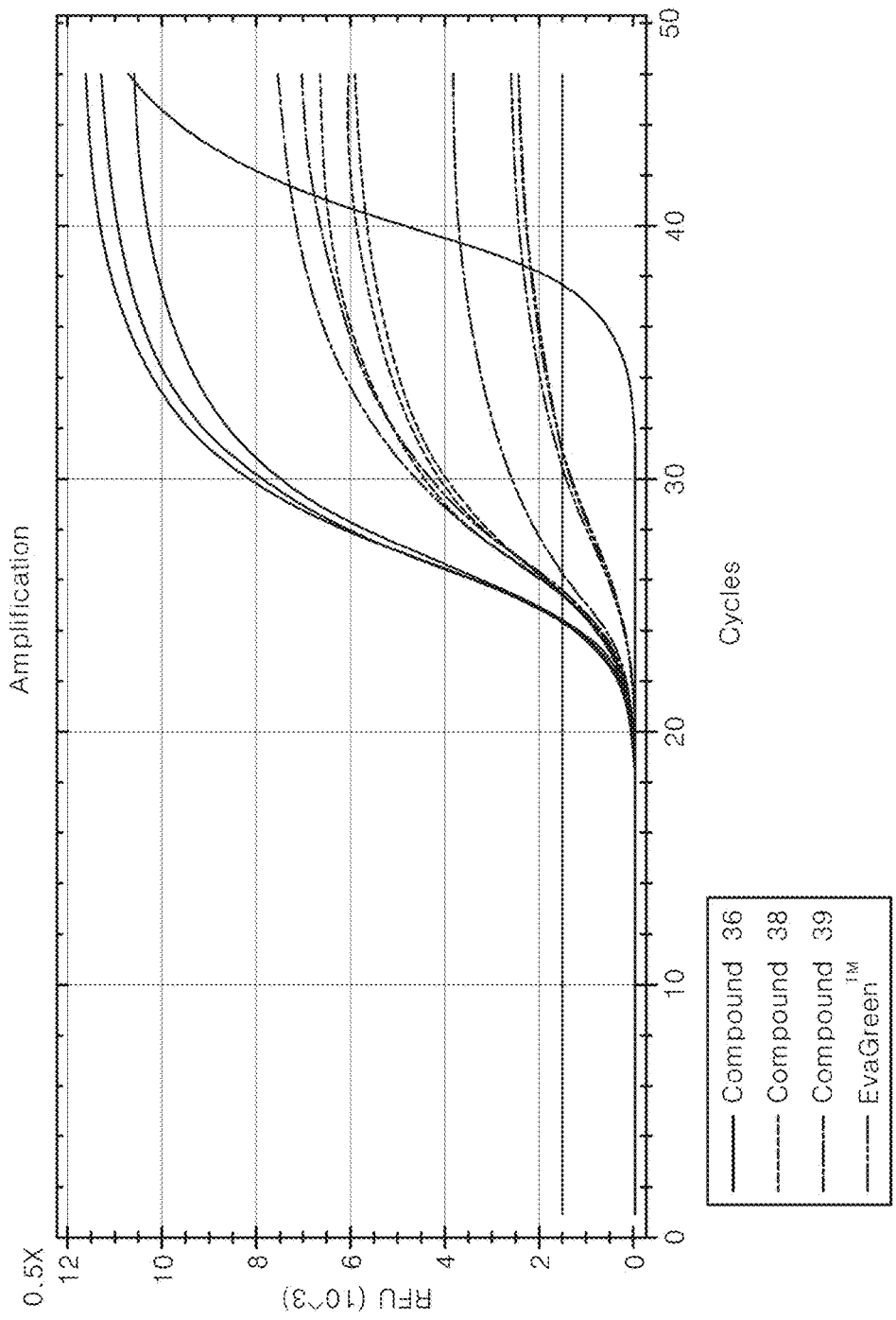
Figure 42:
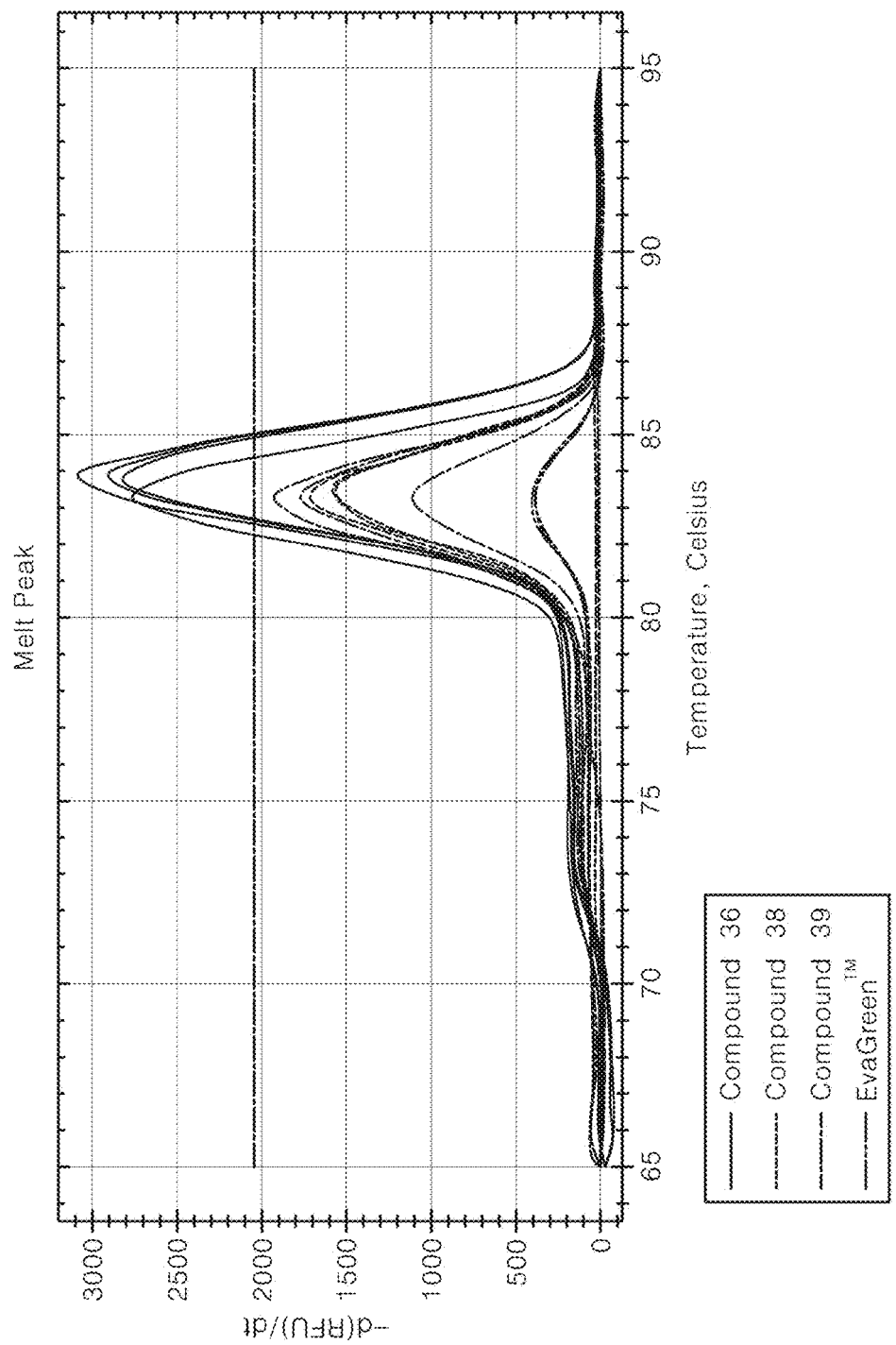

Cycles performed for 15 minutes at 95° C., 10 seconds at 95° C., 10 seconds at 60° C., and 30 seconds at 72° C. were repeated 40 times, and fluorescence was measured at 72° C. The qPCR was repeated three times in total, and the results of qPCR are shown in FIGS. 34 to 36, and Table 8 below.

TABLE 6

| Classification | cDNA content | 10 ng | 1 ng | 100 pg | 10 pg | 1 pg |
|---|---|---|---|---|---|---|
| compound 38 | Number of cycles (Ct) | 19.649 | 23.267 | 26.852 | 29.901 | 33.256 |
| | Tm (° C.) | 83.982 | 83.982 | 83.982 | 83.982 | 83.982 |

Here, threshold number of cycles (Ct) generally indicates the number of cycles at which fluorescence signal reaches any threshold value. For example, in qPCR amplification graph, it means the number of cycles at the point where the fluorescence signal begins to cross a reference line.

When qPCR was performed using Compound 38 as a fluorescent dye, the amplification efficiency was 97.44%, confirming that the amplification efficiency of qPCR did not decrease even when Compound 38 was contained in the reaction solution.

In addition, referring to Table 6, we confirmed that the sensitivity of Compound 38 to qPCR reaction is high in view of the fact that a PCR product is produced even when a very low concentration of cDNA sample such as 1 pg is used.

Figure 32:
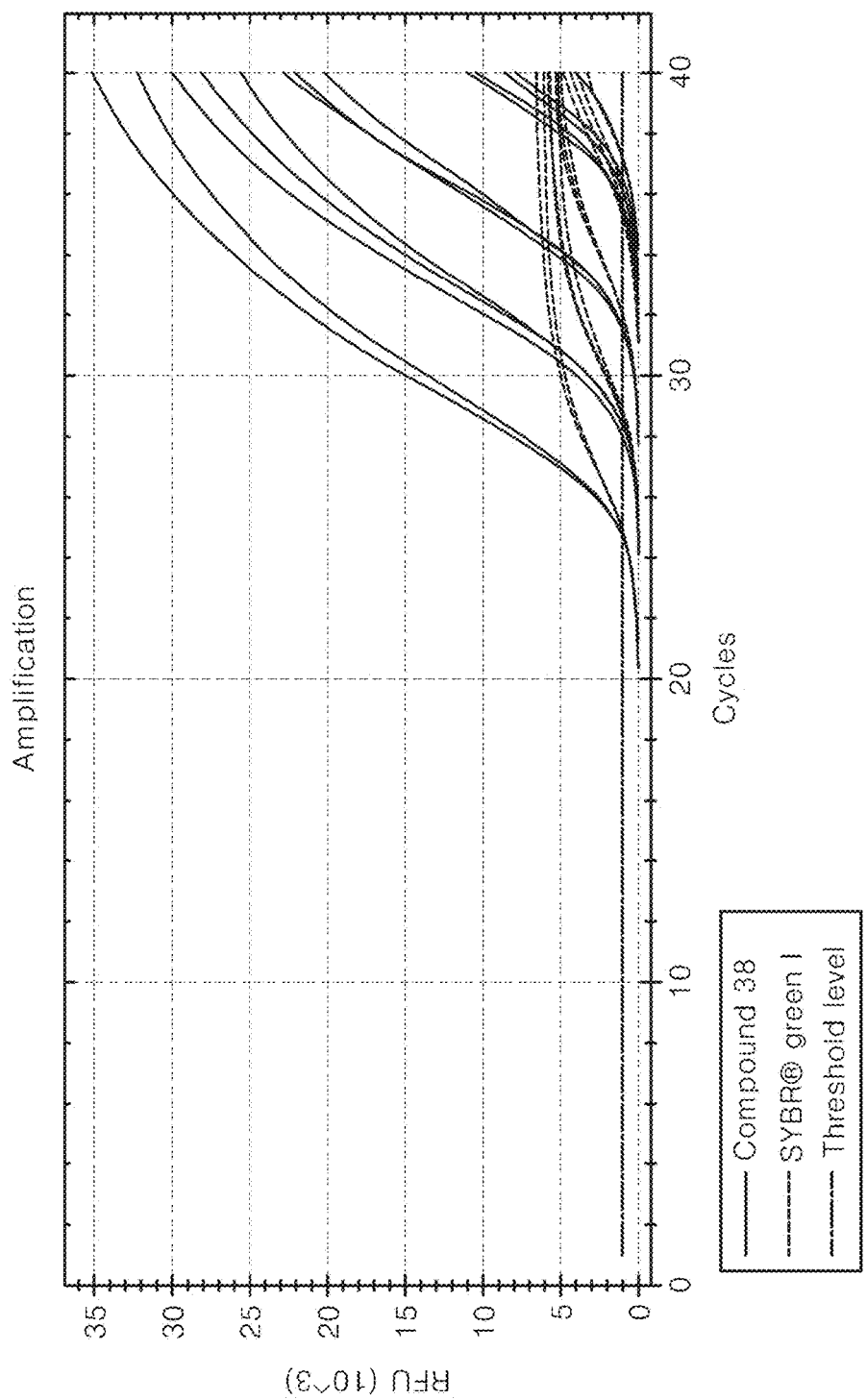
FIGS. 32 and 33 are graphs showing amplification curves of qPCR and melting curves of qPCR using SYBR® green I and Compound 38 as fluorescent dyes.
Figure 33:
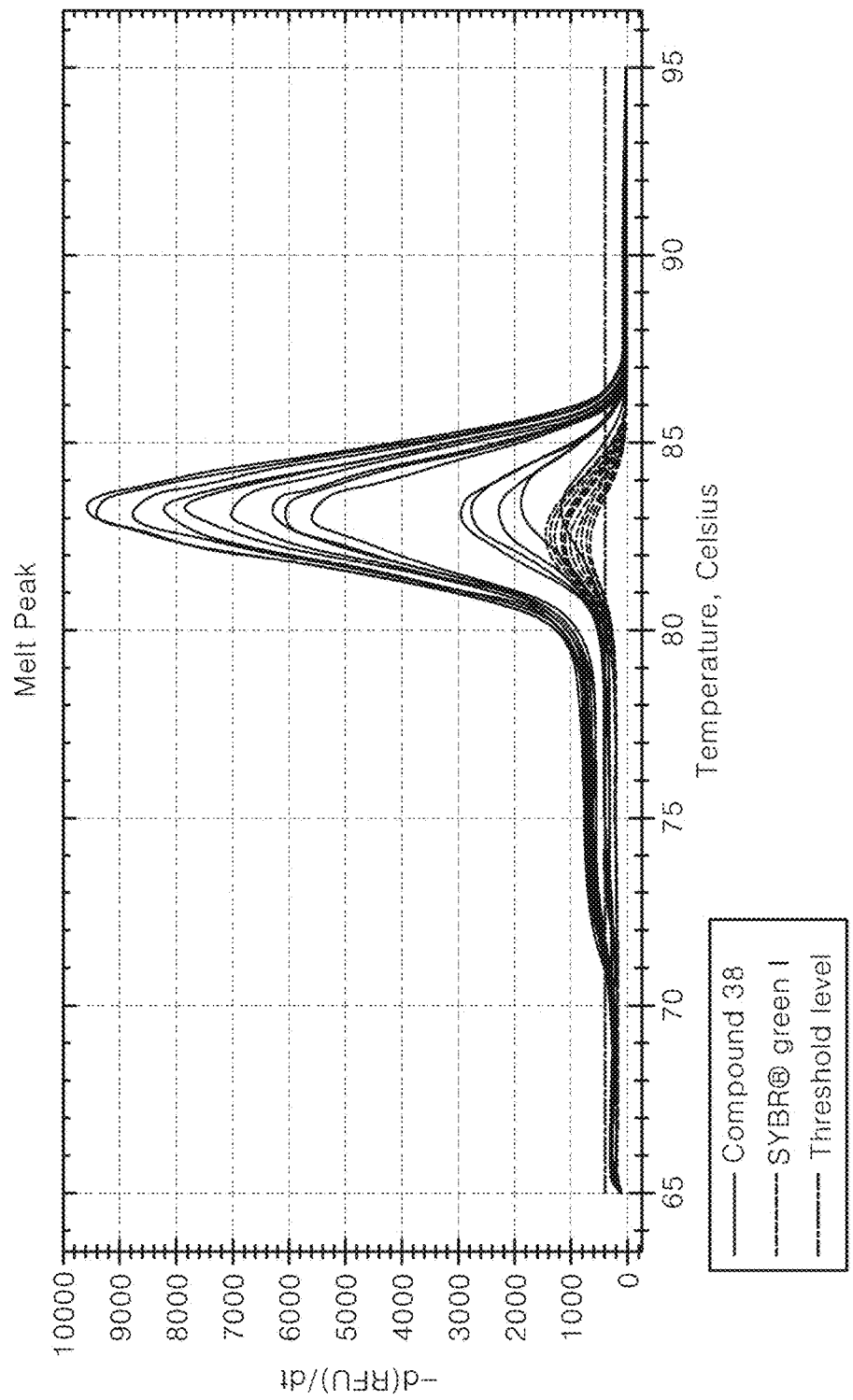

(2) qPCR was performed using CFX96 in a 20 µL reaction solution containing 10 µL of TOPreal™ qPCR 2× PreMIX (TagMan Probe, Enzynomics), Hela cDNA of various concentrations, 1 µL of 0.5 µM forward primer, 1 µL of 0.5 µM reverse primer, and SYBR® green I (0.45×) or Compound 38 (1×). The fragments in Hela cDNA were amplified using 0.5 µM forward primer 5'-GTATGACAACAGCCT-CAAGAT-3' (SEQ. ID. No. 1) and 0.5 µM reverse primer 5'-AGTCCTTCCACGATACCAAA-3' (SEQ. ID. No. 2). Cycles performed for 10 minutes at 95° C., 10 seconds at 95° C., 15 seconds at 60° C., and 15 seconds at 72° C. were repeated 40 times, and fluorescence was measured at 72° C. The qPCR was repeated three times in total, and the results of qPCR are shown in FIGS. 32 and 33, and Table 7 below.

TABLE 7

| Classification | cDNA content | Number of cycles (Ct) | End point RFU | Tm (° C.) |
|---|---|---|---|---|
| SYBR® green I | 1 ng | 24.70 | 6209.44 | 82.50 |
| | 0.1 ng | 28.47 | 5458.15 | 82.50 |
| | 0.01 ng | 31.97 | 4736.22 | 82.50 |
| | 0.001 ng | 35.66 | 2818.84 | 82.50 |
| | 0.0001 ng | 36.99 | 1250.30 | 82.50 |
| Compound 38 | 1 ng | 24.45 | 31885.43 | 83.17 |
| | 0.1 ng | 28.12 | 24568.08 | 83.00 |
| | 0.01 ng | 31.42 | 16545.25 | 83.00 |
| | 0.001 ng | 35.63 | 5033.85 | 83.00 |
| | 0.0001 ng | 36.88 | 1818.80 | 83.25 |

When qPCR was performed using Compound 38 as a fluorescent dye, we confirmed that Ct values were 0.5 or less as compared with SYBR® green I, and RFU values were about 5 times or more.

(3) qPCR was performed using ABI 7500 FAST in 20 µL reaction solution containing 10 µL of 2× Real-Time PCR Master Mix (DQ372, BioFACT), 2 µL of Hg DNA (25 ng/µL), 1 µL of Primer (HSP98), and fluorescent dyes of various concentrations (dilution times) (Compound 38, SYBR® green I (Invitrogen) or EvaGreen™ (Biotium)).

TABLE 8

| Fluorescent dye | Fluorescent dye concentration | 1X | 0.5X | 0.25X |
|---|---|---|---|---|
| Compound 38 | Number of cycles (Ct) | 23.17 | 23.61 | 24.53 |
| | Fluorescence intensity (Rn) | 37.83 | 21.42 | 11.18 |
| | Tm (° C.) | 79.04 | 79.2 | 79.04 |
| SYBR® green I | Number of cycles (Ct) | N/D | 25.61 | 24.93 |
| | Fluorescence intensity (Rn) | 0.22 | 8.04 | 4.01 |
| | Tm (° C.) | 89.3 | 80.75 | 80.13 |
| EvaGreen™ | Number of cycles (Ct) | 25.29 | 25.8 | 26.82 |
| | Fluorescence intensity (Rn) | 17.25 | 9.58 | 4.59 |
| | Tm (° C.) | 79.04 | 79.04 | 78.89 |

When qPCR was performed using Compound 38 as a fluorescent dye, we confirmed that Ct values were smaller than those in the case of using SYBR® green I or EvaGreen™ at the same dilution times. Also, we confirmed that the fluorescence intensities were about twice as high as those of using the same dilution times of SYBR® green I or EvaGreen™.

Further, from the results in Table 8, it can be seen that Compound 38 at a higher concentration than that of SYBR® green I can be used without inhibiting qPCR reaction.

Figure 20:
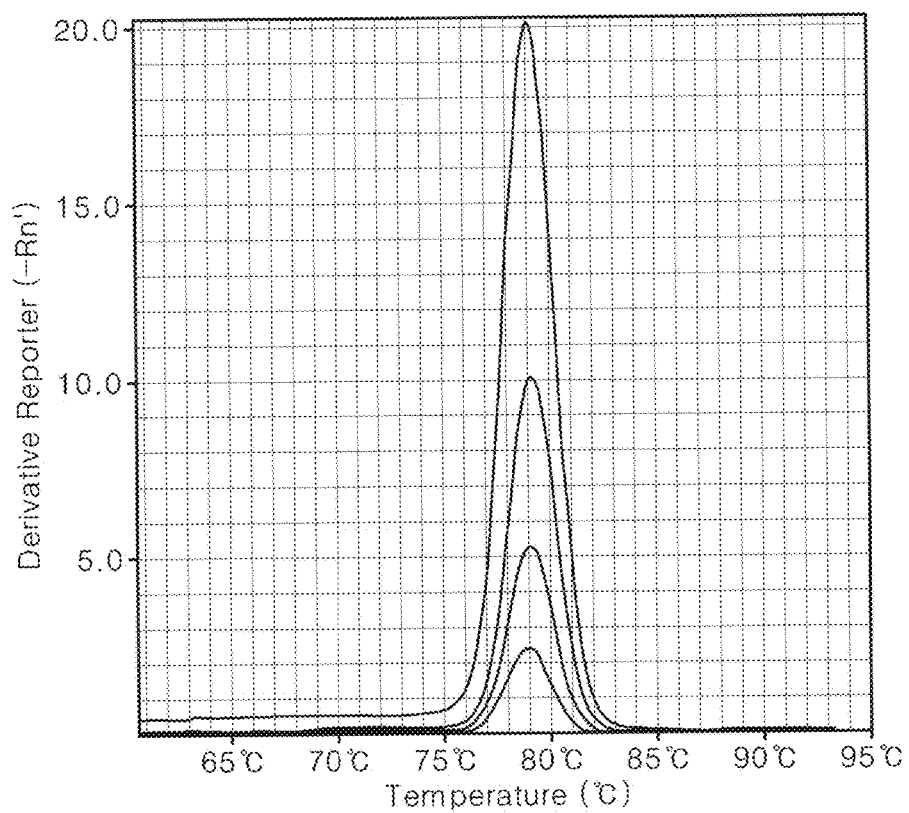
FIG. 20 is a graph showing a melting curve of qPCR using Compound 38 as a fluorescent dye.
Figure 21:
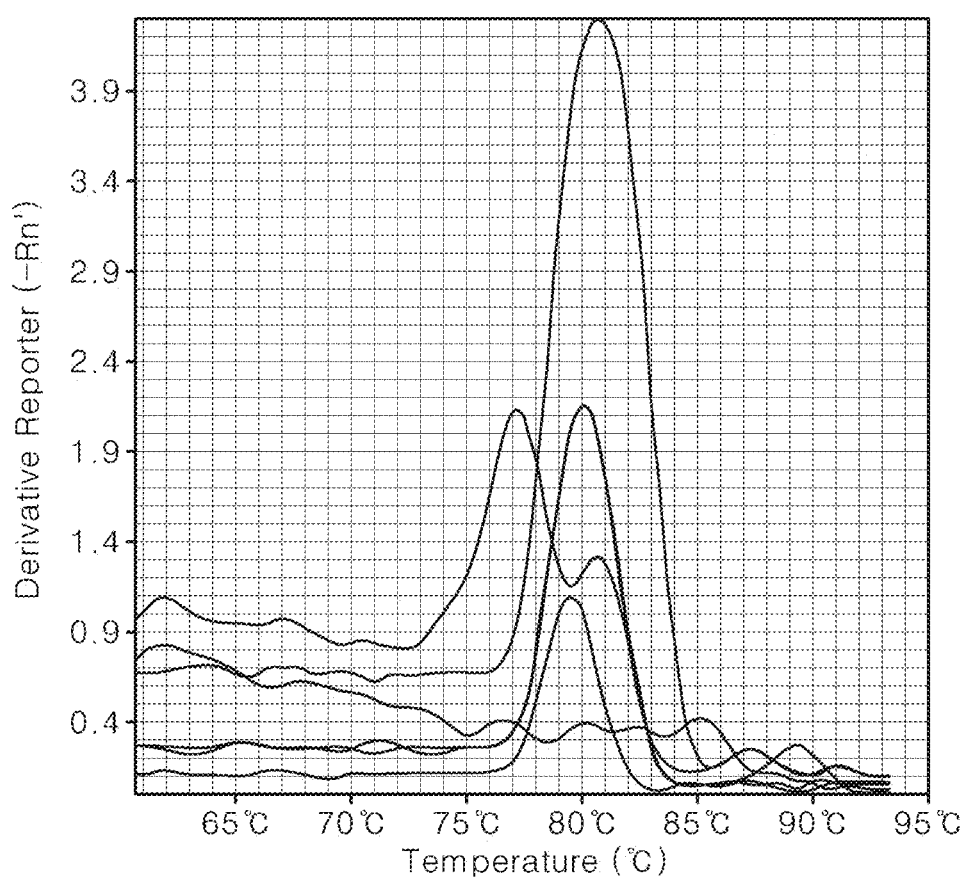
FIG. 21 is a graph showing a melting curve of qPCR using SYBR® green I as a fluorescent dye.
Figure 22:
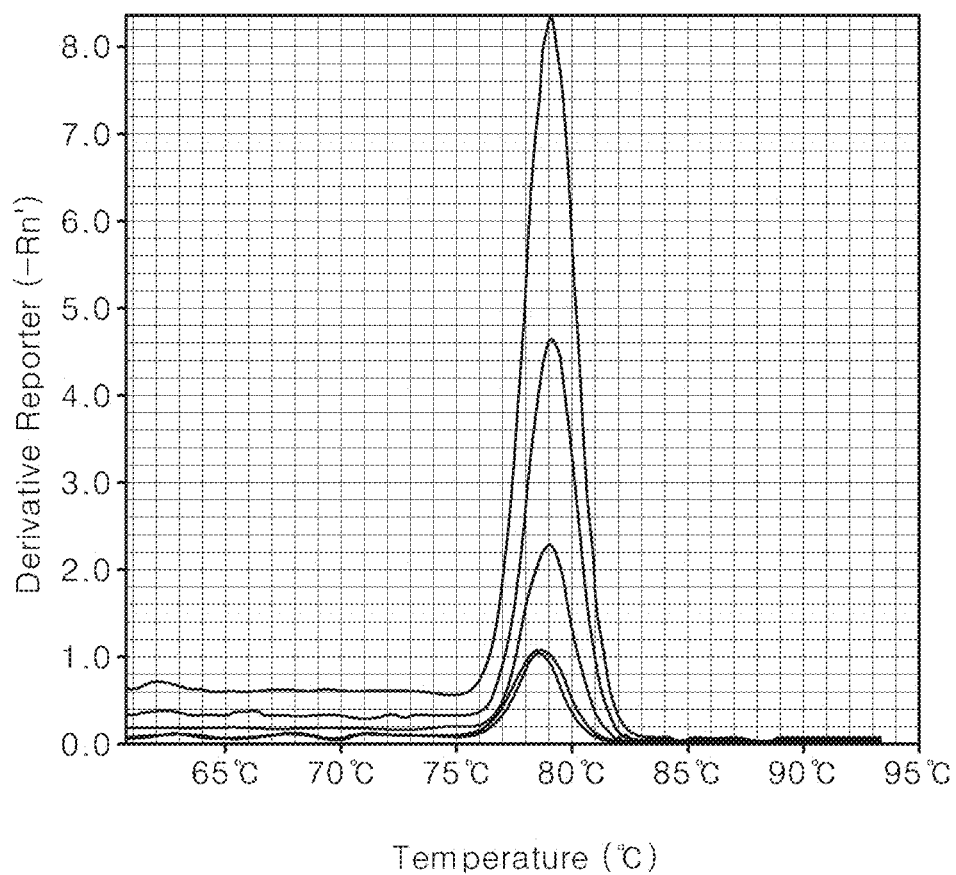
FIG. 22 is a graph showing a melting curve of qPCR using EvaGreen™ as a fluorescent dye.

FIG. 20 is a graph showing a melting curve of qPCR using Compound 38 as a fluorescent dye, FIG. 21 is a graph showing a melting curve of qPCR using SYBR® green I as a fluorescent dye, and FIG. 22 is a graph showing a melting curve of qPCR using EvaGreen™ as a fluorescent dye.

Referring to FIGS. 20-22, it can be seen that qPCR using Compound 38 and EvaGreen™ shows a single specific peak, whereas qPCR using SYBR® green I shows an extra primer-dimer peak.

(4) qPCR was performed using CFX96 in 20 µL reaction solution containing 10 µL of 2× Real-Time PCR Master Mix (Cellsafe), fluorescent dyes of various concentrations (Compound 36, Compound 38, Compound 39, SYBR® green I (Invitrogen) or EvaGreen™ (Biotium), 4 µL of Hela cDNA (0.5 ng/µL) and 1 µL of primer (GAPDH). Cycles performed at 95° C. for 10 minutes, 95° C. for 10 seconds, and 60° C. for 1 minute were repeated 46 times, and fluorescence was measured at 60° C. The results of qPCR are shown in FIGS. 37 to 42, and Table 9 below.

TABLE 9

| Fluorescent dye | Fluorescent dye concentration | 2X | 1X | 0.5X |
|---|---|---|---|---|
| Compound 36 | Number of cycles (Ct) | 39.66 | 30.55 | 24.32 |
| | End point RFU | 14645 | 21485 | 11100 |
| | Tm (° C.) | 78.3 | 84.0 | 84.0 |
| Compound 38 | Number of cycles (Ct) | 26.2 | 24.59 | 25.40 |
| | End point RFU | 27677 | 15460 | 7212 |
| | Tm (° C.) | 84.0 | 83.5 | 83.5 |

TABLE 9-continued

| Fluorescent dye | Fluorescent dye concentration | 2X | 1X | 0.5X |
|---|---|---|---|---|
| Compound 39 | Number of cycles (Ct) | 26.87 | 24.69 | 25.31 |
| | End point RFU | 24717 | 13320 | 6176 |
| | Tm (° C.) | 84.0 | 83.5 | 83.5 |
| EvaGreen™ | Number of cycles (Ct) | 27.48 | 27.09 | 30.80 |
| | End point RFU | 10223 | 5941 | 2487 |
| | Tm (° C.) | 83.5 | 83.3 | 83.0 |

When Compound 38 and Compound 39 were used at a relatively high concentration (2×, 1×) of fluorescent dye concentration, it was confirmed that the Ct values were low and the fluorescence intensities were high as compared with the case of using EvaGreen™ of the same dilution times. In the case of a relatively low concentration (0.5×) of fluorescent dye concentration, Compound 36 was also found to have a lower Ct value and a higher fluorescence intensity than SYBR® green I or EvaGreen™ with the same dilution times.

Experimental Example 6

Thermal Stability Test

In order to confirm the stability of the fluorescent dye in the PCR reaction, 20 μL of PCR reaction buffer containing 1 μL of Compound 38 and 1 μL of EvaGreen™ (Biotium), respectively, was prepared. Each PCR reaction buffer was heated to 95° C., and the absorbance which varies with the standing time at 95° C. was measured.

The absorbance shown in the following Table 10 indicates that the absorbance variation according to the standing time at 95° C. is smaller than that of EvaGreen™. That is, the high temperature stability of Compound 38 will be greater than EvaGreen™.

TABLE 10

| Classification | Standing time (hr) | 0 | 0.5 | 1 | 2 | 3 |
|---|---|---|---|---|---|---|
| Absorbance | Compound 38 | 0.127 | 0.149 | 0.162 | 0.163 | 0.178 |
| | EvaGreen™ | 0.095 | 0.125 | 0.135 | 0.167 | 0.190 |

Experimental Example 7

Photobleaching Test

Real-Time PCR was performed in a 20 μL reaction solution containing only 5 μL of fluorescent dyes (Compound 38, SYBR® green I (Invitrogen) or EvaGreen™ (Biotium)) at various concentrations (dilution times). Cycles of 30 seconds at 25° C. and 30 seconds at 25° C. were repeated 60 times. Fluorescence intensity was measured for each cycle (1 minute) to observe photobleaching of fluorescent dyes at various concentrations (dilution times).

Figure 23:
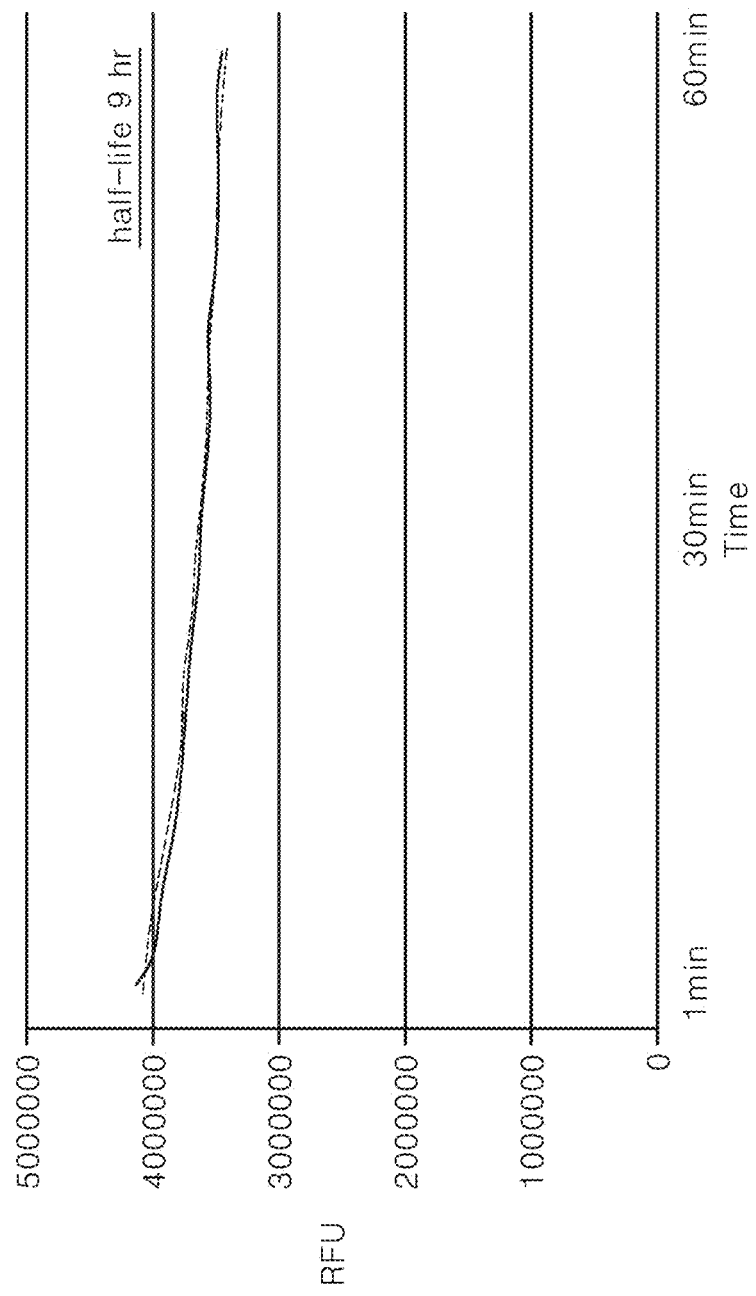
FIGS. 23 to 25 are graphs showing results of photobleaching test of Compound 38.
Figure 24:
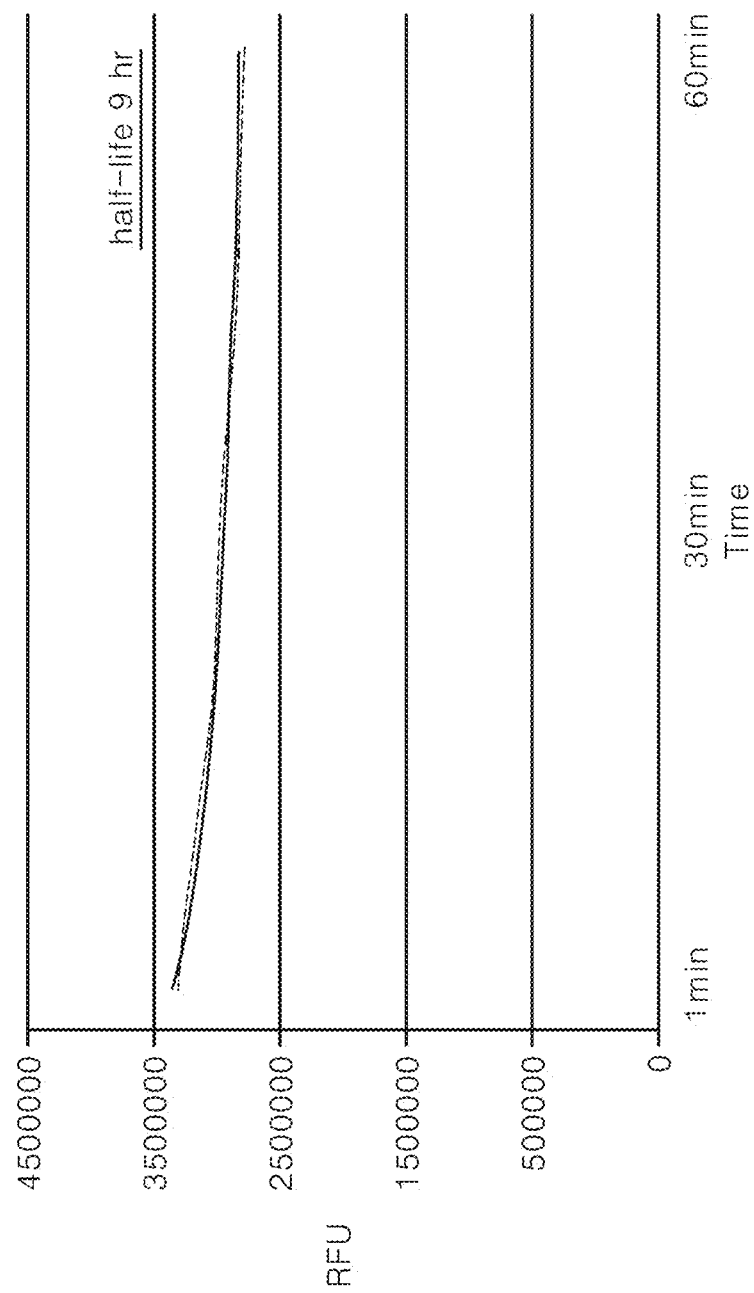
Figure 25:
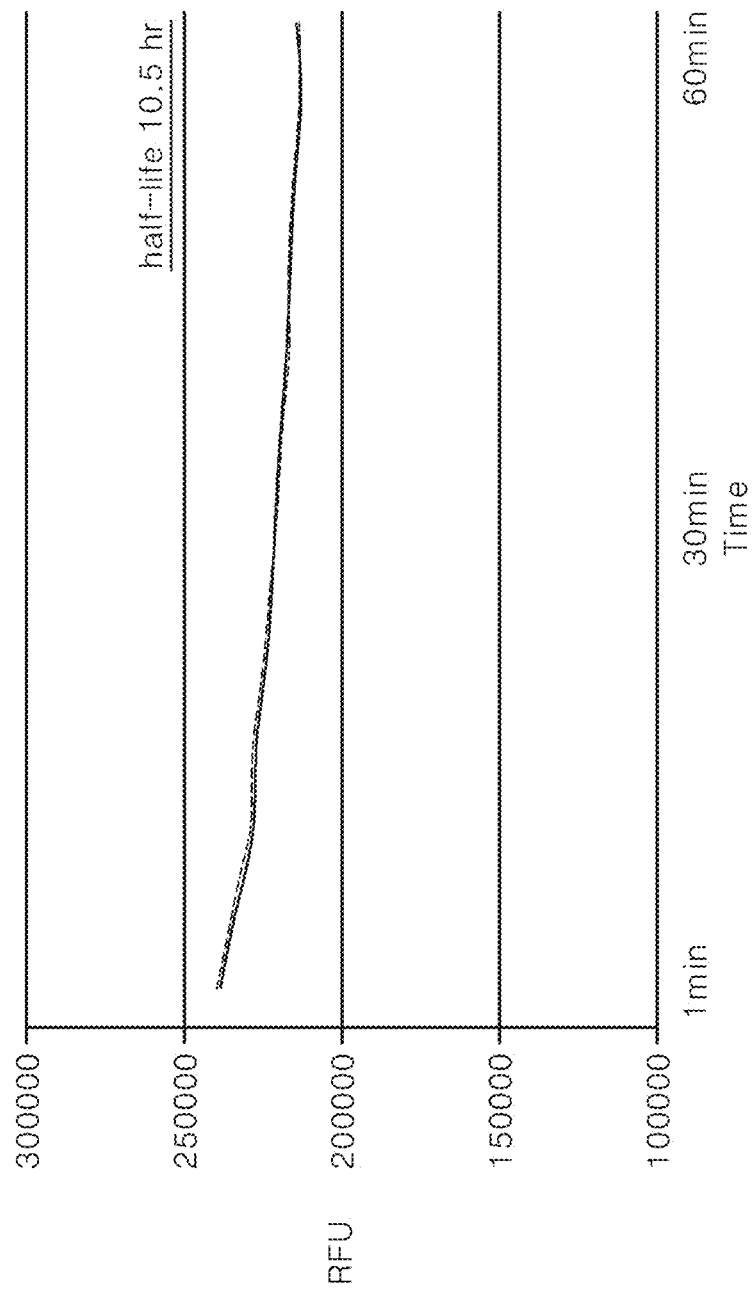
Figure 26:
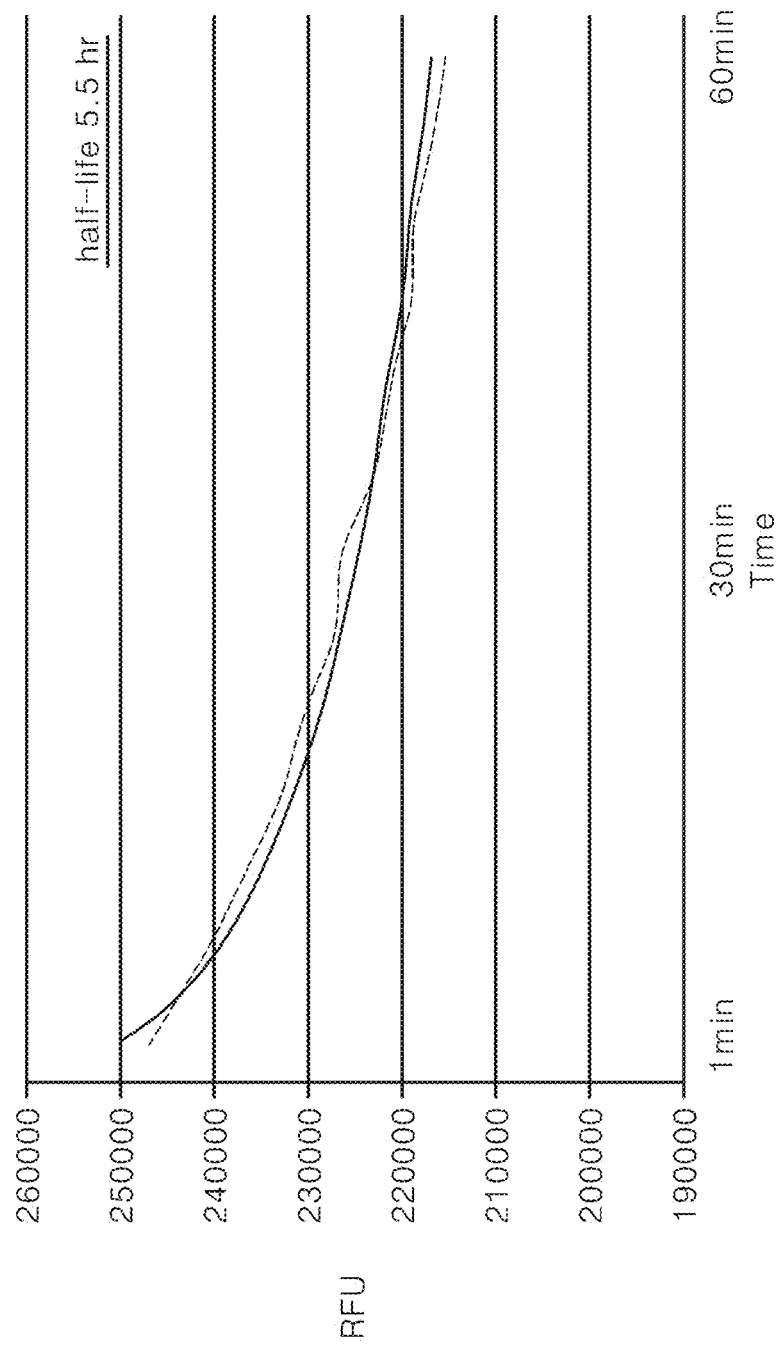
FIGS. 26 to 28 are graphs showing results of photobleaching test of SYBR® green I (manufactured by Invitrogen)
Figure 27:
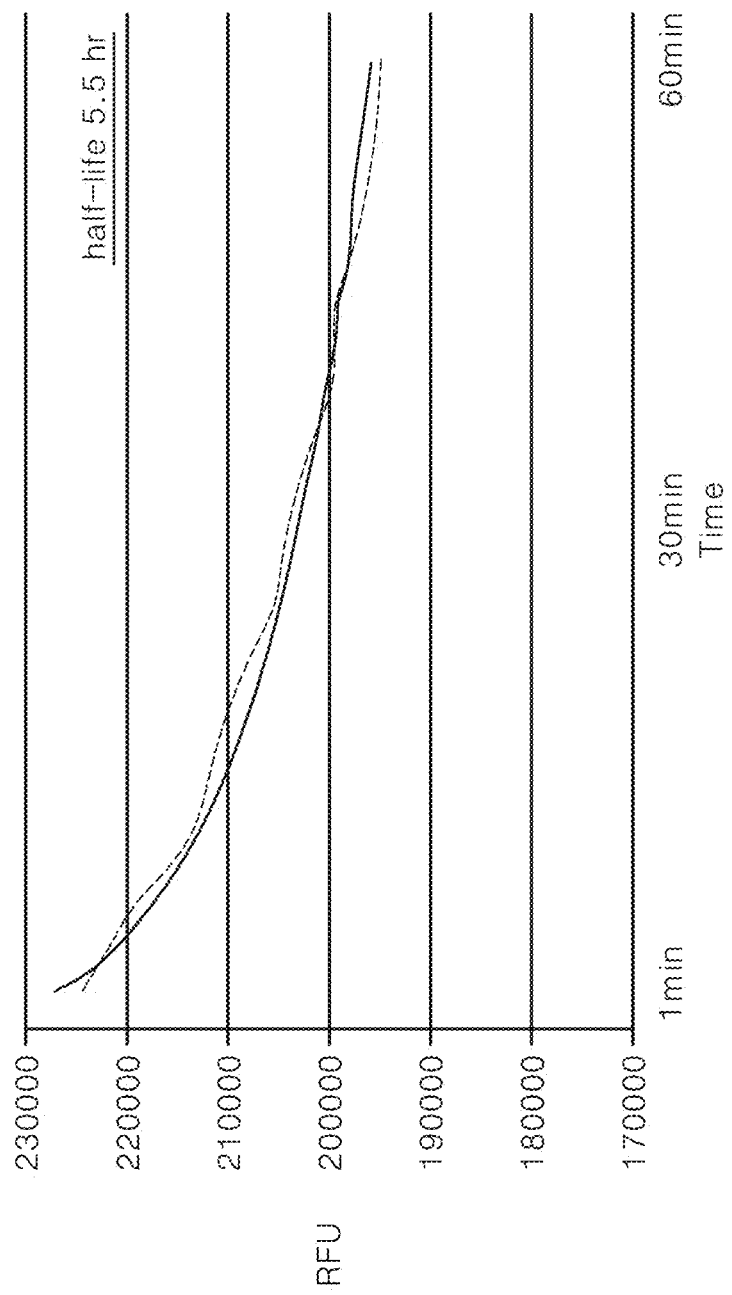
Figure 28:
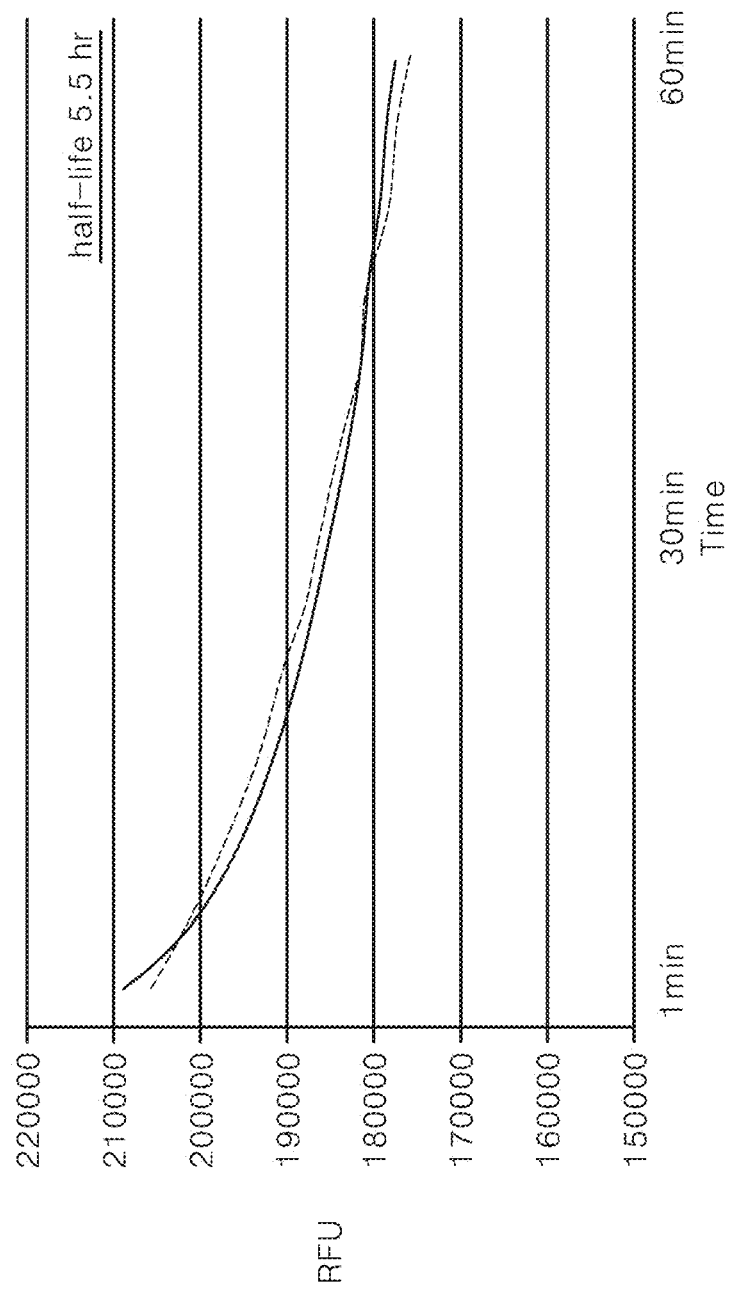
Figure 29:
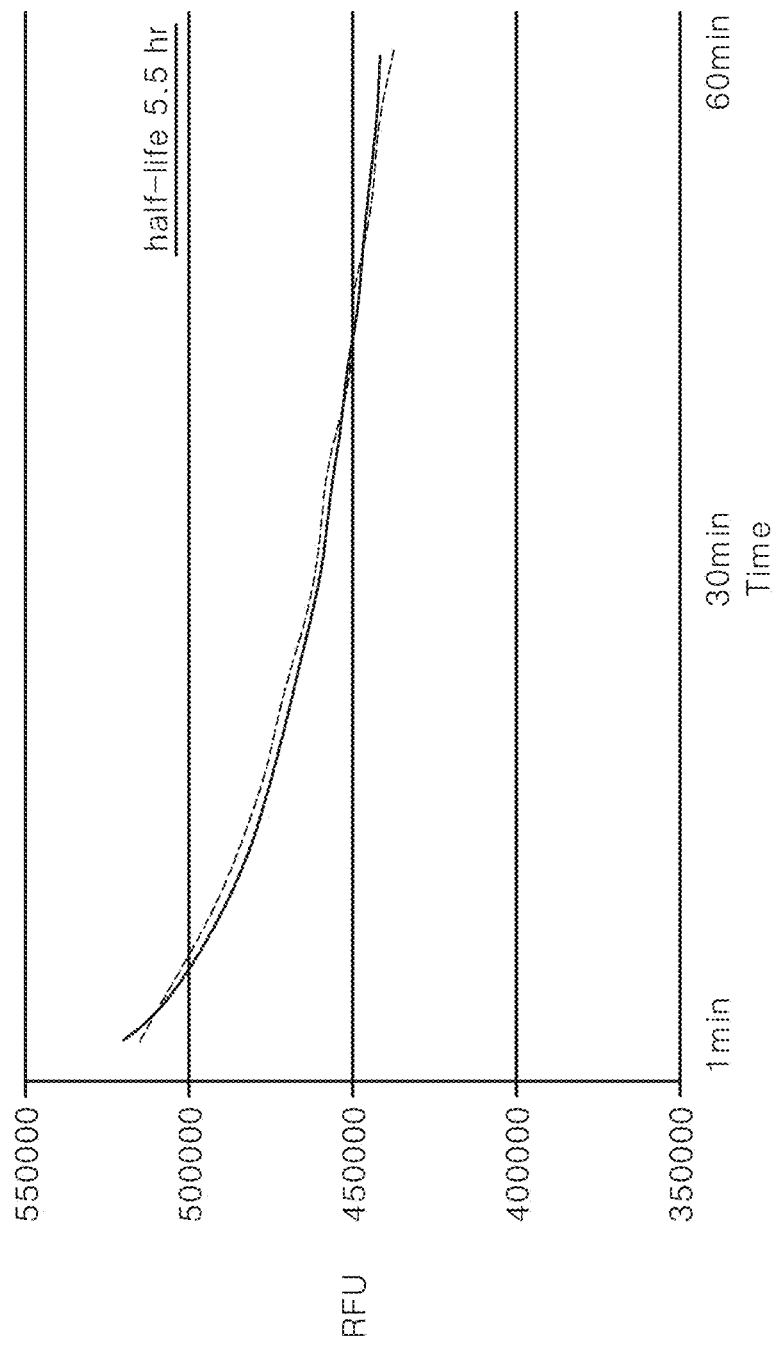
FIGS. 29 to 31 are graphs showing results of photobleaching test of EvaGreen™ (manufactured by Biotium).
Figure 30:
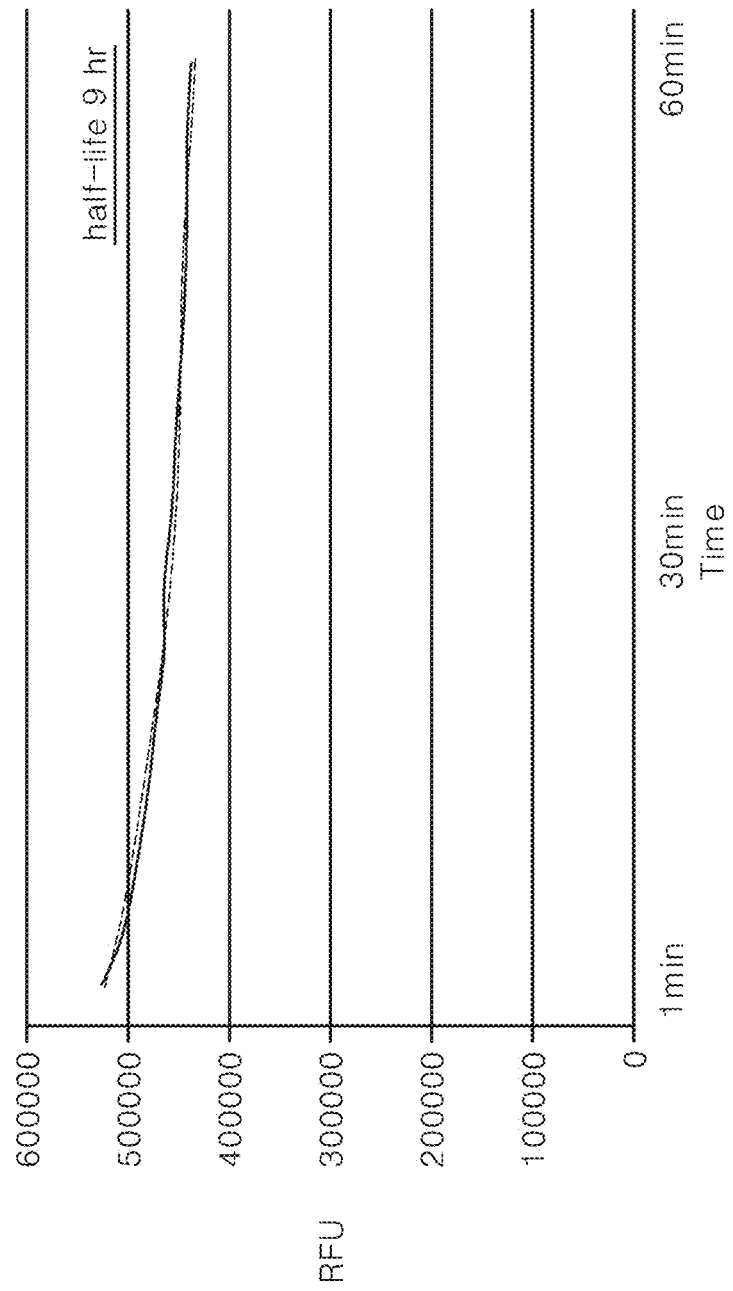
Figure 31:
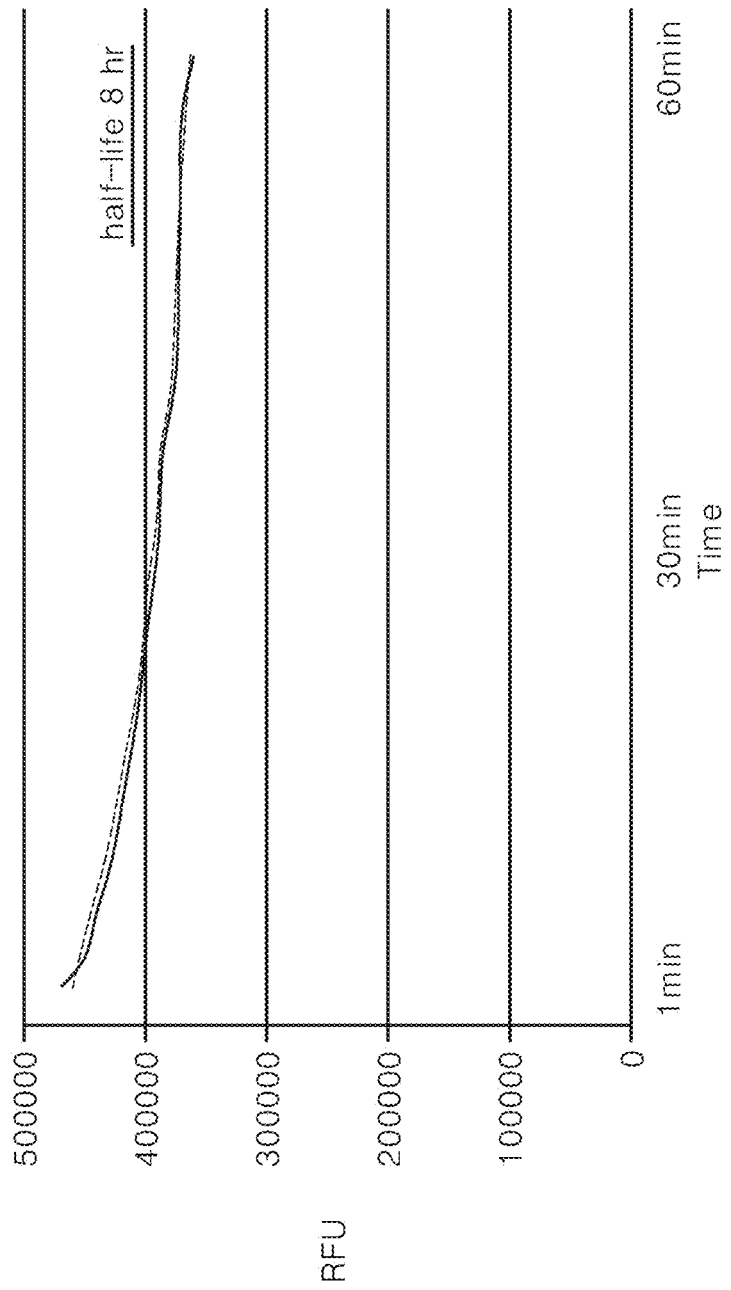

The results of the photobleaching test of Compound 38 measured according to the above-described method are shown in FIGS. 23 to 25, the results of photobleaching test of SYBR® green I (Invitrogen) are shown in FIGS. 26 to 28, and the results of photobleaching test of EvaGreen™ (Biotium) are shown in FIGS. 29 to 31.

FIGS. 26, 27 and 28 show the changes in fluorescence intensity measured with SYBR® green I at a dilution times of 0.5×, 0.25×, and 0.125×, respectively. In the case of SYBR® green I, it can be seen that the half-life at low concentration is only 5.5 hours.

FIGS. 23 and 29, FIGS. 24 and 30, and FIGS. 25 and 31 show the changes in fluorescence intensity measured with Compound 28 or EvaGreen™ at a dilution times of 1×, 0.5×, and 0.25×, respectively. When Compound 38 was used, it can be seen that Compound 38 exhibits a half-life similar or higher than that of EvaGreen™ at the same concentration.

Although various embodiments of the present disclosure has been described above, it will be apparent to those skilled in the art that various modifications and changes can be made in the present disclosure by additions, alterations, deletions, etc. to components without departing from the spirit and scope of the invention as set forth in the appended claims, which also fall within the scope of the present disclosure.

What is claimed is:

1. A merocyanine-based compound having a structure represented by the following formula 1:

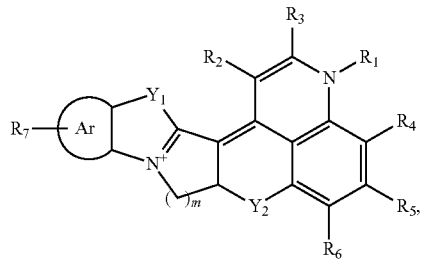

[Formula 1]

wherein

Ar is a substituted or unsubstituted aromatic ring;

$Y_1$ and $Y_2$ are each independently selected from sulfur, oxygen, selenium, $NR_8$ and $-CR_8=CR_9-$;

$R_1$ to $R_9$ are each independently selected from the group consisting of hydrogen, deuterium, substituted or unsubstituted $C_1-C_{10}$ alkyl, substituted or unsubstituted $C_2-C_{10}$ heteroalkyl containing at least one heteroatom, substituted or unsubstituted $C_2-C_{10}$ alkenyl, substituted or unsubstituted $C_2-C_{10}$ alkynyl, substituted or unsubstituted $C_1-C_{10}$ alkoxy, substituted or unsubstituted aryloxy, substituted or unsubstituted $C_1-C_{10}$ haloalkyl, halogen, cyano, hydroxyl, substituted or unsubstituted amino, substituted or unsubstituted amide, carbamate, sulthydryl, nitro, carboxyl, carboxylate, substituted or unsubstituted aryl, substituted or unsubstituted heteroaryl, substituted or unsubstituted aralkyl, quaternary ammonium, phosphoric acid, phosphate, phosphonate, $-COR_{10}$, aldehyde, $-COOR_{10}$, acyl chloride, sulfonic acid, sulfonate, polyalkylene oxide, and -L-Z functional groups;

when $R_a$, wherein a is an integer selected from 1 to 9, is a $-COR_{10}$ group or a $-COOR_{10}$ group, $R_{10}$ is selected from the group consisting of substituted or unsubstituted $C_1-C_{10}$ alkyl, substituted or unsubstituted $C_2-C_{10}$ heteroalkyl containing at least one heteroatom, substituted or unsubstituted $C_2-C_{10}$ alkenyl, substituted or unsubstituted $C_2-C_{10}$ alkynyl, substituted or unsubstituted $C_1-C_{10}$ alkoxy, substituted or unsubstituted $C_1-C_{10}$ haloalkyl, and substituted or unsubstituted $C_1-C_{10}$ aminoalkyl;

when $R_b$, wherein b is an integer selected from 1 to 10, is substituted, any carbon or terminal carbon in the functional groups may be substituted with at least one substituent selected from the group consisting of sulfonic acid, sulfonate, ketone, aldehyde, carboxylic acid, carboxylate, phosphoric acid, phosphate, phosphonate, acyl chloride, polyalkylene oxide, quaternary ammonium salt, ester, and amide;

m is an integer of 1 to 3;

L is a linker comprising 3 to 150 non-hydrogen atoms;

Z is a fluorescent moiety capable of generating a fluorescent signal, or has a structure represented by formula 1; and wherein the structure represented by the formula 1 has one or two -L-Z functional groups.

2. The merocyanine-based compound of claim 1, wherein Z is selected from the group consisting of phenanthridium, coumarins, cyanine, bodipy, fluoresceins, rhodamines, pyrenes, carbopyronin, oxazine, xanthenes, thioxanthene, and acridine.

3. The merocyanine-based compound of claim 1, wherein the -L-Z functional group is represented by the following formula 2:

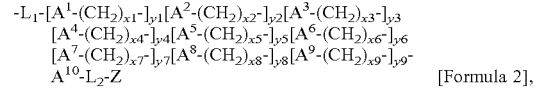

[Formula 2], wherein $L_1$ and $L_2$ are each independently a $C_1-C_{12}$ polymethylene unit optionally containing at least one heteroatom selected from nitrogen, oxygen and sulfur, or an aryl optionally containing at least one heteroatom selected from nitrogen, oxygen and sulfur;

$A^1$ to $A^{10}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur;

x1 to x9 are each independently 0 or an integer of 1 to 20;

y1 to y9 are each independently 0 or an integer of 1 to 20; and

Z is selected from the group consisting of phenanthridium, coumarins, cyanine, bodipy, fluoresceins, rhodamines, pyrenes, carbopyronin, oxazine, xanthenes, thioxanthene, and acridine.

4. The merocyanine-based compound of claim 3, wherein one of $A^1$ to $A^{10}$ is represented by the following formula 3:

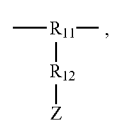

[Formula 3]

wherein $R_{11}$ is an aryl optionally containing at least one heteroatom selected from nitrogen, oxygen and sulfur;

$R_{12}$ is represented by the following formula 4:

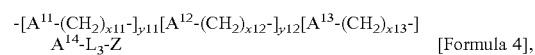

[Formula 4], wherein $L_3$ is a $C_1-C_{12}$ polymethylene unit optionally containing at least one heteroatom selected from nitrogen, oxygen and sulfur, or an aryl optionally containing at least one heteroatom selected from nitrogen, oxygen and sulfur;

$A^{11}$ to $A^{14}$ are each independently a chain alkyl or branched alkyl optionally containing at least one heteroatom selected from nitrogen, oxygen and sulfur, or a five- or six-membered ring optionally containing at least one heteroatom selected from nitrogen, oxygen and sulfur;

x11 to x13 are each independently 0 or an integer of 1 to 20; and y11 to y13 are each independently 0 or an integer of 1 to 20.

5. A dye for labeling biomolecules comprising the merocyanine-based compound according to claim 1.

6. The dye for labeling biomolecules of claim 5, wherein the merocyanine-based compound is a compound that is intercalated into a nucleic acid which is a biomolecule.

7. The dye for labeling biomolecules of claim 6, wherein the biomolecule is at least one nucleic acid selected from a single-stranded RNA, a double-stranded RNA, a single-stranded DNA, and a double-stranded DNA.

8. A kit for labeling biomolecules comprising the merocyanine-based compound according to claim 1.

9. The kit of claim 8, wherein the kit is an electrophoresis kit, wherein the electrophoresis kit comprises the merocyanine-based compound; and a buffer, a gel matrix, at least one material for forming a gel matrix, or at least one material for forming a surface.

10. A method for determining the presence or absence of nucleic acids in a sample, comprising:
   when the nucleic acids are present in a sample,
   exposing the nucleic acids to the merocyanine-based compound according to claim 1, such that the merocyanine-based compound is intercalated into the nucleic acids to form a complex; and
   determining the presence or absence of fluorescence of the merocyanine-based compound.

11. A method for determining the presence or absence of an amplified target nucleic acid, comprising:
   when performing a nucleic acid amplification reaction,
   providing a reaction mixture comprising a target nucleic acid, a reagent necessary for amplifying the target nucleic acid, and the merocyanine-based compound according to claim 1;
   subjecting the reaction mixture to polymerization under conditions suitable for the formation of the amplified target nucleic acid;
   illuminating the reaction mixture with light; and
   detecting a fluorescence emission from the reaction mixture.

12. The kit of claim 8, wherein the kit is for determining the viability of cells in a sample, the kit comprises the merocyanine-based compound; and when apoptotic cells are present in a sample, fluorescence is detected by intercalating them with the merocyanine-based compound.

* * * * *